United States Patent
Shou et al.

(10) Patent No.: US 9,465,029 B2
(45) Date of Patent: *Oct. 11, 2016

(54) METHODS FOR DETECTING LP-PLA2 ACTIVITY AND INHIBITION OF LP-PLA2 ACTIVITY

(71) Applicant: Glaxo Group Limited, Greenford (GB)

(72) Inventors: Yaping Shou, Research Triangle Park, NC (US); Yin Fai Amy Siu, Research Triangle Park, NC (US); George T. Walker, Reserach Triangle Park, NC (US)

(73) Assignee: Glaxo Group Limited, Middlesex (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/700,053

(22) Filed: Apr. 29, 2015

(65) Prior Publication Data

US 2015/0247858 A1 Sep. 3, 2015

Related U.S. Application Data

(63) Continuation of application No. 14/498,980, filed on Sep. 26, 2014, which is a continuation-in-part of application No. 12/817,677, filed on Jun. 17, 2010, now Pat. No. 8,846,309, which is a continuation of application No. 11/106,239, filed on Apr. 14, 2005, now Pat. No. 7,741,020.

(60) Provisional application No. 60/563,078, filed on Apr. 16, 2004.

(51) Int. Cl.
*G01N 33/573* (2006.01)
*C12Q 1/44* (2006.01)
*G01N 33/58* (2006.01)

(52) U.S. Cl.
CPC ............... *G01N 33/573* (2013.01); *C12Q 1/44* (2013.01); *G01N 33/581* (2013.01); *C12Q 2334/10* (2013.01); *G01N 2333/918* (2013.01); *G01N 2500/02* (2013.01); *G01N 2500/04* (2013.01); *G01N 2500/20* (2013.01)

(58) Field of Classification Search
CPC ....................................................... C12Q 1/44
See application file for complete search history.

(56) References Cited

U.S. PATENT DOCUMENTS

| | | | |
|---|---|---|---|
| 3,773,391 A | 11/1973 | Boswell et al. | |
| RE30,985 E | 6/1982 | Cartaya | |
| 4,485,045 A | 11/1984 | Regen | |
| 4,544,545 A | 10/1985 | Ryan et al. | |
| 4,560,655 A | 12/1985 | Baker | |
| 4,657,866 A | 4/1987 | Kumar | |
| 4,676,980 A | 6/1987 | Segal et al. | |
| 4,767,704 A | 8/1988 | Cleveland et al. | |
| 4,816,567 A | 3/1989 | Cabilly et al. | |
| 4,892,538 A | 1/1990 | Aebischer et al. | |
| 4,927,762 A | 5/1990 | Darfler | |
| 4,975,278 A | 12/1990 | Senter et al. | |
| 5,013,556 A | 5/1991 | Woodle et al. | |
| 5,091,527 A | 2/1992 | Junius et al. | |
| 5,122,469 A | 6/1992 | Mather et al. | |
| 5,208,020 A | 5/1993 | Chari et al. | |
| 5,229,275 A | 7/1993 | Goroff | |
| 5,283,187 A | 2/1994 | Aebischer et al. | |
| 5,500,362 A | 3/1996 | Robinson et al. | |
| 5,532,152 A | 7/1996 | Cousens et al. | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,567,610 A | 10/1996 | Borrebaeck et al. | |
| 5,569,825 A | 10/1996 | Lonberg et al. | |
| 5,571,894 A | 11/1996 | Wels et al. | |
| 5,573,905 A | 11/1996 | Lerner et al. | |
| 5,587,458 A | 12/1996 | King et al. | |
| 5,591,669 A | 1/1997 | Krimpenfort et al. | |
| 5,605,801 A | 2/1997 | Cousens et al. | |
| 5,641,669 A | 6/1997 | Cousens et al. | |
| 5,641,870 A | 6/1997 | Rinderknecht et al. | |
| 5,648,237 A | 7/1997 | Carter | |
| 5,656,431 A | 8/1997 | Cousens et al. | |
| 5,698,403 A | 12/1997 | Cousens et al. | |
| 5,731,168 A | 3/1998 | Carter et al. | |
| 5,739,277 A | 4/1998 | Presta et al. | |
| 5,789,199 A | 8/1998 | Joly et al. | |
| 5,821,337 A | 10/1998 | Carter et al. | |
| 5,837,234 A | 11/1998 | Gentile et al. | |

(Continued)

FOREIGN PATENT DOCUMENTS

| | | |
|---|---|---|
| EP | 0183070 | 6/1986 |
| EP | 0203089 | 12/1986 |

(Continued)

OTHER PUBLICATIONS (MAST-E) The Multicenter Acute Stroke Trial-Europe; Thrombolytic therapy with streptokinase in acute ischemic stroke ; N Engl J Med; 335(3): 145-50; Jul. 18, 1996.
(NINDS) The National Institute of Neurological Disorders; Tissue plasminogen activator for acute ischemic stroke. (rt-PA Stroke Trial); N Engl J. Med; 333(24): 1581-7; Dec. 14, 1995.
Ackermann et al.; Ca(2+))-independent cytosolic phospholipase A2 from macrophage-like P388D1 cells. Isolation and characterization; J. Biol. Chem; 269(12); pp. 9227-9233; Mar. 25, 1994.
Akiyama et al.; Determination of platelet-activating factor acetylhydrolase activity by blotting, beta-radioluminescence, and ultrahigh-sensitivity television camera detection; Analytical Biochemistry; 218 (2):295-299; May 1, 1994.

(Continued)

*Primary Examiner* — Bin Shen
(74) *Attorney, Agent, or Firm* — Loretta J. Sauermelch; Edward R. Gimmi

(57) ABSTRACT

This invention relates to methods for determining the activity of Lp-PLA2 in at least one sample from an animal. The invention also relates to methods for determining the inhibition of Lp-PLA2 activity in samples from animals that are administered an Lp-PLA2 inhibitor.

23 Claims, 24 Drawing Sheets

(56) References Cited

U.S. PATENT DOCUMENTS

| | | |
|---|---|---|
| 5,840,523 A | 11/1998 | Simmons et al. |
| 5,847,088 A | 12/1998 | Cousens et al. |
| 5,869,046 A | 2/1999 | Presta et al. |
| 5,880,273 A | 3/1999 | Adachi et al. |
| 5,977,308 A | 11/1999 | Cousens et al. |
| 5,981,252 A | 11/1999 | MacPhee et al. |
| 6,177,257 B1 | 1/2001 | MacPhee et al. |
| 6,203,790 B1 | 3/2001 | Cousens et al. |
| 6,596,544 B1 | 7/2003 | Fogelman et al. |
| 7,052,862 B2 | 5/2006 | MacPhee et al. |
| 7,217,535 B2 | 5/2007 | MacPhee et al. |
| 7,301,043 B2 | 11/2007 | Deigner et al. |
| 7,416,853 B2 | 8/2008 | MacPhee et al. |
| 7,531,316 B2 | 5/2009 | Hu et al. |
| 7,741,020 B2 | 6/2010 | Shou et al. |
| 8,088,886 B2 | 1/2012 | MacPhee et al. |
| 8,575,348 B2 | 11/2013 | Rao et al. |
| 8,609,357 B2 | 12/2013 | Shou et al. |
| 8,637,524 B2 | 1/2014 | Rao et al. |
| 8,846,309 B2 | 9/2014 | Shou et al. |
| 9,000,132 B2 | 4/2015 | Miller et al. |
| 2002/0102231 A1 | 8/2002 | Dietsch et al. |
| 2003/0072747 A1 | 4/2003 | Cousens et al. |
| 2003/0148398 A1 | 8/2003 | MacPhee et al. |
| 2005/0064532 A1 | 3/2005 | Deigner et al. |
| 2007/0166777 A1 | 7/2007 | Shou et al. |
| 2007/0281323 A1 | 12/2007 | Wolfert et al. |
| 2008/0280829 A1 | 11/2008 | Shi et al. |
| 2010/0248259 A1 | 9/2010 | Hess et al. |
| 2011/0039284 A1 | 2/2011 | Breit et al. |
| 2011/0280829 A1 | 11/2011 | David et al. |
| 2012/0309697 A1 | 12/2012 | Breit et al. |
| 2014/0283157 A1 | 9/2014 | Miller et al. |
| 2015/0160229 A1 | 6/2015 | Schaal et al. |

FOREIGN PATENT DOCUMENTS

| | | |
|---|---|---|
| EP | 0244234 | 11/1987 |
| EP | 0402226 | 12/1990 |
| EP | 0404097 A2 | 12/1990 |
| EP | 0658205 A1 | 6/1995 |
| EP | 0673426 A1 | 9/1995 |
| EP | 0816504 A2 | 1/1998 |
| EP | 0658205 B1 | 3/2000 |
| EP | 0673426 B1 | 6/2001 |
| EP | 1318154 A1 | 6/2003 |
| EP | 1718967 A2 | 11/2006 |
| EP | 1735457 A2 | 12/2006 |
| EP | 2253702 A1 | 11/2010 |
| EP | 2290094 A1 | 3/2011 |
| JP | 4346797 | 12/1992 |
| JP | 6116279 A | 4/1994 |
| JP | 7059597 A | 3/1995 |
| JP | 3036883 B2 | 4/2000 |
| JP | 2002179545 | 6/2002 |
| JP | 2002223794 A | 8/2002 |
| JP | 2004018501 | 1/2004 |
| JP | 4220603 B2 | 2/2009 |
| KR | 10-11411189 B1 | 5/2012 |
| WO | WO81/01145 A1 | 4/1981 |
| WO | WO87/00195 A1 | 1/1987 |
| WO | WO88/07378 A1 | 10/1988 |
| WO | WO90/03430 A1 | 4/1990 |
| WO | WO91/00360 A1 | 1/1991 |
| WO | WO92/20373 A1 | 11/1992 |
| WO | WO93/08829 A1 | 5/1993 |
| WO | WO93/11161 A1 | 6/1993 |
| WO | WO93/16185 A2 | 8/1993 |
| WO | WO93/25673 A1 | 12/1993 |
| WO | WO94/04690 A1 | 3/1994 |
| WO | WO95/09921 A1 | 4/1995 |
| WO | WO96/07321 A1 | 3/1996 |
| WO | WO96/16673 A1 | 6/1996 |
| WO | WO97/38731 A1 | 10/1997 |
| WO | WO98/02463 A1 | 1/1998 |
| WO | WO00/24910 A1 | 5/2000 |
| WO | WO00/32808 A1 | 6/2000 |
| WO | WO00/66567 A1 | 11/2000 |
| WO | WO01/60805 A1 | 8/2001 |
| WO | WO02/30904 A1 | 4/2002 |
| WO | WO02/30911 A1 | 4/2002 |
| WO | WO03/041712 A1 | 5/2003 |
| WO | WO03/086400 A1 | 10/2003 |
| WO | WO03/087088 A2 | 10/2003 |
| WO | WO2004/089184 A2 | 10/2004 |
| WO | WO2005/001416 A2 | 1/2005 |
| WO | WO2005/074604 A2 | 8/2005 |
| WO | WO2005/113797 A2 | 12/2005 |
| WO | WO2009/098656 A2 | 8/2009 |
| WO | WO2011/137419 A1 | 11/2011 |
| WO | WO2013/078253 A1 | 5/2013 |

OTHER PUBLICATIONS

Akiyama et al.; Identification of a Major PAF Acetylhydrolase in Human Serum/Plasma as a 43 kDa Glycoprotein Containing about 9 kDa Asparagine-Conjugated Sugar Chain(s); Journal of Biochemistry; 123(5):786-789; May 1998.

Akiyama et al.; New Serum PAF acetylhydrolase detection method used with the Blotting Method and Beta of 3Hacetyl-PAF; Proceedings of Japanese Conference on the Biochemistry of Lipids; 36:43-46; (year of publication is sufficiently earlier than the effective U.S. filing date and any foreign priority date) 1994; English abstract.

Albert et al.; The effect of statin therapy on lipoprotein associated phospholipase A2 levels; Atherosclerosis; 182(1):193-198; Sep. 2005.

Alberts et al.; Risk of Stroke and Elevated Levels of Lipoprotein-Associated Phospholipase A2, Abstracts From the 2008 International Stroke Conference; Stroke; 39(2):642; Feb. 2008.

Anderson; Human gene therapy; Science; 256(5058):808-813; May 8, 1992.

Arkin et al.; Inhibition of Protein Interaction: Non-Cellular Assay Formats; Assay Guidance Manual; 26 pages; Mar. 2012.

Artsaenko et al.; Expression of a single-chain Fv antibody against abscisic acid creates a witty phenotype in transgenic tobacco; Plant J; 8(5):745-50; Nov. 1995.

Asano et al; Cellular source(s) of platelet-activating-factor acetylhydrolase activity in plasma; Biochem. Biophsys. Res. Commun.; 261(2); pp. 511-514; Aug. 2, 1999.

Atmeh et al.; Albumin Aggregates: Hydrodynamic shape and physico-chemical properties; Jordan Journal of Chemistry; 2(2); pp. 169-182; Jul. 29, 2007.

Attri et al.; Self-association of Zn-insulin at neutral pH: investigation by concentration gradient static and dynamic light scattering; Biophys. Chem.; 148(1-3); pp. 23-27; May 2010.

Balafa et al.; Urine of Patients with Nephrotic Syndrome Contains the Plasma Type of PAF-Acetylhydrolase Associated with Lipoproteins; Nephron Physiology; 97(3):45-52; (year of publication is sufficiently earlier than the effective U.S. filing date and any foreign priority date) 2004.

Balestrieri et al.; Measurement of Platelet-Activating Factor Acetylhydrolase Activity by Quantitative High-Performance Liquid Chromatography Determination of Courmarin-Derivatized 1-0-alkyl-2-sn-lysoglyceryl-3-phosphorylcholine; Analytical Biochemistry; 233(2): 145-50; Jan. 1996.

Ballantyne et al.; Lipoprotein-associated phospholipase A2, high-sensitivity C-reactive protein, and risk for incident coronary heart disease in middle-aged men and women in the Atherosclerosis Risk in Communities (ARIC) study; Circulation; 109:837-42; Feb. 2004.

Ballantyne et al.; Lipoprotein-associated phospholipase A2, high-sensitivity C-reactive protein, and risk for incident ischemic stroke in middle-aged men and women in the Atherosclerosis Risk in Communities (ARIC) study; Arch Intern Med.; 165(21):2479-84; Nov. 28, 2005.

Barnes et al.; Methods for growth of cultured cells in serum-free medium; Anal Biochem; 102(2):255-270; Mar. 1, 1980.

(56) References Cited

OTHER PUBLICATIONS

Bell et al.; Systematic Screening of the LDL-PLA2Gene for Polymorphic Variants and Case-Control Analysis in Schizophrenia; Biochem and Biophys Res Commun.; 241(3):630-635; Dec. 29, 1997.

Bhairi; A guide to the properties and uses of detergents in biology and biochemistry; Calbiochem-Novobio-chem Corporation, San Diego; ©2001; 43 pgs.; Aug. 13, 2014; retrieved from the internet (http://wolfson.huji.ac.il/purification/PDF/detergents/calbiochem detergents.pdf).

BISC 429; BISC 429: Experimental Techniques II Separation Methods. Acid Phosphatase-Enzyme Assay; Siman Fraser University available at www.sfu.ca/bisc/bisc-429/enzymeassay.html#intro, including Image if Google search showing that the document as been available since Jan. 31, 2002.

Blackie et al.; The identification of clinical candidate SB-480848: a potent inhibitor of lipoprotein-associated phospholipase A2; Bioorg Med Chem Lett.; 13(6):1067-1070; Mar. 23, 2003.

Blake et al.; A prospective evaluation of lipoprotein-associated phospholipase A(2) levels and the risk of future cardiovascular events in women; J Am Coll Cardiol.; 1;38(5):1302-1306; Nov. 2001.

Blake et al.; Inflammatory bio-markers and cardiovascular risk prediction; J Intern Med; 252(4):283-94; Oct. 2002.

Blankenberg et al.; Plasma PAF-acetylhydrolase in patients with coronary artery disease: results of a cross-sectional analysis; J Lipid Res; 44(7):1381-6; Jul. 2003.

Bloomer et al.; 1-(Arylpiperazinylamidoalkyl)-pyrimidones: orally active inhibitors of lipoprotein-associated phospholipase A(2); Bioorg Med Chem Lett.; 11(14):1925-1929; Jul. 23, 2001.

Boyd et al.; 2-(Alkylthio)pyrimidin-4-ones as novel, reversible inhibitors of lipoprotein-associated phospholipase A2; Bioorg Med Chem Lett; 10(4):395-398; Feb. 21, 2000.

Boyd et al.; N-1 Substituted Pyrimidin-4-Ones: Novel, Orally Active Inhibitors of Lipoprotein-Associated Phospholipase A2; Bioorg Med Chem Lett; 10(22):2557-2561; Nov. 20, 2000.

Boyd et al.; Potent, orally active inhibitors of lipoprotein-associated phospholipase A(2): 1-(biphenylmethylamidoalkyl)-pyrimidones; Bioorg Med Chem Lett.; 12(1):51-55; Jan. 7, 2002.

Boyd et al.; The identification of a potent, water soluble inhibitor of lipoprotein-associated phospholipase A2; Bioorg Med Chem Lett.; 11(5):701-704; Mar. 12, 2001.

Bravata et al.; Thrombolysis for acute stroke in routine clinical practice; Arch Intern Med; 162(17):1994-2001; Sep. 23, 2002.

Brennan et al.; Preparation of bispecific antibodies by chemical recombination of monoclonal immunoglobulin G1 fragments; Science; 229(4708):81-83; Jul. 5, 1985.

Brilakis et al.; Influence of race and sex on lipoprotein-associated phospholipase A2 levels: observations from the dallas heart study; Atherosclerosis; 199(1); pp. 110-115; Jul. 2008.

Brites et al.; Paraoxonase 1 and Platelet-Activating Factor Acetylhydrolase Activities in Patients with Low HDL-Cholesterol Levels with or without Primary Hypertriglyceridemia; Archives of Medical Research; 35(3):235-240; May-Jun. 2004.

Brodeur et al.; (Chap. 4) Mouse-human myeloma partners for the production of heterohybridomas; in Monoclonal Antibody Production Techniques and Applications; Marcel Dekker, Inc., New York; pp. 51-63; 1987 (year of pub. sufficiently earlier than effective US filing date and any foreign priority date).

Brüggemann et al.; Designer mice: the production of human antibody repertoires in transgenic animals; Year Immunol; 7:33-40; Feb. 1993.

Burke; Phospholipase A2 biochemistry; Cardiovas. Drugs Ther.; 23(1); pp. 49-59; Feb. 2009.

Busby et al.; SB-253514 and analogues: novel inhibitors of lipoprotein associated phospholipase A2 produced by *Pseudomonas fluorescens* DSM 11579. II. Physico-chemical properties and structure elucidation; J Antibiot; 53 (7):670-6; Jul. 2000.

Cao et al; Lipoprotein-associated phospholipase A2 interacts with phospholipid vesicles via a surface-disposed hydrophobic alpha-helix; Biochemistry; 50(23); pp. 5314-5321; Jun. 14, 2011.

Capel et al.; Heterogeneity of human IgG Fc receptors; Immunomethods; 4(1):25-34; Feb. 1994.

Caron et al.; Engineered humanized dimeric forms of IgG are more effective antibodies; J Exp Med; 176(4):1191-5; Oct. 1, 1992.

Carpenter et al.; Inhibition of lipoprotein-associated phospholipase A2 diminishes the death-inducing effects of oxidised LDL on human monocyte-macrophages; FEBS Lett.; 505(3):357-63; Sep. 21, 2001.

Carter et al.; High level *Escherichia coli* expression and production of a bivalent humanized antibody fragment; Biotechnology; 10(2):163-167; Feb. 1992.

Carter et al.; Humanization of an anti-p185HER2 antibody for human cancer therapy; Proc Natl Acad Sci USA; 89(10):4285-9; May 15, 1992.

Casas et al.; PLA2G7 genotype, lipoprotein-associated phospholipase A2 activity, and coronary heart disease risk in 10 494 cases and 15 624 controls of European Ancestry; Circulation; 121(21):2284-93; Jun. 1, 2010.

Caslake et al.; Lipoprotein-associated Phospholipase A2 platelet-activating factor acetylhydrolase: a potential new risk factor for coronary artery disease; Atherosclerosis; 150(2): 413-9; Jun. 2000.

Cayman Chemical, Ann Arbor, MI; PAF Acetylhydrolase Assay Kit; Catalog No. 760901; Cayman Chemical Company, Ann Harbor, MI; Jun. 22, 2005.

Chari et al.; Immunoconjugates containing novel maytansinoids: promising anticancer drugs; Cancer Res; 52(1):127-31; Jan. 1, 1992.

Chothia et al.; Canonical structures for the hypervariable regions of immunoglobulins; J Mol Biol; 196(4):901-917; Aug. 20, 1987.

Chothia et al.; Structural determinants in the sequences of immunoglobulin variable domain; J Mol Biol; 278(2):457-479; May 1, 1998.

Chothia et al.; Structural repertoire of the human VH segments; J Mol Biol; 227(3):799-817; Oct. 5, 1992.

Clackson et al.; Making antibody fragments using phage display libraries; Nature; 352(6336):624-628; Aug. 15, 1991.

Clark et al.; Recombinant tissue-type plasminogen activator (Alteplase) for ischemic stroke 3 to 5 hours after symptom onset; The Atlantis Study: A randomized controlled trial. Alteplase Thrombolysis for Acute Noninterventional Therapy in Ischemic Stroke' JAMA; 282(21):2019-2026; Dec. 1, 1999.

Clynes et al.; Fc receptors are required in passive and active immunity to melanoma; Proc Natl Acad Sci USA; 95(2):652-6; Jan. 20, 1998.

Cook et al.; Clinical utility of lipoprotein-associated phospholipase A2 for cardiovascular disease prediction in a multiethnic cohort of women; Clin. Chem.; 58(9); pp. 1352-1363; Sep. 2012.

Cucchiara et al.; Lipoprotein-associated phospholipase A2 and C-reactive protein for risk-stratification of patients with TIA; Stroke; 40(7):2332-6.; Jul. 2009.

Cunningham et al.; High-resolution epitope mapping of hGH-receptor interactions by alanine-scanning mutagenesis; Science; 244(4908):1081-1085; Jun. 2, 1989.

Dada et al; LP-PLA2: an emerging biomarker of coronary heart disease; Expert Review of Molecular Diagnostics; 2(1): 17-22; Jan. 2002.

Daeron; Fc receptor biology; Annu Rev Immunol; 15:203-234; Apr. 1997.

Davies; The pathophysiology of acute coronary syndromes; Heart; 83:361-6; Mar. 2000.

De Haas et al.; Fc gamma receptors of phagocytes; J Lab Clin Med; 126 (4):330-341; Oct. 1995.

Deigner et al.; Novel reversible, irreversible and fluorescent inhibitors of plateletactivating factor acetylhydrolase as mechanistic probes; Atherosclerosis; 144(1):79-90; May 1999.

Diadexus Inc.; Enzyme Immunoassay for the Quantitative Determination of Lp-PLA2 in Human Plasma and Serum; Aug. 2005.

Donnan et al.; Streptokinase for acute ischemic stroke with relationship to time of administration; Australian Streptokinase (ASK) Trial Study Group, JAMA. 276(12):961-966; Sep. 25, 1996.

(56) References Cited

OTHER PUBLICATIONS

Eaton; Cholesterol testing and management: a national comparison of family physicians, general internists, and cardiologists; J Am Board Fam Pract; 11(3):180-6; May-Jun. 1998.
Eckel et al.; 2013 AHA/ACC guideline on lifestyle management to reduce cardiovascular risk: a report of the american college of cardiology/american heart association task force on practice guidelines; Circulation; 129(25 Suppl 2); S100-101; Jun. 24, 2014.
Elkind et al.; High-sensitivity C-reactive protein, lipoprotein-associated phospholipase A2, and outcome after ischemic stroke; Arch Intern Med; 166(19):2073-80; Oct. 23, 2006.
Eppstein et al.; Biological activity of liposome-encapsulated murine interferon gamma is mediated by a cell membrane receptor; Proc Natl Acad Sci USA; 82(11):3688-92; Jun. 1985.
Evan et al.; Isolation of monoclonal antibodies specific for human c-myc proto-oncogene product; Mol Cell Biol; 5(12):3610-6; Dec. 1985.
Expert Panel on Detection, Evaluation, and Treatment of High Blood Cholesterol in Adults; Executive Summary of The Third Report of The National Cholesterol Education Program (NCEP) Expert Panel on Detection, Evaluation, and Treatment of High Blood Cholesterol in Adults (Adult Treatment Panel III); JAMA; 285(19):2486-2497; May 16, 2001.
Fecker et al.; Expression of single-chain antibody fragments (scFv) specific for beet necrotic yellow vein virus coat protein or 25 kDa protein in *Escherichia coli* and *Nicotiana benthamiana*; Plant Mol Biol; 32(5):979-986; Dec. 1996.
Ferrer et al.; The conformation of serum albumin in solution: a combined phosphorescence depolarization-hydrodynamic modeling; Biophys. J.; 80(5); pp. 2422-2430; May 2001.
Field et al.; Purification of a RAS-responsive adenylyl cyclase complex from *Saccharomyces cerevisiae* by use of an epitope addition method; Mol Cell Biol; 8(5):2159-65; May 1988.
Flegar-Mestric et al.; Serum platelet-activating factor acetylhydriolase activity in patients with angiographically established cerebrovascular stenosis; Clinical Chemistry and Laboratory Medicine; Proceesing of the IFFCC-FESCC European Congress; 15'h Barcelona, Spain: 369-372; Publisher Monduzzi Editore, Bologna, Italy; Jun. 1-5, 2003 (Abstract only).
Fraker et al.; Protein and cell membrane iodinations with a sparingly soluble chloroamide, 1,3,4,6-tetrachloro-3a,6a-diphrenylglycoluril; Biochem Biophys Res Commun; 80:849-857; Feb. 28, 1978.
Fujimura et al.; Serum platelet-activating factor acetylhydrolase activity in rats with gastric ulcers induced by water-immersion stress; Scand J Gastroenterol Suppl.; 24(162):59-62; (year of publication is sufficiently earlier than the effective U.S. filing date and any foreign priority date) 1989.
Furie et al.; Lipoprotein-associated phospholipase A2 activity predicts early stroke recurrence [abstract]; Stroke; 38(2):458; Feb. 2007.
Furukawa et al.; Platelet-Activating FactorRlnduced Ischemic Bowel Necrosis: The Effect of Platelet-Activating Factor Acetylhydrolase; Pediatr Res.; 34(2):237-41; Aug. 1993.
Gabizon et al.; Pharmacokinetics and tissue distribution of doxorubicin encapsulated in stable liposomes with long circulation times; J Natl Cancer Inst; 81(19):1484-1488; Oct. 4, 1989.
Gardner et al.; Identification of a domain that mediates association of platelet-activating factor acetylhydrolase with high density lipoprotein; J. Biol. Chem.; 283(25); pp. 17099-17106; Jun. 20, 2008.
Gazzano-Santoro et al.; A non-radioactive complement-dependent cytotoxicity assay for anti-CD20 monoclonal antibody; J Immunol Methods; 202(2):163-171; Mar. 28, 1997.
Gelman et al.; Poststratification and weighting adjustments; 2000; 2 pgs.; retrieved from the internet on Dec. 11, 2014; (http://citeseerx.ist.psu.edu/viewdoc/summary?doi=10.1.1.38.5290) Abstract Only.
Gerber et al.; Plasma lipoprotein-associated phospholipase A2 levels in heart failure: association with mortality in the community; Atherosclerosis; 203(2); pp. 593-598; Apr. 2009.
Glass et al.; Atherosclerosis: The road ahead; Cell; 104:503-16; Feb. 23, 2001.

Go et al.; Heart diease and stroke statistics—2014 update: a report from the american heart association; Circulation; 129(3); pp. e28-e292; Jan. 21, 2014.
Goding; Monoclonal Antibodies: Principles and Practice; Academic Press; pp. 103; 1986 (year of pub. sufficiently earlier than effective US filling date and any foreign priority date).
Goff et al.; 2013 ACC/AHA guideline on the assessment of cardiovascular risk: a report of the american college of cardiology/american heart association task force on practice guidelines; Circulation; 129(25 Suppl 2); pp. S49-S73; Jun. 24, 2014.
Goodman et al.; (Chap. 6) Immunoglobulin Proteins; in Stites et al. (eds.); Basic and Clinical Immunology, 8th Ed.; Appleton & Lange, Norwalk, CT.; pp. 66-79; Jan. 1, 1994.
Gorelick; Lipoprotein-associated phospholipase A2 and risk of stroke; Am J Cardiol; 101(12A):34F-40F; Jun. 16, 2008.
Graham et al.; Characteristics of a human cell line transformed by DNA from human adenovirus type 5; J Gen Virol; 36(1):59-72; Jul. 1977.
Grallert et al.; Eight genetic loci associated with variation in lipoprotein-associated phospholipase A2 mass and activity and coronary heart disease: meta-analysis of genome-wide association studies from five community-based studies; Eur Heart J; 33(2):238-51.; Jan. 2012.
Griffiths et al.; Human anti-self antibodies with high specificity from phage display libraries; EMBO J.; 12(2):725-34; Feb. 1993.
Grissom et al.; Platelet-activating factor acetylhydrolase is increased in lung lavage fluid from patients with acute respiratory distress syndrome; Critical Care Medicine; 31(3):770-775, Mar. 2003.
Gruber et al.; Efficient tumor cell lysis mediated by a bispecific single chain antibody expressed in *Escherichia coli*; J Immunol; 152(11):5368-5374; Jun. 1, 1994.
Guss et al.; Structure of the IgG-binding regions of streptococcal protein; G EMBO J; 5(7):1567-75; Jul. 1986.
Guyer et al.; Immunoglobulin binding by mouse intestinal epithelial cell receptors; J Immunol; 117(2):587-593; Aug. 1976.
Hacke et al.; Intravenous thrombolysis with recombinant tissue plasminogen activator for acute hemispheric stroke; The European Cooperative Acute Stroke Study (ECASS), JAMA; 274(13):1017-1025; Oct. 4, 1995.
Hacke et al.; Randomised double-blind placebo-controlled trial of thrombolytic therapy with intravenous alteplase in acute ischaemic stroke (ECASS II); Lancet; 352(9136):1245-1251; Oct. 17, 1998.
Hakkinen et al.; Lipoprotein-associated phospholipase A(2), platelet-activating factor acetylhydrolase, is expressed by macrophages in human and rabbit atherosclerotic lesions; Arterioscler Thromb Vasc Biol; 19(12):2909-17; Dec. 1999.
Ham et al.; Media and growth requirements; Methods Enzymol; 58:44-93; 1979 (year of pub. sufficiently earlier than effective US filing date and any foreign priority date).
Hatoum et al.; Dietary, lifestyle, and clinical predictors of lipoprotein-associated phospholipase A2; activity in individuals without coronary artery disease; Am. J. Clin. Nutr.; 91(3); pp. 786-793; Mar. 2010.
Heart Protection Study Group; Lipoprotein-associated phoslipase A2 activity and mass in relation to vascular disease and nonvascular mortality; J. Intern. Med.; 268; pp. 348-358; Oct. 2010.
Hemmings et al.; Platelet-Activating Factor Acetylhydrolase Activity in Peritoneal Fluids of Women with Endometriosis; Obstetrics and Gynecology; 81(2):276-279; Feb. 1993.
Henderson et al.; Recombinant Human Platelet-Activating Factor—Acetylhydrolase Inhibits Airway Inflammation and Hyperreactivity in Mouse Asthma Model; J Immunol; 164(6):3360-3367; Mar. 15, 2000.
Hendrickson et al.; Intramolecularly Quenched BODIPY—Labeled Phospholipids Analogs in Phospholipase A2 and Platelet-Activating Factor Acetylhydrolase assays and in Vivo Fluorescence Imaging; Analytical Biochemistry; 276(1):27-35; Dec. 1999.
Heron; Deaths: Leading Causes for 2004; Nat'l Vital Stat Rep; 56(5):1-95; Nov. 20, 2007.
Herrmann et al.; Expression of lipoprotein-associated phospholipase A(2) in carotid artery plaques predicts long-term cardiac outcome; Eur Heart J; 30(23):2930-8; Dec. 2009.

(56) References Cited

OTHER PUBLICATIONS

Hiatt et al.; Production of antibodies in transgenic plants; Nature; 342 (6245):76-78; Nov. 2, 1989.
Hiramoto et al.; A mutation in plasma platelet-activating factor acetylhydrolase (Val279—>Phe) is a genetic risk factor for stroke; Stroke; 28(12):2417-20; Dec. 1997.
Hoffman et al.; Genetic variants and haplotypes of lipoprotein associated phospholipase A2 and their influence on cardiovascular disease (The Ludwigshafen Risk and Cardiovascular Health Study); J Thromb Haemost; 7(1):41-8; Jan. 2009.
Holliger et al.; Diabodies: small bivalent and bispecific antibody fragments; Proc Natl Acad Sci USA; 90(14):6444-8; Jul. 15, 1993.
Hopp et al.; A Short Polypeptide Marker Sequence Useful for Recombinant Protein Identification and Purification; Nature Biotechnology; 6:1204-1210; Oct. 1988.
Hwang et al.; Hepatic uptake and degradation of unilamellar sphingomyelin/cholesterol liposomes: a kinetic study; Proc Natl Acad Sci USA; 77(7):4030-4; Jul. 1980.
Ibe et al.; Platelet Activating Factor Acetylhydrolase Activity in Lamb Lungs is Up-Regulated in the Immediate Newborn Period; Molecular Genetics and Metabolism; 69(1):46-55; Jan. 2000.
Imaizumi et al.; Activity of platelet-activating factor (PAF) acetylhydrolase in plasma from healthy habitual cigarette smokers; Heart and Vessels; 5(2):81-86; (year of publication is sufficiently earlier than the effective U.S. filing date and any foreign priority date) 1990.
Ito et al.; Serum PAF-Acetylhydrolase (PAF-AH) in Hepatobiliary Disease; Japanese Pharmacology and Therapeutics; 30/Suppl. 2; (year of publication is sufficiently earlier than the effective U.S. filing date And any foreign priority date) 2002.
Izake et al.; Platelet-activating factor and arachidonic acid metabolites in psoriatic inflammation; Br J Dermatol.; 134(6):1060-4; Jun. 1996.
Jaaskelainen et al.; Conformational change in the activation of lipase: an analysis in terms of low-frequency normal modes; Protein Sci.; 7(6); pp. 1359-1367; Jun. 7, 1998.
Jakobovits et al.; Analysis of homozygous mutant chimeric mice: deletion of the immunoglobulin heavy-chain joining region blocks B-cell development and antibody production; Proc Nati Acad Sci Usa; 90(6):2551-5; Mar. 15, 1993.
Jakobovits et al.; Germ-line transmission and expression of a human-derived yeast artificial chromosome; Nature; 362(6417):255-258; Mar. 18, 1993.
Janeway et al.; Immunobiology: the Immune System in Health and Disease; Garland Publishing; New York, NY; 3d Ed.; pp. 3.1-3.11; (year of publication is sufficiently earlier than the effective U.S. filing date and any foreign priority date) 1997.
Johnson et al.; Human antibody engineering; Curr Opin Struct Biol; 3 (4):564-571; Aug. 1993.
Jones et al.; Replacing the complementarity-determining regions in a human antibody with those from a mouse; Nature; 1321(6069):522-525; May 1986.
Karabina et al; Increased activity of plate-activating factor acetylhydrolase in low-density lipoprotein subfractions induces enhanced lysophosphatidylcholine production during oxidation in patients with heterozygous familial hypercholesterolaemia; Eur. J. Clin. Invest; 27(7); pp. 595-602; Jul. 1997.
Karkabounas et al.; Quantitative Fluorescence Determination of Phospholipase A2 and PAF Acetylhydrolase in Biological Fluids using High Performance Liquid Chromatography; Chemistry and Physics of Lipids; 130(1):69-70; Jun. 2004.
Karlan Research Products Corporation, Santa Rosa, CA; Auto PAF-AH Serum (plasma) platelet-activating factor (PAF) acetylhydrolase assay—Instruction Manual; (date of publication unknown; available to applicants at least as of Sep. 16, 2005).
Katzan et al.; Use of tissue-type plasminogen activator for acute ischemic stroke: The Cleveland area experience; JAMA; 283(9):1151-8; Mar. 1, 2000.
Kawamura, Y.; A Simple Measurement of Plasma Platelet-Activating Factor (PAF) Acetylhydrolase, Normal Level Activity, and Distribution Among Lipoprotein Fractions; Japanese Journal of Clincal Pathology; 35(10):1149-1153; Oct. 1987.
Kearney et al.; A new mouse myeloma cell line that has lost immunoglobulin expression but permits the construction of antibody-secreting hybrid cell lines; J Immunol; 123(4):1548-1550; Oct. 1979.
Khovidhunkit et al.; Plasma platelet-activating factor acetylhydrolase activity in human immunodeficiency virus infection and the acquired immunodeficiency syndrome; Metabolism.; 48 (12):1524-31; Dec. 1999.
Kirschbaum B.; Platelet Activating Factor Acetylhydrolase activity in the urine of patients with renal disease; Clinical Chimica Acta; 199(2):139-146; Jun. 14, 1991.
Kitsiouli et al.; Differential Determination of Phospholipase A2 ane P AFAcetylhydrolase in Biological Fluids Using Fluorescent Substrates; Journal of Lipid Research; 40(12):2346-2356; Dec. 1999.
Koenig et al.; Lipoprotein-Associated Phospholipase A2 Adds to Risk Prediction of Incident Coronary Events by C-Reactive Protein in Apparently Healthy Middle-Aged Men from the General Population; Circulation; 110 (14):1903-1908; Oct. 2004.
Köhler et al.; Continuous cultures of fused cells secreting antibody of predefined specificity; Nature; 256(5517):495-497; Aug. 7, 1975.
Kolodgie et al.; Lipoprotein-associated phospholipase A2 protein expression in the natural progrssion of human coronary atherosclerosis; Aeterioscler Thromb. Vasc. Biol.; 26(11); pp. 2523-2529; Nov. 2006.
Kosaka et al.; Serum platelet-activating factor acetylhydrolasse (PAF-AH) activity in more than 3000 healthy Japanese; Clinica Chimica Acta; 312(1-2):179-183; Oct. 2001.
Kosaka et al.; Spectrophotometric Assay for Serum Platelet-Activating Factor Acetylhydrolase Activity; Clinica Chimica Acta; 296(1-2):151-161; Jun. 2000.
Kostelny et al.; Formation of a bispecific antibody by the use of leucine zippers; J Immunol; 148(5):1547-1553; Mar. 1, 1992.
Kozbor et al.; A human hybrid myeloma for production of human monoclonal antibodies; J Immunol; 133(6):3001-3005; Dec. 1984.
Kruse et al.; The lle198Thr and Ala379Val variants of plasmatic PAF-acetylhydrolase impair catalytical activities and are associated with atopy and asthma; Am J Hum Genet; 66(5):1522-30; May 2000.
Kujiraoka et al.; Altered Distribution of Plasma PAF-AH between HDLs and other Lipoproteins in Hyperlipidemia and Diabetes Mellitus; Journal of Lipid Research; 44(10):2006-14; Oct. 2003.
Kuvin at al.; Effects of extended-release niacin on lipoprotein particle size, distribution, and inflammatory markers in patients with coronary artery disease; Am J Cardiol.; 98(6):743-745; Sep. 15, 2006.
Lanman et al.; Lipoprotein-associated phospholipase A2; review and reccommendation of a clinical cut point for adults; Preventive Cardiology; 9(3); pp. 138-143; Summer 2006 (year of pub. sufficiently earlier than effective US filing date and any foreign priority date).
Leach et al.; Lipoprotein-associated PLA2 inhibition—a novel, non-lipid lowering strategy for atherosclerosis therapy; Farmaco.; 56(1-2):45-50; Jan.-Feb. 2001.
Libby et al.; Macrophages and atherosclerotic plaque stability; Curr Opin Lipidol.; 7(5):330-335; Oct. 1996.
Lindahl et al.; Markers of myocardial damage and inflammation in relation to long-term mortality in unstable coronary artery disease. FRISC Study Group. Fragmin during Instability in Coronary Artery Disease; N Engl J Med; 343 (16):1139-47; Oct. 19, 2000.
Lindmark et al.; Binding of immunoglobulins to protein A and immunoglobulin levels in mammalian sera; J Immunol Methods; 62(1):1-13; Aug. 12, 1983.
Lorber et al.; Purification of octyl-beta-D-glucopyranoside and re-estimation of its micellar size; Biochimica et Biophysica Acta (BBA)- Biomembranes; 1023(2); pp. 254-265; Apr. 13, 1990.
Luepker et al.; Case definitions for acute coronary heart disease in epidemiology and clinical research studies: a statement from the AHA council on epidemiology and prevention: AHA statistics committee; world heart federation council on epidemiology and prevention; the european society of cardiology working on epidemiology and prevention; centers for dieseaase control and preven-

(56) References Cited

OTHER PUBLICATIONS tion; and the national heart, lung, and blood institute; Circulation; 108(20); pp. 2543-2549; Nov. 18, 2003.
Lund_Katz et al.; High density lipoprotein structure-function and role in reverse cholesterol transport; Subcell Biochem.; 51; pp. 183-227; Nov. 14, 2010.
Lusis; Atherosclerosis; Nature; 407(6801):233-41; Sep. 14, 2000 (Author Manuscript).
Lutz-Freyermuth et al.; Quantitative determination that one of two potential RNA-binding domains of the A protein component of the U1 small nuclear ribonucleoprotein complex binds with high affinity to stem-loop II of U1 RNA; Proc Natl Acad Sci USA; 87(16):6393-7; Aug. 1990.
MacPhee et al.; Lipoprotein-associated phospholipase A2, platelet-activating factor acetylhydrolase, generates two bioactive products during the oxidation of low-density lipoprotein: use of a novel inhibitor; Biochem J; 338:479-87; Mar. 1, 1999.
MacPhee; Lipoprotein-associated phospholipase A2: a potential new risk factor for coronary artery disease and a therapeutic target; Curr Opin Pharmaco;. 1(2):121-125; Apr. 2001.
Mannuzza et al.; Is bovine albumin too complex to be just a commodity? Part One: Manufacturing and implications; Bioprocess International; 8(2); pp. 40-42; Feb. 2010.
Mannuzza et al.; Is bovine albumin too complex to be just a commodity? Part two: Manufacturing and implications; Bioprocess International; 8(4); pp. 42-48; Apr. 2010.
Marks et al.; By-passing immunization. Human antibodies from V-gene libraries displayed on phage; J Mol Biol; 222(3):581-597; Dec. 5, 1991.
Marks et al.; By-passing immunization: building high affinity human antibodies by chain shuffling; Biotechnology; 10(7):779-783; Jul. 1992.
Martin et al.; GAP domains responsible for ras p21-dependent inhibition of muscarinic atrial K+ channel currents; Science; 255(5041):192-194; Jan. 10, 1992.
Martin et al.; Irreversible coupling of immunoglobulin fragments to preformed vesicles. An improved method for liposome targeting; J Biol Chem; 257(1):286-8; Jan. 10, 1982.
Mast-I Group (Italy); Randomised controlled trial of streptokinase, aspirin, and combination of both in treatment of acute ischaemic stroke. Multicentre Acute Stroke Trial—Italy (MAST-I) Group; Lancet; 346(8989):1509-1514; Dec. 9, 1995.
Mather et al.; Culture of testicular cells in hormone-supplemented serum-free medium; Ann N Y Acad Sci; 383:44-68; Jun. 1982.
Mather; Establishment and characterization of two distinct mouse testicular epithelial cell lines; Biol Reprod; 23(1):243-52; Aug. 1980.
Matsuzaki, Masaharu; Measurement Methods of Platelet Activating Factor (PAF) and PAF Acetylhydrolase (PAFAH) Activity; SRL Hokan; 13(3): 36-41; (year of publication is sufficiently earlier than the effective U.S. filing date and any foreign priority date) 1989; English translation of introduction.
McAfferty et al.; Phage antibodies: filamentous phage displaying antibody variable domains; Nature; 348(6301):552-554; Dec. 6, 1990.
Matuo et al.; The usefulness of CHAPS as a non-cytotoxic stabilizing agent in purification of growth factors; Cytotechnology; 1(4); pp. 309-318; Nov. 1988.
McManus et al.; PAF, a Putative Mediator of Oral Inflammation; Crit Rev Oral Biol Med.; 11(2):240-258; (year of publication is sufficiently earlier than the effective U.S. filing and any foreign priority date) 2000.
Menzies et al.; Stimulation of specific binding of [3H]-progesterone to bovine luteal cell-surface membranes: specificity of digitonin; Mol. Cell Endrocrinol.; 153 (1-2); pp. 57-69; Jul. 20, 1999.
Miller et al.; Epitope binning of murine monoclonal antibodies by a multiplexed pairing assay; J Immunol Methods; 365(1-2):118-125; Feb. 28, 2011.
Milstein et al.; Hybrid hybridomas and their use in immunohistochemistry; Nature; 305:537-540; Oct. 1983.
Min et al., Platelet-Activating Factor Acetylhydrolases:? Broad Substrate Specificity and Lipoprotein Binding Does Not Modulate the Catalytic Properties of the Plasma Enzyme; Biochemistry; 40(15): 4539-4549; Apr. 17, 2001.
Miwa et al.; "Serum platelet-activating factor (PAF) acetylhydrolase of children with bronchial asthma," Japanese Journal of Inflammation; 8 (4):327-333; Dec. 1988; Abstract—HCAPLUS (1 Page).
Miwa et al.; Characterization of serum platelet-activating factor (PAF) acetylhydrolase. Correlation between deficiency of serum P AF acetylhydrolase and respiratory symptoms in asthmatic children; Journal of Clinical Investigation; 82(6): 1983-1991; Dec. 1988.
Miwa et al.; On Development of a Measurement Method of Serum PAF Acetylhydrolase Activity Using an Automatic Analyser, and the Clinical Significance of Serum PAF Acetylhydrolase Defect; Proceedings of Japanese Conference on the Biochemistry of Lipids; 34:305-308; (year of publication is sufficiently earlier than the effective U.S. filing date and any foreign priority date) 1992; English Abstract.
Miwa et al.; Serum platelet-activating factor (PAF) acetylhydrolase of children with bronchial asthma; Japanese Journal of Inflammation; 8(4):327-333; Dec. 1988.
Morimoto et al.; Single-step purification of F(ab')2 fragments of mouse monoclonal antibodies (immunoglobulins G1) by hydrophobic interaction high performance liquid chromatography using TSKgel Phenyl-5PW; J Biochem Biophys Methods; 24(1-2):107-117; Mar. 1992.
Morrison et al.; Chimeric human antibody molecules: mouse antigen-binding domains with human constant region domains; Proc Natl Acad Sci USA; 81(21):6851-5; Nov. 1984.
Muguruma et al.; The central role of PAF in necrotizing enterocolitis development; Adv Exp Med Biol.; 407:379-82; (year of publication is sufficiently earlier than the effective U.S. filing date and any foreign priority date) 1997.
Muhlestein et al.; The reduction of inflammatory biomarkers by statin, fibrate, and combination therapy among diabetic patients with mixed dyslipidemia; The DIACOR (Diabetes and Combined Lipid Therapy Regimen) study, J Am Coll Cardiol.; 48(2):396-401; Jul. 18, 2006.
Munson et al.; Ligand: a versatile computerized approach for characterization of ligand-binding systems; Anal Biochem; 107(1):220-239; Sep. 1, 1980.
National Cholesterol Education Program (NCEP) Expert Panel on Detection Evaluation, and Treatment of High Blood Cholesterol in Adults (Adult Treatment Panel III); Third report of the national cholesterol education program (NCEP) expert panel on detection, evaluation, and treatment of high blood cholesterol in adults (adult treatment panel III) final report; Circulation; 106(25); pp. 3143-3421; Dec. 17, 2002.
National Institute of Health (NIH), Clinical Guidelines on the Identification, Evaluation, and Treatment of Overweight and Obesity in Adults; Sep. 1998.
NCBI Entrez GeneID: 7941 (PLA2G7); PLA2G7 phospholipase A2, group VII (platelet-activating factor acetylhydrolase, plasma) [Homo sapiens (human) ]; http://www.ncbi.nlm.nih.gov/gene/7941; 9pgs; downloaded Aug. 27, 2013.
NCBI RefSegID: NP_001161829; platelet-activating factor acetylhydrolase precursor [Homo sapiens]; http://www.ncbi.nlm.nih.gov/protein/NP_001161829; 3pgs; downloaded Aug. 27, 2013.
NCBI RefSeqID: NM_001168357; Homo sapiens phospholipase A2, group VII (platelet-activating factor acetylhydrolase, plasma) (PLA2G7), transcript variant 2, mRNA; www.ncbi.nlm.nih.gov/nuccore/ NM_001168357.1? report=gbwithparts&log$=seqview; 5pgs; downloaded Aug. 27, 2013.
NCBI RefSeqID: NM_005084; Homo sapiens phospholipase A2, group VII (platelet-activating factor acetylhydrolase, plasma) (PLA2G7), transcript variant 1, mRNA; http://www.ncbi.nlm.nih.gov/nuccore/ NM_005084; 5pgs; ; downloaded Aug. 27, 2013.
NCBI RefSeqID: NP_005075; platelet-activating factor acetylhydrolase precursor [Homo sapiens]; http://www.ncbi.nlm.nih.gov/protein/ NP_005075.3; 3pgs; downloaded Aug. 27, 2013.
Neuberger et al.; Recombinant antibodies possessing novel effector functions; Nature; 312:604-608; Dec. 1984.

(56) References Cited

OTHER PUBLICATIONS

Oei et al.; Lipoprotein-associated phospholipase A2 is associated with risk of coronary heart disease and stroke; The Rotterdam Study () European Society of Cardiology Congress 2004; pp. 570-575; Aug.-Sep. 2004.
Owen et al.; Synthesis of a functional anti-phytochrome single-chain Fv protein in transgenic tobacco; Biotechnology; 10(7):790-794; Jul. 1992.
Paborsky et al.; Mammalian cell transient expression of tissue factor for the production of antigen; Protein Eng; 3(6):547-553; May 1990.
Packard et al.; Lipoprotein-associated phospholipase A2 as an independent predictor of coronary heart disease; N. Engl J Med; 343(16):1148-55; Oct. 19, 2000.
Pande; Membrane lipid composition differentially modulates the function of human plasma platelet activating factor-acetylhydrolase; Biochim. Biophys. Acta.; 1811(1); pp. 46-56; Jan. 2011.
Patrick et al.; Reduced PAF-Acetylhydrolase Activity is Associated with Postinjury Multiple Organ Failure; Shock; 7(3):170-174; Mar. 1997.
Paul, W.E. ed.; Fundamental Immunology; Raven Press, 3d Ed.; p. 242; Nov. 1993.
Pearson; Searching protein sequence libraries: comparison of the sensitivity and selectivity of the Smith-Waterman and FASTA algorithms; Genomics; 11(3):635-650; Nov. 1991.
Pinto et al.; Natural product derived inhibitors of lipoprotein associated phospholipase A2, synthesis and activity of analogues of SB-253514; Bioorg Med Chem Lett.; 10(17):2015-2017; Sep. 4, 2000.
Plückthun; Chap. 11: Antibodies from *Escherichia coli*; in: Rosenberg et al.; The Pharmacology of Monoclonal Antibodies, vol. 113; Springer-Verlag; New York, NY; pp. 269-315; 1994 (year of pub. sufficiently earlier than effective US filing date and any foreign priority date).
Plückthun; Mono- and bivalent antibody fragments produced in *Escherichia coli*: engineering, folding and antigen binding; Immunol Rev; 130:151-188; Dec. 1992.
Portolano et al.; Lack of Promiscuity in Autoantigen-Specific H and L Chain Combinations as Revealed by Human H and L Chain "Roulette;" J. Immunol.; 150(3):880-887; Feb. 1993.
Presta et al.; Humanization of an antibody directed against IgE; J Immunol; 151(5):2623-2632; Sep. 1, 1993.
Presta; Antibody engineering; Curr Opin Struc Biol; 2(4):593R596; Aug. 1992.
Pritchard et al.; The Degradation of Platelet-Activating Factor in the Plasma of a Patient with Familial High Density Lipoprotein Deficiency (Tangier Disease); Blood; 66(6):1476-1478; Dec. 1985.
Qin et al.; Concentration-dependent aggregation of CHAPS investigated by NMR spectroscopy; J. Phys. Chem. B; 114(11); pp. 3863-3868; Mar. 25, 2010.
Qin et al.; Proton NMR based investigation of the effects of temperature and NaCL on micellar properties of CHAPS; J. Phys. Chem. B; 115(9); pp. 1991-1998; Mar. 10, 2011.
Rattan et al., Protein synthesis, posttranslational modifications, and aging, Ann N Y Acad Sci.; 663:48-62; Nov. 21, 1992.
Ravetch et al.; Fc receptors; Annu Rev Immunol; 9:457-492; Apr. 1991.
Ridker et al.; Comparison of C-reactive protein and low-density lipoprotein cholesterol levels in the prediction of first cardiovascular events; N Engl J Med; 347(20):1557-65; Nov. 14, 2002.
Ridker et al.; Relationship of lipoprotien-associated phopholipase A2 mass and activity with incident vascular events among primary prevention patients allocated to placebo or statin therapy: an analysis form the JUPITER trial; Clinical Chemistry; Clinical Chemistry; 58(5); pp. 877-886; 2012 (year of pub. sufficiently earlier than effective US filing date and any foreign priority date).
Riechmann et al.; Reshaping human antibodies for therapy; Nature; 332 (6162):323-327; Mar. 24, 1988.
Riehl et al.; Platelet-activating factor acetylhydrolases in Caco-2 cells and epithelium of normal and ulcerative colitis patients; Gastroenterology; 109(6): 1826-1834; Dec. 1995.
Rosamond et al.; Heart disease and stroke statistics-2008 update: a report from the American Heart Association Statistics Committee and Stroke Statistics Subcommittee; Circulation; 117(4):e25-146; Jan. 29, 2008.
Rosensen; Fenofibrate reduces lipoprotein associated phospholipase A2 mass and oxidative lipids in hypertriglyceridemic subjects with the metabolic syndrome; Am Heart J.; 155(3):499.e.9-499.e16; Mar. 2008.
Rudikoff et al; Single amino acid substitution altering antigen-binding specificity; Proc Natl Acad Sci; 79(6): pp. 1979-1983; Mar. 1982.
Safford et al.; Association of race and sex with risk of incident acute coronary heart disease events; JAMA; 308(17); pp. 1768-1774; Nov. 7, 2012.
Samanta et al.; Crystal structure of human plasma platelet-activating factor acetylhydrolase: structural implication to lipoprotein binding and cataysis; J. Biol. Chem.; 283(43); pp. 31617-31624; Nov. 14, 2008.
Samanta et al.; Crystallization and preliminary x-ray crystallographic analysis of human plasma platelet activating factor acetyhydrolase; Protein Pept. Lett.; 16(1); pp. 97-100; Nov. 20, 2011.
Sandercock et al.; Antiplatelet therapy for acute ischaemic stroke. Cochrane Database of Systematic Reviews 2008, Issue 3. Art. No. CD000029; Jul. 2008.
Santos et al.; Relation of markers of inflammation (C-reactive protein, white blood cell count, and lipoprotein-associated phospholipase A2) to the ankle-brachial index; Vasc Med; 9(3):171-6; May 2004.
Saougos et al.; Differential effect of hypolipidemic drugs on lipoprotein-associated phospholipase A2; Arterioscler Thromb Vasc Biol; 27(10):2236-43; Oct. 2007.
Sarchielli et al.; Platelet-Activating Factor (PAF) in Internal Jugular Venous Blood of Migraine without Aura Patients Assessed During Migraine Attacks; Cephalagia; 24(8):623-630; Aug. 2004.
Satoh et al.; Plasma platelet-activating factor acetylhydrolase deficiency in Japanese patients with asthma; Am J Respir Crit Care Med.; 159(3):974-9; Mar. 1999.
Satoh et al.; Platelet-activating factor acetylhydrolase in plasma lipoproteins from patients with ischemic stroke; Stroke; 23(8); pp. 1090-1092; Aug. 1992.
Satoh et al; Platelet-activating factor (Paf) acetylhydrolase and plasma lipoproteins: Relative distribution of the activity among lipoprotein classes; Journal of Japan Atherosclerosis Society; 16(4):501-504; (year of publication is sufficiently earlier than the effective U.S. filing date and any foreign priority date) 1988.
Schaefer et al.; Effects of atorvastatin versus other statins on fasting and postprandial C-reactive protein and lipoprotein-associated phospholipase A2 in patients with coronary heart disease versus control subjects; Am J Cardiol; 95(9):1025-1032; May 1, 2005.
Schindler et al.; Fluorophore-labeled ether lipids: substrates for enzymes of the plateletactivating factor cycle in peritoneal polymorphonuclear leukocytes; Analytical Biochemistry; 174(2):477-84; Nov. 1, 1988.
Schott et al.; Biomarkers in heart failure: Lp-PLA2 (activity) was predictive heart failure in an at risk population and was prognostic in a population with heart failure (Lp-PLA2 mass); 2 pages; retrieved Jan. 14, 2015 from the internet (http://www.plactest.com/portal/course1/story_content/external_files/40106-01_MAB-HF-ver5.pdf).
Seifter et al.; Analysis for protein modifications and nonprotein cofactors; Methods Enzymol.;182:626-46; (year of publication is sufficiently earlier than the effective U.S. filing date and any foreign priority date) 1990.
Serebruany et al.; Depressed Plasma Platelet—Activating Factor Acetylhydrolasein Patients Presenting with Acute Myocardial Infarction; Cardiology; 90(2):127-130; Oct. 1998.
Servillo et al.; Simultaneous Determination of Lysophospholipids by High-performance Liquid Chromatography with Fluorescence Detection; Journal of Chromatography; 689(2):281-286; Feb. 1997.

(56) References Cited

OTHER PUBLICATIONS

SG3; Quality management systems—process validation guidance; The Global Harmonization Task Force; Edition 2; 36 pages; Jan. 2004.
Shalaby et al.; Development of humanized bispecific antibodies reactive with cytotoxic lymphocytes and tumor cells overexpressing the HER2 protooncogene; J Exp Med; 175(1):217-25; Jan. 1, 1992.
Shopes; A genetically engineered human IgG mutant with enhanced cytolytic activity; J Immunol; 148(9):2918-2922, May 1, 1992.
Sims et al.; A humanized CD18 antibody can block function without cell destruction; J Immunol; 151(4):2296-2308; Aug. 15, 1993.
Skerra; Bacterial expression of immunoglobulin fragments; Curr Opin Immunol; 5(2):256-62; Apr. 1993.
Skinner et al.; Use of the Glu-Glu-Phe C-terminal epitope for rapid purification of the catalytic domain of normal and mutant ras GTPase-activating proteins; J Biol Chem; 266(22):14163-6; Aug. 5, 1991.
Smith et al.; Identification of common molecular subsequences; J Mol Biol; 147(1):195-197; Mar. 25, 1981.
Song et al.; Sequencing of Lp-PLA2-encoding PLA2G7 gene in 2000 Europeans reveals several rare loss-of-function mutations; Pharmacogenomics J; 12(5):425-31; Oct. 2012.
Stafforini et al.; Human macrophages secrete platelet-activating factor acetylhydrolase; Journal of Biological Chemistry; 265(17); pp. 9682-9687; Jun. 1990.
Stafforini et al.; Human plasma platelet-activating factor acetylhydrolase. Association with lipoprotein particles and role in the degradation of platelet-activating factor; J. Biol. Chem.; 262(9); pp. 4215-4222; Mar. 25, 1987.
Stafforini et al.; Human Plasma Platelet-Activating Factor Acetylhyrolase. Purification and Properties; Journal of Biological Chemistry; 262(9):4223-4230; Mar 25, 1987.
Stafforini et al.; Lipoproteins alter the catalytic behavior of the platelet-activating factor acetylhydrolase in human plasma; Proc. Natl. Acad. Sci. USA; 86(7); pp. 2393-2397; Apr. 1989.
Stafforini et al.; Molecular basis of the interaction between plasma platelet-activating factor acetylhydrolase and low density lipoprotein; J. Biol. Chem.; 274; 4(11); pp. 7018-7024; Mar. 12, 1999.
Stafforini et al.; Platelet-Activating Factor Acetylhydrolase in Human erythrocytes; Methods in Enzymology; 197:411-425; (year of publication is sufficiently earlier than the effective U.S. filing date and any foreign priority date) 1991.
Stafforini et al.; Platelet-activating Factor Acetylhydrolases; J. Biol. Chem.; 272(29): 17895-17898; Jul. 18, 1997.
Stafforini; Biology of platelet-activating factor acetylhydrolase (PAF-AH, lipoprotein associated phospholipase A2); Cardiovasc. Drugs Ther.; 23(1); pp. 73-83; Feb. 2009.
Stevenson et al.; A chimeric antibody with dual Fc regions (bisFabFc) prepared by manipulations at the IgG hinge; Anticancer Drug Des; 3(4):219-30; Mar. 1989.
Stremler et al.; An oxidized derivative of phosphatidylcholine is a substrate for the platelet-activating factor acetylhydrolase from human plasma; J. Biological Chemistry; 264(10); pp. 5331-5334; Apr. 1989.
Strong et al.; Preventing stroke: saving lives around the world; Lancet Neurol.; 6(2):182-7; Feb. 2007.
Suckling et al.; Lipoprotein-associated phospholipase A2: a target directed at the atherosclerotic plaque; Expert Opin Ther Targets.; 6(3):309-314; Jun. 2002.
Suresh et al.; Bispecific monoclonal antibodies from hybrid hybridomas; Methods Enzymol; 121:210-228; 1986 (year of pub. sufficiently earlier than effective US filing date and any foreign priority date).
Tew et al.; Mechanism of Inhibition of LDL Phospholipase A2 by Monocyclic-?-lactams. Burst Kinetics and the Effect of Stereochemistry; Biochemistry; 37(28):10087-10093; Jul. 14, 1998.
Tew et al.; Purification, Properties, Sequencing, and Cloning of a Lipoprotein-Associated, Serine-Dependent Phospholipase Involved in the Oxidative Modification of Low-Density Lipoproteins; Arterioscler Thromb Vasc Biol. 16(4):591-599; Apr. 1996.
Thirkettle et al.; SB-253514 and Analogues; Novel Inhibitors of Lipoprotein-Associated Phospholipase A2 Produced by *Pseudomonas fluorescens* DSM 11579; J. Antibiotics; vol. 53(7):664-669; Jul. 2000.
Thirkettle, Jan; SB-253514 and Analogues; Novel Inhibitors of Lipoprotein Associated Phospholipase A2 Produced by *Pseudomonas fluorescens* DSM 11579. III. Biotransformation Using Naringinase; J. Antibiotics; vol. 53 (7):733-735; Jul. 2000.
Thompson et al.; Lipoprotein-associated phospholipase A(2) and risk of coronary disease, stroke, and mortality: collaborative analysis of 32 prospective studies; Lancet; 375(9725); pp. 1536-1544; May 1, 2010.
Tjoelker et al.; Plasma platelet-activating factor acetylhydrolase is a secreted phospholipase A2 with a catalytic triad; J. Bio. Chem.; 270(43); pp. 25481-25487; Oct. 27, 1995.
Tjoelker et.; Anti-inflammatory properties of a platelet-activating factor acetylhydrolase; Nature 374, 549-553; Apr. 6, 1995.
Traunecker et al.; Bispecific single chain molecules (Janusins) target cytotoxic lymphocytes on HIV infected cells; EMBO J; 10(12):3655-9; Dec. 1991.
Tselepis et al.; Association of the inflammatory state in active juvenile rheumatoid arthritis with hypoRhigh-density lipoproteinemia and reduced lipoprotein-associated platelet-activating factor acetylhydrolase activity; Arthritis Rheum.; 42(2):373R383, Feb. 1999.
Tselepis et al.; Inflammation, bioactive lipids and atherosclerosis: potential roles of a lipoprotein-associated phospholipase A2, platelet activating factor-acetylhydrolase; Atheroscler Suppl.; 3(4):57-68; Dec. 2002.
Tsimihodimos et al.; Altered distribution of platelet-activating factor-acetyhyrolase activity between Ldl and Hdl as function of the severity of hypercholesterolemia; J. Lipid Res.; 43(2); pp. 256-263; Feb. 2002.
Tsimihodimos et al.; Fenofirate iinduces HDL-associated PAF-AH but attenuates enzyme activity associated with apoB-containing lipoproteins; J. Lipid Res. 44(5); pp. 927-934; May 2003.
Tsuji et al.; The presence of platelet-activating factor-acetylhydrolase in human middle ear effusions; ORL J Otorhinolaryngol Relat Spec.; 60(1):25-9; Jan.-Feb. 1998.
Tsukioka et al.; Increased Plasma Level of Platelet-Activating Factor (PAF) and Decreased Serum PAF Acetylhydrolase (PAFAH) Activity in Adults with Bronchial Asthma; Journal of Investigational Allergology and Clinical Immunology; 6(1):22-29; Jan.-Feb. 1996.
Tutt et al.; Trispecific F(ab')3 derivatives that use cooperative signaling via the TCR/CD3 complex and CD2 to activate and redirect resting cytotoxic T cells; J Immunol; 147(1):60-9; Jul. 1, 1991.
Unno et al.; Single Nucleotide Polymorphism (G994?T) in the Plasma Platelet-Activating Factor-Acetylhydrolase Gene is Associated with Graft Patency of Femoropopliteal Bypass; Surgery; 132 (1):66-71; Jul. 2002.
Urlaub et al.; Isolation of Chinese hamster cell mutants deficient in dihydrofolate reductase activity; Proc Natl Acad Sci USA; 77(7):4216-20; Jul. 1980.
Van Vark et al.; Lipoprotein-associated phospholipase A2 activity and risk of heart failure: the rotterdam study; Eur. Heart J.; 27(19); pp. 2346-2352; Oct. 2006.
Verhoeyen et al.; Reshaping human antibodies: grafting an antilysozyme activity; Science; 239(4847):1534-6; Mar. 25, 1998.
Wardlaw et al.; Thrombolysis for acute ischaemic stroke. Cochrane Database of Systematic Reviews 2009, Issue 4. Art. No. CD000213; Oct. 2009.
Washburn et al.; Novel general approach for the assay and inhibition of hydrolytic enzymes utilizing suicide-inhibitory bifunctionally linked substrates (SIBLINKS): Exemplified by a phospholipase A2 assay; J. Am. Chem. Soc.; 112; pp. 2040-2041; Feb. 1990.
Washburn et al.; Suicide-inhibitory bifunctionally linked substrates (SIBLINKS) as phospholipase A2 inhibitors; J. Biological Chemistry; 266(8); pp. 5042-5048; Mar. 1991.
Waterhouse et al.; Combinatorial infection and in vivo recombination: a strategy for making large phage antibody repertoires; Nucleic Acids Res; 21(9):2265-6; May 11, 1993.

(56) References Cited

OTHER PUBLICATIONS

Wilson et al; Prediction of coronary heart disease using risk factor categories; Circulation; 97(18); pp. 1837-1847; May 12, 1998.
Winkler et al.; Fluvastatin slow-release lowers platelet-activating factor acetyl hydrolase activity: a placebo-controlled trial in patients with type 2 diabetes; J Clin Endocrinol Metab; 89(3):1153-9; Mar. 2004.
Witztum; The oxidation hypothesis of atherosclerosis; Lancet.; 344 (8925):793-5; Sep. 17, 1994.
Wold, Finn; Posttranslational Protein Modifications: Perspectives and Prospects; Posttranslational Covalent Modification of Proteins; B.C. Johnson, Ed.; Academic Press, New York; pp. 1-12; (year of publication is sufficiently earlier than the effective U.S. filing and any foreign priority date) 1983.
Wolff et al.; Monoclonal antibody homodimers: enhanced antitumor activity in nude mice; Cancer Res.; 53(11):2560-5; Jun. 1, 1993.
Yoon et al.; Interdependent effect of angiotensin-converting enzyme and platelet-activating factor acetylhydrolase gene polymorphisms on the progression of immunoglobulin A nephropathy; Clinical Genetics; 62(2):128-134; Aug. 2002.
Yoshida et al.; Platelet-activating factor acetylhydrolase in red cell membranes. Does decreased activity impair erythrocyte deformability inischemic stroke patients?; Stroke; 24(1); pp. 14-18; Jan. 1993.
Zalewski et al.; Role of Lipoprotein-Associated Phospholipase A2 in Atherosclerosis. Biology, Epidemiology, and Possible Therapeutic Target; Arterioscler Thromb Vasc Biol; 25(5):923-931; May 2005.
Zapata et al.; Engineering linear F(ab')2 fragments for efficient production in *Escherichia coli* and enhanced antiproliferative activity; Protein Eng; 8(10):1057-62; Oct. 1995.
Zhang et al.; Interactions between macromolecules and ions: The hofmeister series; Curr. Opin. Chem. Biol.; 10(6); pp. 658-663; Dec. 10, 2006.
EPO; EP1735457A4: Supplementary European Search Report; (application No. EP 05779946); Jul. 17, 2007, 2 pages.
WO; WO2005/113797A3 (App. PCT/US05/12948); PCT International Search Report; Apr. 7, 2006; 4 pgs.
JP 4346797 A Japanese patent application (Dec. 2, 1992)-abstracts (Derwent Information Ltd; HCAPLUS/ACS on STN)-2 pages.
JP 3036883B2 Japanese Patent (Apr. 24, 2000)—Paterra InstantMT Machine Translation—13 pages.
JP 6116279A Japanese patent application (Apr. 26, 1994)—abstract (Derwent Information Ltd)—1 page.
JP 6116279A Japanese patent application (Apr. 26, 1994)—Paterra InstantMT Machine Translation—28 pages.
JP 7059597 A Japanese patent application (Mar. 5, 1995)—abstracts (Derwent Information Ltd; HCAPLUS/ ACS on STN)—2 pages.
JP 7059597 A Japanese patent application (Mar. 5, 1995)—Paterra InstantMT Machine Translation—13 pages.
JP 2004018501A Japanese patent application (Jan. 22, 2004)—abstract (Derwent Information Ltd) 1 page.
JP2004018501A Japanese patent application (Jan. 22, 2004)—Paterra InstantMT Machine Translation—38 pages.
W000/32808A1 (Jun. 8, 2008)—abstracts (Derwent Information Ltd; HCAPLUS/ACS on STN)—2 pages.
W000/32808A1 (Jun. 8, 2000)—part, post-edited machine translation (Rising Sun Communications) 2 pages.
JP 2002223794A Japanese patent application (Aug. 13, 2002)—machine translation (from EPO file EP1735457)—20 pages.
JP 4220603B2 Japanese patent (Feb. 4, 2009)-claims translation (Patent Agent)—4 pages.
JP 4220603B2 Japanese patent (Feb. 4, 2009)—translation (Multilingual Solutions)—30 pages.
Heffernan et al.; Peripheral arterial tonometry for risk stratification inn men with coronary artery disease; Clin. Cardiol.; 33(2); pp. 94-98; Feb. 2010.
JP 4220603B2 Japanese patent (Feb. 4, 2009)—Paterra InstantMT Machine Translation (55 pages); post-edited claims (Lionbridge; 6 pages).
Schaal; U.S. Appl. No. 14/279,106 entitled "Value-Assigned Solutions of Lipoprotein-Associated Phospholipase A2 having a long shelf-life," filed May 15, 2014.
Schaal et al.; U.S. Appl. No. 14/279,148 entitled "Long shelf-life kits and methods for standardizing, verifying, calibrating or recalibrating detection of lipoprotein-associated phospholipase A2," filed May 15, 2014.
Shou et al.; U.S. Appl. No. 14/498,980 entitled "Methods for detecting LP-PLA2 activity and inhibition of LP-PLA2 activity," filed Sep. 26, 2014.
Arensdorf et al.; U.S. Appl. No. 14/540,749 entitled "Methods for treatment of coronary heart disease events based on lipoprotien-associated phospholipase A2 activity," filed Nov. 13, 2014.
Miller et al.; U.S. Appl. No. 14/678,562 entitled "Lipoprotein-associated phospholipase A2 antibody compositions and methods of use," filed Apr. 3, 2015.

TABLE 1

Measurement of Lp-PLA2 Activity in Patients Who Received Inhibitor in vivo

Lp-PLA2 Activity (nmol/min/mL)

| | LTP Radiometric Assay | | | | | | Auto PAF AH Assay | | | | | |
|---|---|---|---|---|---|---|---|---|---|---|---|---|
| Time (hr) | Drug #17 | Drug #18 | Drug #21 | Drug #22 | Drug #24 | Drug #25 | Drug #17 | Drug #18 | Drug #21 | Drug #22 | Drug #24 | Drug #25 |
| 0 | 36.19 | 29.82 | 16.03 | 32.14 | 39.13 | 19.08 | 402 | 349 | 197 | 345 | 459 | 205 |
| 0.5 | 34.25 | 3.70 | 8.19 | 30.25 | 35.38 | 18.86 | 346 | 303 | 192 | 353 | 398 | 177 |
| 1 | 17.33 | 2.10 | 1.39 | 27.43 | 3.53 | 2.52 | 410 | 260 | 239 | 345 | 426 | 178 |
| 2 | 3.82 | 1.30 | 0.62 | 8.76 | 1.48 | 0.71 | 338 | 296 | 214 | 332 | 336 | 178 |
| 3 | 2.04 | 1.77 | 0.79 | 4.61 | 1.11 | 0.51 | 333 | 299 | 217 | 357 | 482 | 196 |
| 4 | 1.83 | 1.82 | 0.88 | 1.58 | 1.02 | 0.45 | 333 | 297 | 206 | 350 | 502 | 194 |
| 6 | 1.22 | 2.33 | 1.06 | 1.18 | 1.49 | 0.53 | 297 | 295 | 184 | 350 | 402 | 186 |
| 12 | 3.38 | 4.72 | 2.19 | 2.91 | 3.26 | 1.56 | 321 | 295 | 197 | 353 | 538 | 157 |
| 24 | 6.05 | 7.05 | 3.87 | 5.06 | 6.65 | 3.46 | 413 | 323 | 235 | 362 | 547 | 229 |
| 32 | 7.31 | 6.55 | 3.17 | 3.59 | 7.85 | 4.15 | 346 | 296 | 242 | 350 | 530 | 213 |
| 48 | 10.62 | 9.64 | 5.34 | 5.82 | 10.29 | 5.42 | 475 | 287 | 211 | 321 | 537 | 221 |
| 96 | 18.31 | 14.65 | 10.22 | 12.38 | 16.88 | 11.05 | 463 | 322 | 227 | 341 | 569 | 245 |
| 144 | 29.31 | 18.51 | 14.26 | 17.72 | 25.14 | 17.14 | 452 | 324 | 224 | 369 | 502 | 313 |

FIG. 2

TABLE 2

Lp-PLA2 Activity (nmol/min/mL) in Patients
who Received Placebo and Inhibitor in vivo

| | LTP Radiometric | | Lp-PLA2 Activity (nmol/min/mL) Auto PAF AH | | Auto PAF AH | |
|---|---|---|---|---|---|---|
| Time (hr) | Placebo #21 | Placebo #25 | Placebo #21 | Placebo #25 | Drug #21 | Drug #25 |
| 0 | 23.50 | 22.10 | 231 | 238 | 197 | 205 |
| 0.5 | 26.15 | 23.11 | 227 | 246 | 192 | 177 |
| 1 | 18.97 | 23.69 | 237 | 246 | 239 | 178 |
| 2 | 25.99 | 27.10 | 233 | 245 | 214 | 178 |
| 3 | 27.07 | 33.33 | 247 | 260 | 217 | 196 |
| 4 | 28.71 | 12.14 | 219 | 267 | 206 | 194 |
| 6 | 25.31 | 24.97 | 216 | 232 | 184 | 186 |
| 12 | 25.54 | 25.11 | 238 | 252 | 197 | 157 |
| 24 | 28.40 | 27.09 | 250 | 268 | 235 | 229 |
| 32 | 24.96 | 31.86 | 294 | 275 | 242 | 213 |
| 48 | 25.50 | 24.72 | 233 | 279 | 211 | 221 |
| 96 | 14.34 | 23.38 | 256 | 347 | 227 | 245 |
| 144 | 27.03 | 30.30 | 271 | 247 | 224 | 313 |
| Mean | 24.73 | 25.30 | 242.46 | 261.69 | 214.23 | 207.08 |
| Stdv. | 3.96 | 5.27 | 21.57 | 29.37 | 18.62 | 40.01 |
| % CV | 16.00 | 20.85 | 8.89 | 11.22 | 8.69 | 19.32 |

FIG. 3

FORMULA I

FORMULA II

TABLE 3

Inhibition of LP-PLA2 Activity as Measured by Auto
PAF AH and Low Throughput Radiometric Assay.

| Timepoint (hr) | Drug #24 | Drug #25 | Drug #26 | Drug #27 | Drug #28 | Drug #29 | Drug #30 | Drug #31 |
|---|---|---|---|---|---|---|---|---|
| | | | | LTP Radiometric Assay | | | | |
| 0 | 20.48 | 20.11 | 25.74 | 24.56 | 23.95 | 30.95 | 25.58 | 23.13 |
| 0.5 | 6.74 | 10.08 | 1.85 | 16.77 | 4.43 | 22.16 | 10.97 | 8.05 |
| 1 | 1.03 | 2.14 | 1.89 | 5.21 | 3.25 | 4.28 | 7.63 | 3.93 |
| 2 | 0.88 | 0.77 | 1.62 | 2.45 | 1.97 | 2.13 | 6.10 | 1.10 |
| 3 | 0.82 | 1.20 | 1.83 | 1.74 | 2.25 | 2.07 | 2.43 | 0.92 |
| 4 | 1.48 | 1.21 | 1.85 | 1.28 | 2.43 | 2.20 | 2.00 | 1.13 |
| 6 | 1.45 | 1.22 | 1.67 | 1.74 | 3.25 | 2.66 | 2.74 | 1.20 |
| 12 | 2.98 | 3.06 | 4.20 | 3.99 | 5.34 | 7.20 | 5.43 | 3.37 |
| 24 | 5.59 | 5.99 | 7.18 | 7.06 | 8.30 | 15.24 | 8.94 | 5.23 |
| 32 | 8.24 | 5.44 | 20.40 | 8.95 | 7.94 | 32.93 | 10.40 | 7.39 |
| 48 | 10.06 | 7.62 | 20.18 | 13.29 | 11.24 | 27.30 | 13.81 | 8.56 |
| 72 | 14.77 | 11.81 | 13.25 | 13.41 | 13.69 | 29.10 | 18.31 | 12.21 |
| 96 | 16.18 | 14.58 | 14.79 | 16.19 | 15.59 | 27.66 | 19.75 | 15.46 |
| | | | | Auto PAF AH Assay | | | | |
| 0 | 370 | 370 | 370 | 370 | 370 | 370 | 370 | 370 |
| 0.5 | 352 | 352 | 352 | 352 | 352 | 352 | 352 | 352 |
| 1 | 613 | 613 | 613 | 613 | 613 | 613 | 613 | 613 |
| 2 | 356 | 356 | 356 | 356 | 356 | 356 | 356 | 356 |
| 3 | 373 | 373 | 373 | 373 | 373 | 373 | 373 | 373 |
| 4 | 360 | 360 | 360 | 360 | 360 | 360 | 360 | 360 |
| 6 | 323 | 323 | 323 | 323 | 323 | 323 | 323 | 323 |
| 12 | 369 | 369 | 369 | 369 | 369 | 369 | 369 | 369 |
| 24 | 375 | 375 | 375 | 375 | 375 | 375 | 375 | 375 |
| 32 | 416 | 416 | 416 | 416 | 416 | 416 | 416 | 416 |
| 48 | 365 | 365 | 365 | 365 | 365 | 365 | 365 | 365 |
| 72 | 435 | 435 | 435 | 435 | 435 | 435 | 435 | 435 |
| 96 | 445 | 445 | 445 | 445 | 445 | 445 | 445 | 445 |

FIG. 5

TABLE 4

In Vitro Inhibition of Lp-PLA2 Activity by Formula III in Four Plasma Samples

| Drug (nM) | Activity (nmol/min/mL) | | | | % Inhibition | | | |
|---|---|---|---|---|---|---|---|---|
| | #3 | #7 | #8 | #10 | #3 | #7 | #8 | #10 |
| 600 | 22.65 | 10.50 | 9.67 | 10.91 | 88.50 | 92.75 | 90.37 | 93.78 |
| 60 | 16.25 | 12.64 | 0.14 | 14.17 | 91.75 | 91.28 | 99.86 | 91.92 |
| 6 | 48.61 | 31.39 | 21.81 | 35.97 | 75.32 | 78.33 | 78.29 | 79.49 |
| 0.6 | 102.78 | 78.61 | 50.69 | 83.89 | 47.81 | 45.73 | 49.52 | 52.18 |
| 0.06 | 167.36 | 119.17 | 83.33 | 148.89 | 15.02 | 17.74 | 17.02 | 15.12 |
| 0.006 | 162.22 | 138.06 | 95.42 | 178.61 | 17.63 | 4.70 | 4.98 | −1.82 |
| 0.0006 | 200.97 | 142.36 | 86.67 | 179.17 | −2.05 | 1.73 | 13.70 | −2.14 |
| 0 | 196.94 | 144.86 | 100.42 | 175.42 | 0 | 0 | 0 | 0 |

FIG. 6

TABLE 5

| | Effect of Detergent on Substrate Specificity | |
|---|---|---|
| | % Inhibition | |
| Drug (nM) | with detergent | without detergent |
| 60000 | 96.01 | 68.01 |
| 6000 | 95.68 | 62.73 |
| 600 | 95.06 | 61.30 |
| 60 | 87.94 | 55.03 |
| 6 | 76.92 | 54.97 |
| 0.6 | 69.90 | 46.52 |
| 0.06 | 48.58 | 26.96 |
| 0.006 | 24.22 | 26.65 |
| 0.0006 | 19.18 | 19.88 |
| 0.00006 | 10.68 | 7.20 |
| 0 | 0 | 0 |

FIG. 7

TABLE 6

Comparison of Lp-PLA2 Activity as Measured Using Radiometric versus Modified Drug Sensitive Colorimetric Assay

| Time Point (hour) | Radiometric Assay Activity (nmol/min/mL) | % Inhibition (96 hr-100%) | Colorimetric Assay Activity (milliOD/min) | % Inhibition (96 hr-100%) |
|---|---|---|---|---|
| 0.5 | 28.02 | 47.00 | 34.47 | 36.55 |
| 1 | 3.19 | 93.97 | 22.98 | 57.70 |
| 6 | 10.14 | 80.83 | 19.8 | 63.56 |
| 48 | 44.52 | 15.80 | 33.76 | 37.86 |
| 96 | 52.87 | 0 | 54.33 | 0 |

FIG. 8

TABLE 7

Percent Inhibition of Lp-PLA2 Activity in Plasma Samples from Subjects Administered Lp-PLA2 Inhibitor % Inhibition

| | Radiometric Assay | | | | Auto PAF AH Assay | | | | Drug-Sensitive Colorimetric Assay | | | |
|---|---|---|---|---|---|---|---|---|---|---|---|---|
| | | | | | Pt. No. | | | | | | | |
| Time (hr) | 13 | 36 | 24 | 41 | 13 | 36 | 24 | 41 | 13 | 36 | 24 | 41 |
| 0 | 0 | 0 | 0 | 0 | 0 | 0 | 0 | 0 | 0 | 0 | 0 | 0 |
| 0.5 | 46.12 | 45.06 | 9.58 | 26.68 | 5.60 | 8.38 | 6.26 | 8.60 | 32.82 | 45.62 | 6.73 | 18.41 |
| 1 | 81.79 | 91.46 | 90.98 | 88.27 | 9.98 | 14.03 | 11.53 | 14.55 | 73.08 | 84.97 | 86.26 | 77.78 |
| 3 | 93.74 | 94.36 | 97.32 | 96.02 | 7.11 | 10.93 | 10.36 | 15.70 | 85.64 | 85.3 | 89.15 | 88.37 |

FIG. 9

TABLE 8

Lp-PLA2 Activity in Plasma Samples from Subjects Administered Lp-PLA2 Inhibitor

Lp-PLA2 Activity (nmol/min/mL)

| Time (hr) | Radiometric Assay | | | | Auto PAF AH Assay Pt. No. | | | | Drug-Sensitive Colorimetric Assay | | | |
|---|---|---|---|---|---|---|---|---|---|---|---|---|
| | 13 | 36 | 24 | 41 | 13 | 36 | 24 | 41 | 13 | 36 | 24 | 41 |
| 0 | 27.3 | 26.94 | 39.13 | 46.97 | 330.50 | 605.00 | 511.50 | 274.50 | 96.9 | 83.84 | 177.63 | 176.2 |
| 0.5 | 14.71 | 14.8 | 35.38 | 34.44 | 312.00 | 553.00 | 479.50 | 251.50 | 65.1 | 45.59 | 165.67 | 143.76 |
| 1 | 4.97 | 2.3 | 3.53 | 5.51 | 297.50 | 517.00 | 452.50 | 236.00 | 26.08 | 12.61 | 24.41 | 39.14 |
| 3 | 1.71 | 1.52 | 1.05 | 1.87 | 307.00 | 510.00 | 458.50 | 244.50 | 13.92 | 12.33 | 19.27 | 20.49 |

FIG. 10

TABLE 10

Activity of Recombinant Human Lp-PLA2 Protein by Modified Colorimetric Assay

| hrLp-PLA2 (ng/ml) | Activity (nmol/min/mL) |
|---|---|
| 0 | 0.0 |
| 103 | 0.6 |
| 206 | 1.5 |
| 412 | 4.4 |
| 825 | 12.0 |
| 1650 | 30.0 |
| 3300 | 69.7 |
| 6600 | 169.0 |
| 13200 | 397.1 |
| 14666 | 413.7 |

FIG. 12

TABLE 9

Lp-PLA2 ACTIVITY AND PERCENT INHIBITION BY SUBJECT AND ASSAY

| | | Lp-PLA2 ACTIVITY (nmol/min/mL) | | | % INHIBITION | | |
|---|---|---|---|---|---|---|---|
| SUBJECT | TIME(HR) | RADIOMETRIC | AUTO PAF AH | DRUG-SENSITIVE COLORIMETRIC | RADIOMETRIC | AUTO PAF AH | DRUG-SENSITIVE COLORIMETRIC |
| #109 | 0 | 140.47 | 703.50 | 193.21 | 0.00 | 0.00 | 0.00 |
| | 0.5 | 104.52 | 647.00 | 141.14 | 25.59 | 8.03 | 26.95 |
| | 1 | 26.80 | 605.00 | 39.10 | 80.92 | 14.00 | 79.76 |
| | 2 | 14.51 | 559.50 | 30.57 | 89.67 | 20.47 | 84.18 |
| | 3 | 18.06 | 602.50 | 35.03 | 87.14 | 14.36 | 81.87 |
| | 4 | 20.76 | 629.50 | 33.46 | 85.22 | 10.52 | 82.68 |
| | 5 | 19.57 | 651.50 | 31.77 | 86.07 | 7.39 | 83.55 |
| | 6 | 21.78 | 642.00 | 66.08 | 84.49 | 8.74 | 65.80 |
| | 9 | 32.01 | 571.50 | 49.86 | 77.21 | 18.76 | 74.19 |
| | 12 | 35.85 | 571.50 | 76.84 | 74.48 | 18.76 | 60.23 |
| #114 | 0 | 84.01 | 512.00 | 127.01 | 0.00 | 0.00 | 0.00 |
| | 0.5 | 65.24 | 456.50 | 89.99 | 22.34 | 10.84 | 29.15 |
| | 1 | 18.68 | 414.50 | 24.96 | 77.76 | 19.04 | 80.35 |
| | 2 | 14.34 | 406.50 | 21.22 | 82.93 | 20.61 | 83.29 |
| | 3 | 12.24 | 435.00 | 18.66 | 85.43 | 15.04 | 85.31 |
| | 4 | 13.50 | 409.00 | 18.15 | 83.93 | 20.12 | 85.71 |
| | 5 | 14.14 | 385.00 | 16.58 | 83.17 | 24.80 | 86.94 |
| | 6 | 16.10 | 388.50 | 21.01 | 80.84 | 24.12 | 83.46 |
| | 9 | 24.73 | 445.50 | 37.35 | 70.56 | 12.99 | 70.59 |
| | 12 | 28.82 | 409.50 | 111.00 | 65.69 | 20.02 | 12.60 |
| #115 | 0 | 60.58 | 310.00 | 83.99 | 0.00 | 0.00 | 0.00 |
| | 0.5 | 50.18 | 308.00 | 69.79 | 17.17 | 0.65 | 16.91 |
| | 1 | 10.60 | 242.00 | 22.46 | 82.50 | 21.94 | 73.26 |
| | 2 | 10.00 | 282.00 | 16.31 | 83.49 | 9.03 | 80.58 |
| | 3 | 13.03 | 287.50 | 21.31 | 78.49 | 7.26 | 74.62 |
| | 4 | 14.37 | 309.00 | 21.77 | 76.28 | 0.32 | 74.08 |
| | 5 | 13.63 | 279.50 | 15.83 | 77.50 | 9.84 | 81.16 |

*FIG. 11A*

TABLE 9-CONTINUED
Lp-PLA2 ACTIVITY AND PERCENT INHIBITION BY SUBJECT AND ASSAY

| | | Lp-PLA2 ACTIVITY (nmol/min/mL) | | | % INHIBITION | | |
|---|---|---|---|---|---|---|---|
| SUBJECT | TIME(HR) | RADIOMETRIC | AUTO PAF AH | DRUG-SENSITIVE COLORIMETRIC | RADIOMETRIC | AUTO PAF AH | DRUG-SENSITIVE COLORIMETRIC |
| | 6 | 15.96 | 306.50 | 25.84 | 73.65 | 1.13 | 69.24 |
| | 9 | 25.91 | 289.50 | 36.27 | 57.23 | 6.61 | 56.82 |
| | 12 | 26.92 | 336.00 | 53.72 | 55.56 | -8.39 | 36.04 |
| #118 | 0 | 101.65 | 382.50 | 102.59 | 0.00 | 0.00 | 0.00 |
| | 0.5 | 35.83 | 323.50 | 31.08 | 64.75 | 15.42 | 69.70 |
| | 1 | 16.73 | 334.00 | 19.69 | 83.54 | 12.68 | 80.81 |
| | 2 | 13.70 | 313.50 | 19.69 | 86.52 | 18.04 | 80.81 |
| | 3 | 14.09 | 335.00 | 13.17 | 86.14 | 12.42 | 87.16 |
| | 4 | 14.00 | 346.50 | 7.30 | 86.23 | 9.41 | 92.88 |
| | 5 | 14.05 | 353.50 | 22.94 | 86.18 | 7.58 | 77.64 |
| | 6 | 15.68 | 330.00 | 20.65 | 84.57 | 13.73 | 79.87 |
| | 9 | 21.11 | 338.00 | 27.16 | 79.23 | 11.63 | 73.52 |
| | 12 | 24.22 | 355.50 | 38.74 | 76.17 | 7.06 | 62.24 |
| #119 | 0 | 141.40 | 736.00 | 180.59 | 0.00 | 0.00 | 0.00 |
| | 0.5 | 25.97 | 596.50 | 20.14 | 81.63 | 18.95 | 88.89 |
| | 1 | 16.04 | 568.00 | 23.29 | 88.66 | 22.83 | 87.10 |
| | 2 | 13.50 | 579.00 | 19.54 | 90.45 | 21.33 | 89.18 |
| | 3 | 12.80 | 616.50 | 20.61 | 90.95 | 16.24 | 88.59 |
| | 4 | 12.85 | 597.50 | 21.27 | 90.91 | 18.82 | 88.22 |
| | 5 | 11.69 | 748.00 | 21.36 | 91.73 | -1.63 | 88.17 |
| | 6 | 11.41 | 714.00 | 21.39 | 91.93 | 2.99 | 88.16 |
| | 9 | 18.51 | 578.50 | 27.87 | 86.91 | 21.40 | 84.57 |
| | 12 | 21.27 | 607.50 | 38.46 | 84.96 | 17.46 | 78.70 |
| #121 | 0 | 97.09 | 440.50 | 134.39 | 0.00 | 0.00 | 0.00 |
| | 0.5 | 16.07 | 402.00 | 19.87 | 83.45 | 8.74 | 85.22 |
| | 1 | 10.00 | 401.00 | 14.99 | 89.70 | 8.97 | 88.85 |
| | 2 | 10.00 | 402.50 | 12.22 | 89.70 | 8.63 | 90.90 |
| | 3 | 10.00 | 414.50 | 15.08 | 89.70 | 5.90 | 88.78 |
| | 4 | 10.00 | 389.50 | 16.18 | 89.70 | 11.58 | 87.96 |
| | 5 | 10.00 | 416.00 | 18.14 | 89.70 | 5.56 | 86.50 |
| | 6 | 10.26 | 412.00 | 18.74 | 89.43 | 6.47 | 86.06 |
| | 9 | 14.41 | 428.00 | 26.18 | 85.16 | 2.84 | 80.52 |
| | 12 | 16.97 | 456.00 | 35.87 | 82.52 | -3.52 | 73.31 |
| #123 | 0 | 72.11 | 454.00 | 116.90 | 0.00 | 0.00 | 0.00 |
| | 0.5 | 39.68 | 410.50 | 63.95 | 44.97 | 9.58 | 45.29 |
| | 1 | 19.83 | 402.50 | 30.22 | 72.50 | 11.34 | 74.15 |
| | 2 | 19.42 | 369.50 | 29.51 | 73.07 | 18.61 | 74.76 |
| | 3 | 21.08 | 387.50 | 30.49 | 70.77 | 14.65 | 73.92 |
| | 4 | 19.51 | 406.50 | 29.42 | 72.94 | 10.46 | 74.84 |
| | 5 | 20.24 | 428.50 | 35.46 | 71.93 | 5.62 | 69.67 |
| | 6 | 19.66 | 393.00 | 39.29 | 72.74 | 13.44 | 66.39 |
| | 9 | 32.48 | 343.00 | 50.81 | 54.96 | 24.45 | 56.54 |
| | 12 | 34.26 | 324.00 | 61.16 | 52.49 | 28.63 | 47.69 |

*FIG. 11B*

| TABLE 9-CONTINUED Lp-PLA2 ACTIVITY AND PERCENT INHIBITION BY SUBJECT AND ASSAY ||||||||
|---|---|---|---|---|---|---|---|
| | | Lp-PLA2 ACTIVITY (nmol/min/mL) ||| % INHIBITION |||
| SUBJECT | TIME(HR) | RADIOMETRIC | AUTO PAF AH | DRUG-SENSITIVE COLORIMETRIC | RADIOMETRIC | AUTO PAF AH | DRUG-SENSITIVE COLORIMETRIC |
| #124 | 0 | 87.96 | 465.50 | 109.88 | 0.00 | 0.00 | 0.00 |
| | 0.5 | 58.09 | 434.50 | 64.40 | 33.96 | 6.66 | 41.39 |
| | 1 | 12.39 | 429.50 | 18.74 | 85.91 | 7.73 | 82.95 |
| | 2 | 10.00 | 367.50 | 10.11 | 88.63 | 21.05 | 90.80 |
| | 3 | 10.00 | 362.50 | 11.51 | 88.63 | 22.13 | 89.53 |
| | 4 | 10.00 | 403.00 | 11.21 | 88.63 | 13.43 | 89.80 |
| | 5 | 10.00 | 377.00 | 12.22 | 88.63 | 19.01 | 88.88 |
| | 6 | 10.00 | 366.00 | 17.01 | 88.63 | 21.37 | 84.52 |
| | 9 | 11.21 | 387.00 | 21.03 | 87.26 | 16.86 | 80.86 |
| | 12 | 15.69 | 355.00 | 30.70 | 82.16 | 23.74 | 72.06 |
| | 0 | 77.38 | 368.50 | 100.48 | 0.00 | 0.00 | 0.00 |
| #142 | 0.5 | 78.40 | 393.00 | 81.70 | -1.32 | -6.65 | 18.69 |
| | 1 | 30.87 | 340.50 | 37.07 | 60.11 | 7.60 | 63.11 |
| | 2 | 14.73 | 348.00 | 27.05 | 80.96 | 5.56 | 73.08 |
| | 3 | 12.41 | 348.00 | 22.64 | 83.96 | 5.56 | 77.47 |
| | 4 | 11.47 | 338.50 | 19.97 | 85.18 | 8.14 | 80.12 |
| | 5 | 10.66 | 336.50 | 18.35 | 86.22 | 8.68 | 81.74 |
| | 6 | 12.93 | 325.00 | 25.12 | 83.29 | 11.80 | 75.00 |
| | 9 | 22.03 | 312.00 | 38.84 | 71.53 | 15.33 | 61.34 |
| | 12 | 21.96 | 307.00 | 44.60 | 71.62 | 16.69 | 55.61 |
| #145 | 0 | 63.55 | 305.00 | 88.69 | 0.00 | 0.00 | 0.00 |
| | 0.5 | 22.46 | 272.50 | 32.96 | 64.66 | 10.66 | 62.84 |
| | 1 | 15.85 | 271.00 | 17.15 | 75.06 | 11.15 | 80.66 |
| | 2 | 14.45 | 271.50 | 21.07 | 77.26 | 10.98 | 76.24 |
| | 3 | 11.99 | 277.50 | 20.89 | 81.13 | 9.02 | 76.45 |
| | 4 | 10.02 | 256.50 | 19.02 | 84.23 | 15.90 | 78.55 |
| | 5 | 10.14 | 273.50 | 20.74 | 84.04 | 10.33 | 76.62 |
| | 6 | 11.33 | 273.50 | 23.71 | 82.17 | 10.33 | 73.27 |
| | 9 | 17.58 | 286.00 | 33.36 | 72.34 | 6.23 | 62.39 |
| | 12 | 20.83 | 261.50 | 34.83 | 67.22 | 14.26 | 60.73 |

*FIG. 11C*

TABLE 11

Activity of Purified Human Lp-PLA2 Enzyme by Modified Drug Sensitive Colorimetric Assay

| Purified hLp-PLA2 (ng/ml) | Activity (nmol/min/mL) |
|---|---|
| 0.00 | 0.00 |
| 1.56 | 0.65 |
| 3.13 | 1.37 |
| 6.25 | 2.47 |
| 12.50 | 5.06 |
| 25.00 | 11.37 |
| 50.00 | 25.68 |
| 75.00 | 37.83 |
| 100.00 | 54.34 |
| 200.00 | 119.34 |
| 400.00 | 212.95 |
| 600.00 | 273.60 |
| 800.00 | 324.85 |
| 1000.00 | 338.51 |
| 1200.00 | 363.60 |
| 1600.00 | 335.42 |

FIG. 13

TABLE 12

Effect of Preincubation of Plasma in Buffer R1 on Percent Inhibition of Lp-PLA2 Activity

| Drug (ng/mL) | Preincubation of Plasma in R1 Buffer Reaction Time (minutes) | | | |
|---|---|---|---|---|
| | 5 minutes | 2 minutes | 0 minutes | R1R2 premix |
| 0 | 0.00 | 0.00 | 0.00 | 0.00 |
| 2 | -2.33 | 3.94 | 10.76 | 15.10 |
| 5 | 2.39 | 4.83 | 17.18 | 25.76 |
| 10 | 9.35 | 10.03 | 18.97 | 27.17 |
| 30 | 35.14 | 42.02 | 45.19 | 53.92 |
| 60 | 39.97 | 39.17 | 49.00 | 57.64 |
| 90 | 72.26 | 72.58 | 76.61 | 77.69 |

FIG. 14

TABLE 13

Effect of Substrate Concentration on Percent Inhibition of Lp-PLA2 Activity

| Drug (ng/mL) | Substrate Concentration (uM) | | | |
|---|---|---|---|---|
| | 275 | 550 | 1100 | 2200 |
| 0 | 0.00 | 0.00 | 0.00 | 0.00 |
| 2 | 32.43 | 26.84 | 18.32 | 17.33 |
| 5 | 31.02 | 34.92 | 16.53 | 30.96 |
| 10 | 51.38 | 50.23 | 25.26 | 42.68 |
| 30 | 67.57 | 56.99 | 46.00 | 28.30 |
| 60 | 76.88 | 72.98 | 59.86 | 52.77 |
| 90 | 86.12 | 81.83 | 71.89 | 70.69 |

FIG. 15

TABLE 14

Effect of Sample Volume on Percent Inhibition of Lp-PLA2 activity

| Drug (ng/mL) | Plasma Sample Volume (µL) | | | |
| --- | --- | --- | --- | --- |
| | 5 | 15 | 25 | 50 |
| 0 | 0.00 | 0.00 | 0.00 | 0.00 |
| 2 | 88.47 | 4.15 | 18.32 | 13.22 |
| 5 | 09.11 | 19.85 | 16.53 | 10.26 |
| 10 | −14.73 | 39.11 | 25.26 | 33.03 |
| 30 | 33.90 | 23.53 | 46.00 | 55.58 |
| 60 | 34.14 | 56.68 | 59.86 | 67.68 |
| 90 | 43.78 | 62.68 | 71.89 | 79.14 |

FIG. 16

TABLE 15

Effect of the Deletion of Buffer R2A from the Assay

| | Sample | | | | | |
| --- | --- | --- | --- | --- | --- | --- |
| | 1 | 2 | 3 | 4 | 5 | 6 |
| R1 | 100 µL | 140 µL | 100 µL | 75 µL | 115 µL | 75 µL |
| R2A | 40 µL | 0 µL | 0 µL | 140 µL | 0 µL | 0 µL |
| R2B | 2 µL | 2 µL | 2 µL | 2 µL | 2 µL | 2 µL |
| Plasma | 25 µL | 25 µL | 25 µL | 50 µL | 50 µL | 50 µL |
| Vmax (milliOD/ Minute) | 40 | 90 | 70 | 40 | 150 | 120 |

FIG. 17

TABLE 16

Effect of Substrate Concentration on Vmax of Substrate Hydrolysis
Vmax (milliOD/min) of Substrate Hydrolysis in Absence of Buffer R2A

| Drug (ng/mL) | Substrate Concentration (uM) | | | | | |
|---|---|---|---|---|---|---|
| | 273 | 205 | 154 | 115 | 86 | 65 |
| 9000 | 10.18 | 13.01 | 5.70 | 5.76 | 5.23 | 3.40 |
| 900 | 14.25 | 10.45 | 6.66 | 5.32 | 4.54 | 4.06 |
| 90 | 98.56 | 72.58 | 64.27 | 61.08 | 53.56 | 44.88 |
| 30 | 117.89 | 94.33 | 83.66 | 75.21 | 65.47 | 54.08 |
| 10 | 114.89 | 93.75 | 79.87 | 76.21 | 67.31 | 54.90 |
| 5 | 112.58 | 93.22 | 82.11 | 76.71 | 66.46 | 52.99 |
| 0 | 110.82 | 90.18 | 80.40 | 73.58 | 63.73 | 56.30 |

FIG. 18

TABLE 17

Effect of Reaction Time on Reaction Rate Under Different
Plasma Volume and Substrate Concentrations

| Time (Hr) | Vmax (milliOD/min) | | | | | | | | | |
|---|---|---|---|---|---|---|---|---|---|---|
| | 25 µL Plasma/440 µM Substrate | | | | | 50 µL Plasma/154 µM Substrate | | | | |
| | 1 min | 2 min | 3 min | 4 min | 5 min | 1 min | 2 min | 3 min | 4 min | 5 min |
| 0 | 125.20 | 118.65 | 115.01 | 110.60 | 107.85 | 98.70 | 88.45 | 82.73 | 76.54 | 70.68 |
| 0.5 | 86.90 | 88.70 | 88.73 | 88.79 | 88.38 | 76.50 | 72.85 | 69.05 | 64.78 | 61.71 |
| 1 | 19.00 | 21.05 | 23.37 | 25.72 | 27.90 | 18.00 | 17.75 | 18.01 | 18.10 | 18.28 |
| 3 | 6.30 | 8.25 | 10.65 | 12.74 | 14.70 | 10.20 | 9.15 | 9.24 | 9.37 | 9.57 |

FIG. 19

TABLE 18

Intra-Assay Validation
Lp-PLA2 Activity (nmol/min/mL)

Subject No.

| Replicate No. | #6954966 | #5149192 | #0839829 | #5147931 | #5181480 | #5149190 | #5149188 | #6954955 | #6955001 | #6716001 |
|---|---|---|---|---|---|---|---|---|---|---|
| 1 | 112.26 | 64.53 | 147.94 | 138.05 | 94.56 | 105.37 | 132.26 | 140.35 | 140.56 | 139.30 |
| 2 | 115.68 | 78.40 | 137.14 | 135.75 | 93.59 | 97.35 | 109.41 | 135.33 | 124.53 | 145.92 |
| 3 | 108.92 | 74.29 | 156.52 | 146.62 | 90.45 | 113.87 | 111.78 | 129.55 | 119.30 | 145.30 |
| 4 | 113.24 | 74.49 | 174.22 | 143.55 | 93.10 | 102.86 | 107.25 | 138.82 | 116.93 | 140.14 |
| 5 | 108.01 | 69.62 | 138.47 | 140.28 | 92.82 | 120.07 | 107.87 | 128.85 | 130.31 | 140.14 |
| 6 | 113.31 | 80.14 | 146.83 | 145.16 | 91.85 | 114.70 | 112.89 | 134.70 | 136.59 | 147.87 |
| Average | 111.90 | 73.58 | 150.19 | 141.57 | 92.73 | 109.04 | 113.58 | 134.60 | 128.04 | 143.11 |
| % CV | 2.60 | 7.81 | 9.14 | 3.00 | 1.54 | 7.84 | 8.29 | 3.48 | 7.38 | 2.57 |

FIG. 20

TABLE 19

Inter-Assay Variability
Lp-PLA2 Activity (nmol/min/mL)

Subject No.

| Assay No. | #6954966 | #5149192 | #6839829 | #5147931 | #5181480 | #5149190 | #5149188 | #6954955 | #6955001 | #6716001 |
|---|---|---|---|---|---|---|---|---|---|---|
| 1 | 111.90 | 73.58 | 150.19 | 141.57 | 92.73 | 109.04 | 113.58 | 134.60 | 128.04 | 143.11 |
| 2 | 105.75 | 76.77 | 143.36 | 127.71 | 58.21 | 106.36 | 112.86 | 106.26 | 116.87 | 134.58 |
| 3 | 117.70 | 83.78 | 147.66 | 118.56 | 70.17 | 97.80 | 116.94 | 120.69 | 130.48 | 134.02 |
| Average | 111.79 | 78.04 | 147.07 | 129.28 | 73.70 | 104.40 | 114.46 | 120.52 | 125.13 | 137.24 |
| % CV | 5.34 | 6.69 | 2.35 | 8.96 | 23.78 | 5.62 | 1.90 | 11.76 | 5.80 | 3.71 |

FIG. 21

TABLE 20

Inter-Operator Variability
Lp-PLA2 Activity (nmol/min/mL)

Subject No.

| Operator No. | #6954966 | #5149192 | #6839829 | #5147931 | #5181480 | #5149190 | #5149188 | #6954955 | #6955001 | #6716001 |
|---|---|---|---|---|---|---|---|---|---|---|
| 1 | 111.79 | 78.04 | 147.07 | 129.28 | 73.70 | 104.40 | 114.46 | 120.52 | 125.13 | 137.24 |
| 2 | 107.20 | 70.46 | 128.55 | 128.06 | 66.74 | 100.98 | 106.22 | 114.00 | 114.09 | 109.69 |
| 3 | 98.60 | 74.85 | 136.87 | 111.37 | 62.05 | 82.44 | 102.25 | 100.23 | 112.41 | 104.82 |
| Average | 105.86 | 74.45 | 137.50 | 122.90 | 67.50 | 95.94 | 107.64 | 111.58 | 117.21 | 117.25 |
| %CV | 6.32 | 5.11 | 6.75 | 8.14 | 8.69 | 12.31 | 5.79 | 9.28 | 5.89 | 14.91 |

FIG. 22

TABLE 21

Freeze/Thaw Effect

Lp-PLA2 Activity (nmol/min/mL)

Subject No.

| Freeze/Thaw | 6954966 | 5149192 | 6839829 | 5147931 | 5181480 | 5149190 | 5149188 | 6954955 | 6955001 | 6716001 |
|---|---|---|---|---|---|---|---|---|---|---|
| 1 | 111.90 | 73.58 | 150.19 | 141.57 | 92.73 | 109.04 | 113.58 | 134.60 | 128.04 | 143.11 |
| 2 | 105.75 | 76.77 | 143.36 | 127.71 | 58.21 | 106.36 | 112.86 | 106.26 | 116.87 | 134.58 |
| 3 | 112.72 | 82.20 | 141.72 | 107.84 | 53.78 | 81.48 | 116.70 | 99.18 | 130.55 | 125.98 |
| 4 | 101.09 | 68.94 | 105.00 | 95.96 | 55.96 | 97.12 | 98.05 | 122.05 | 105.40 | 169.87 |
| Average | 107.87 | 75.37 | 135.07 | 118.27 | 65.17 | 98.50 | 110.30 | 115.52 | 120.21 | 143.38 |
| %CV | 5.08 | 7.39 | 15.09 | 17.18 | 28.33 | 12.63 | 7.56 | 13.77 | 9.59 | 13.24 |

FIG. 23

TABLE 22

Improved Detectable Inhibition in Human Subjects Administered Lp-PLA2 Inhibitor

| | Lp-PLA activity (nmol/min/mL) | | | % Inhibition | | |
|---|---|---|---|---|---|---|
| Time(hr) | 440 µM/25 µL | 112 µM/25 µL | 112 µM/45 µL | 440 µM/25 µL | 112 µM/25 µL | 112 µM/45 µL |
| Pre-dose | 110.59 | 38.95 | 35.59 | 0 | 0 | 0 |
| 0 | 51.85 | 14.41 | 11.58 | 53 | 63 | 67 |
| 0.5 | 48.74 | 15.08 | 8.87 | 56 | 61 | 75 |
| 1 | 47.39 | 12.10 | 9.55 | 57 | 69 | 73 |
| 2 | 41.97 | 14.54 | 11.48 | 62 | 63 | 68 |
| 3 | 40.67 | 11.51 | 6.54 | 63 | 70 | 82 |
| 4 | 35.88 | 9.37 | 7.31 | 68 | 76 | 79 |
| 6 | 43.32 | 9.62 | 6.12 | 61 | 75 | 83 |
| 9 | 39.37 | 10.59 | 7.52 | 64 | 73 | 79 |
| 12 | 39.66 | 11.22 | 8.85 | 64 | 71 | 75 |
| 18 | 48.87 | 13.53 | 11.32 | 56 | 65 | 68 |
| 24 | 39.08 | 8.24 | 6.30 | 65 | 79 | 82 |

FIG. 24

TABLE 23

| | | Lp-PLA2 Activity (nmol/min/mL) | | % Inhibition | |
|---|---|---|---|---|---|
| Subject No. | Time (hr) | 440 µM/ 25 µL | 112 µM/ 45 µL | 440 µM/ 25 µL | 112 µM/ 45 µL |
| N008 | Pre-dose | 104.20 | 25.81 | 0 | 0 |
| | 0 | 47.06 | 12.65 | 55 | 51 |
| | 0.5 | 45.87 | 12.67 | 47 | 51 |
| | 1 | 53.40 | 11.37 | 49 | 56 |
| | 2 | 61.13 | 13.14 | 41 | 49 |
| | 3 | 52.48 | 13.42 | 50 | 48 |
| | 4 | 46.51 | 6.19 | 55 | 76 |
| | 6 | 33.95 | 3.27 | 67 | 87 |
| | 9 | 43.87 | 6.21 | 58 | 76 |
| | 12 | 33.66 | 5.74 | 68 | 78 |
| | 18 | 62.77 | 6.54 | 40 | 75 |
| | 24 | 65.38 | 11.16 | 37 | 57 |
| N009 | Pre-dose | 168.28 | 42.62 | 0 | 0 |
| | 0 | 69.03 | 14.49 | 59 | 66 |
| | 0.5 | 66.97 | 16.97 | 60 | 60 |
| | 1 | 69.71 | 19.42 | 59 | 54 |
| | 2 | 73.99 | 17.16 | 56 | 60 |
| | 3 | 68.87 | 13.12 | 59 | 69 |
| | 4 | 54.75 | 3.64 | 67 | 91 |
| | 6 | 53.19 | 10.97 | 68 | 74 |
| | 9 | 60.76 | 11.27 | 64 | 74 |
| | 12 | 76.09 | 12.58 | 55 | 70 |
| | 18 | 71.39 | 18.51 | 58 | 57 |
| | 24 | 69.12 | 16.69 | 59 | 61 |
| N028 | Pre-dose | 188.82 | 53.36 | 0 | 0 |
| | 0 | 60.50 | 7.80 | 68 | 85 |
| | 0.5 | 54.96 | 3.29 | 71 | 94 |
| | 1 | 53.70 | 6.28 | 72 | 88 |
| | 2 | 62.98 | 7.24 | 67 | 86 |
| | 3 | 64.87 | 4.06 | 66 | 92 |
| | 4 | 42.65 | 1.31 | 77 | 98 |
| | 6 | 37.35 | 3.55 | 80 | 93 |
| | 9 | 43.99 | 2.99 | 77 | 94 |
| | 12 | 45.88 | 5.30 | 76 | 90 |
| | 18 | 53.56 | 13.40 | 72 | 75 |
| | 24 | 56.68 | 11.69 | 70 | 78 |
| N029 | Pre-dose | 139.03 | 73.80 | 0 | 0 |
| | 0 | 70.50 | 16.59 | 49 | 78 |
| | 0.5 | 65.92 | 15.45 | 53 | 79 |
| | 1 | 73.03 | 16.76 | 47 | 77 |
| | 2 | 62.98 | 15.33 | 55 | 79 |
| | 3 | 46.81 | 5.88 | 66 | 92 |
| | 4 | 46.09 | 5.39 | 67 | 83 |
| | 6 | 41.09 | 4.11 | 70 | 94 |
| | 9 | 44.12 | 6.54 | 68 | 91 |
| | 12 | 50.13 | 8.64 | 64 | 88 |
| | 18 | 59.08 | 10.71 | 58 | 85 |
| | 24 | 62.56 | 19.75 | 55 | 73 |

FIG. 25

TABLE 24

Assay of Recombinant Human Lp-PLA2 Using 112 μM
Substrate/45 μL Plasma

| hrLp-PLA2 (ng/mL) | Activity (nmol/min/mL) |
|---|---|
| 0.00 | 0.00 |
| 1.22 | 0.18 |
| 2.44 | 0.62 |
| 4.88 | 2.71 |
| 9.77 | 5.13 |
| 19.53 | 9.27 |
| 39.06 | 17.81 |
| 78.13 | 30.16 |
| 156.25 | 51.62 |
| 312.50 | 84.14 |
| 625.00 | 109.44 |
| 1250.00 | 93.90 |

FIG. 26

TABLE 25

Effect of Reaction Time Used for Activity Calculation
on Assay Dynamic Range

| Reaction Time Used for Activity Calculation | hrLp-PLA2 (ng/ml) | Activity (nmol/min/mL) | R |
|---|---|---|---|
| 3 min-1 min | 14.6-938 | 2.71-84.1 | 0.98 |
| 1 min-0 | 14.6-3750 | 3.2-196.5 | 0.97 |
| 30 sec-0 | 14.6-3750 | 3.4-210 | 0.98 |

FIG. 27

TABLE 26

| Lp-PLA2 Activity in Ten Serum Samples | | |
|---|---|---|
| Sample | Activity (nmol/min/mL) | % Inhibition |
| BRH28858 | 145.57 | 5.28 |
| BRH28859 | 131.36 | 1.73 |
| BRH28860 | 177.74 | 0.75 |
| BRH28861 | 187.11 | 0.79 |
| BRH28862 | 155.68 | 1.65 |
| BRH28865 | 144.04 | 3.28 |
| BRH28866 | 133.28 | 1.52 |
| BRH28867 | 131.28 | 2.92 |
| BRH28868 | 137.35 | 1.15 |
| BRH28869 | 140.00 | 3.66 |

FIG. 28

TABLE 27

| | In vitro Drug Inhibition of Serum Lp-PLA2 Activity | | | |
|---|---|---|---|---|
| Drug | Activity (nmol/min/mL) | | % Inhibition | |
| (ng/mL) | BRH28861 | BRH28867 | BRH28861 | BRH28867 |
| 0 | 153.90 | 110.17 | 0.00 | 0.00 |
| 1 | 166.90 | 103.62 | −8.44 | 5.95 |
| 2 | 137.46 | 92.54 | 10.69 | 16.00 |
| 5 | 154.60 | 103.66 | −0.45 | 5.91 |
| 10 | 137.70 | 82.47 | 10.53 | 25.14 |
| 30 | 55.54 | 40.38 | 63.91 | 63.35 |
| 60 | 16.34 | 13.66 | 89.38 | 87.60 |
| 90 | 18.08 | 10.17 | 88.25 | 90.77 |
| 900 | 3.52 | 7.91 | 97.71 | 92.82 |

FIG. 29

METHODS FOR DETECTING LP-PLA2 ACTIVITY AND INHIBITION OF LP-PLA2 ACTIVITY

CROSS REFERENCE TO RELATED APPLICATIONS

This application is a continuation of U.S. Ser. No. 14/498,980, filed on Sep. 26, 2014, Publication No. US-2015-0017671-A1, which is continuation-in-part of U.S. Ser. No. 12/817,677, filed on Jun. 17, 2010, now U.S. Pat. No. 8,846,309, which is a continuation of U.S. Ser. No. 11/106,239, filed on Apr. 14, 2005, now U.S. Pat. No. 7,741,020, which claims benefit of U.S. Provisional Application No. 60/563,078, filed Apr. 16, 2004, the entirety of which is incorporated by reference.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This invention relates generally to methods and materials for determining lipoprotein-associated phospholipase A2 (herein "Lp-PLA2") enzyme activity and inhibition of activity in tissue samples from animals.

BACKGROUND

Coronary heart disease (herein "CHD") is the leading cause of death in many industrial countries. Atherosclerosis is a form of arteriosclerosis or hardening of the arteries in which there is the progressive build-up of plaque containing cholesterol and lipids in blood arteries. This build-up is associated with an increased risk of heart disease and morbid coronary events. The build-up of plaque in the arteries is associated with an immune response that is triggered by damage to the endothelium. Initially, monocyte-derived macrophages accumulate at the damaged site, due to the immune response causing a migration and accumulation of smooth muscle cells which form fibrous plaque in combination with the macrophages, lipids, cholesterol, calcium salts and collagen. The growth of such lesions can eventually block the artery and restrict blood flow.

Lp-PLA2, also known as PAF acetylhydrolase, is a secreted, calcium-independent member of the growing phospholipase A2 superfamily (Tew, et al. (1996) Arterioscler Thromb Vasc Biol. 16(4):591-9; Tjoelker, et al. (1995) Nature 374(6522):549-53). It is produced by monocytes, macrophages, and lymphocytes and is found associated predominantly with LDL (.about.80%) in human plasma. The enzyme cleaves polar phospholipids, including sn-2 ester of 1-O-alkyl-2-scetyl-sn-glycero-3-phosphocholine, otherwise known as platelet-activating factor (herein "PAF") (Tjoelker, et al. (1995) Nature 374(6522):549-53).

Many observations have demonstrated a pro-inflammatory activity of oxidized LDL when compared with native unmodified lipoproteins. One of the earliest events in LDL oxidation is the hydrolysis of oxidatively modified phosphatidylcholine, generating substantial quantities of lysophosphatidylcholine (herein "lyso-PC") and oxidized fatty acids. This hydrolysis is mediated solely by Lp-PLA2 (i.e., Lp-PLA2 hydrolyzes PAF to give lyso-phosphatidylcholine [herein "lyso-PC"] and acetate). (Stafforini, et al. (1997) J. Biol. Chem. 272, 17895)

Lyso-PC is suspected to be a pro-inflammatory and pro-atherogenic mediator. In addition to being cytotoxic at higher concentrations, it is able to stimulate monocyte and T-lymphocyte chemotaxis, as well as induce adhesion molecule and inflammatory cytokine expression at more modest concentrations. Lyso-PC has also been identified as the component of oxidized LDL that is involved in the antigenicity of LDL, a feature that may also contribute to the inflammatory nature of atherosclerosis. Moreover, lyso-PC promotes macrophage proliferation and induces endothelial dysfunction in various arterial beds. The oxidized fatty acids that are liberated together with lyso-PC are also monocyte chemoattractants and may also be involved in other biological activities such as cell signaling). Because both of these products of Lp-PLA2 hydrolysis are potent chemoattractants for circulating monocytes, Lp-PLA2 is thought to be responsible for the accumulation of cells loaded with cholesterol ester in the arteries, causing the characteristic "fatty streak" associated with the early stages of atherosclerosis.

Lp-PLA2 has also been found to be enriched in the highly atherogenic lipoprotein subfraction of small dense LDL, which is susceptible to oxidative modification. Moreover, enzyme levels are increased in patients with hyperlipidaemia, stroke, Type 1 and Type 2 diabetes mellitus, as well as in post-menopausal women. As such, plasma Lp-PLA2 levels tend to be elevated in those individuals who are considered to be at risk of developing accelerated atherosclerosis and clinical cardiovascular events. Thus, inhibition of the Lp-PLA2 enzyme would be expected to stop the buildup of this fatty streak (by inhibition of the formation of lysophosphatidylcholine), and so be useful in the treatment of atherosclerosis.

Lp-PLA2 inhibitors inhibit LDL oxidation. Lp-PLA2 inhibitors may therefore have a general application in any disorder that involves lipid peroxidation in conjunction with the enzyme activity, for example in addition to conditions such as atherosclerosis and diabetes other conditions such as rheumatoid arthritis, stroke, myocardial infarction (Serebruany, et al. Cardiology. 90(2):127-30 (1998)); reperfusion injury and acute and chronic inflammation. In addition, Lp-PLA2 is currently being explored as a biomarker of coronary heart disease (Blankenberg, et al. J Lipid Res. 2003 May 1) and arteriosclerosis (Tselepis and Chapman. Atheroscler Suppl. 3(4):57-68 (2002)). Furthermore, Lp-PLA2 has been shown to play a role in the following disease: respiratory distress syndrome (Grissom, et al. Crit. Care Med. 31(3):770-5 (2003); immunoglobulin A nephropathy (Yoon, et al. Clin Genet. 62(2):128-34 (2002); graft patency of femoropopliteal bypass (Unno, et al. Surgery 132(1):66-71 (2002); oral inflammation (McManus and Pinckard. Crit. Rev Oral Biol Med. 11(2):240-58 (2000)); airway inflammation and hyperreactivity (Henderson, et al. J Immunol. 15; 164(6):3360-7 (2000)); HIV and AIDS (Khovidhunkit, et al. Metabolism. 48(12):1524-31 (1999)); asthma (Satoh, et al. Am J Respir Crit. Care Med. 159(3):974-9 (1999)); juvenile rheumatoid arthritis (Tselepis, et al. Arthritis Rheum. 42(2):373-83 (1999)); human middle ear effusions (Tsuji, et al. ORL J Otorhinolaryngol Relat Spec. 60(1):25-9 (1998)); schizophrenia (Bell, et al. Biochem Biophys Res Commun. 29; 241(3):630-5 9 (1997)); necrotizing enterocolitis development (Muguruma, et al. Adv Exp Med. Biol. 407:379-82 (1997)); and ischemic bowel necrosis (Pediatr Res. 34(2):237-41 (1993)).

Lp-PLA2 activity from human tissue samples has been measured using spectrophotometric activity and fluorogenic activity assays (Cayman Chemical Company, and Karlan Research Products). See also Kosaka, et al. Clin Chem Acta 296(1-2):151-61 (2000) and Kosaka, et al. Clin Chem Acta 312(1-2):179-83 (2001). For instance, Azwell, Inc. (Osaka, Japan) reported in 2000 the synthesis and use of 1-myristoyl-2-(p-nitrophenylsuccinyl) phosphatidylcholine as a colorimetric substrate for measurement of human PAF AH (Lp-PLA2) activity in plasma and serum. In 2002, Azwell launched its research-use-only Auto PAF AH assay kit that utilizes this substrate and is formatted for use in a clinical chemistry analyzer. These methods may be capable of detecting inhibition of Lp-PLA2 activity when an inhibitor of Lp-PLA2 is added to a tissue sample in vitro. However, the methods provided with the Auto PAF AH assay are insensitive to measuring inhibition of Lp-PLA2 activity when an inhibitor of Lp-PLA2 has been administered to an animal prior to tissue sample collection.

In order to measure Lp-PLA2 activity in the presence of inhibitor in a tissue sample obtained from an animal administered inhibitor, an activity protocol is required.

Accordingly, methods for determining LP-PLA2 activity and inhibition from a tissue sample obtained from an animal that has been administered an Lp-PLA2 inhibitor are greatly needed. Thus, there is a need for colorimetric or fluorometric methods and assays for accurately detecting inhibition of Lp-PLA2 activity, particularly with a sufficient dynamic range.

None of the existing assays described above can provides a colorimetric or fluorometric method that is able to reliable detect grater then 30% inhibition of Lp-PLA2 activity in an animal (including humans) that has been administered an inhibitor of Lp-PLA2. As described in more detail below, prior art colorimetric or fluorometric methods (assays) for detecting Lp-PLA2 activity (spectrophotometric assays) are insensitive to the inhibition of Lp-PLA2, and typically indicate less than 30% of inhibition of LpPLA2 even in the presence of high levels of inhibitor. Further, none of these colorimetric or fluorometric assays can detect Lp-PLA2 activity/inhibition with a 100-fold or greater dynamic range. Described herein are methods and assays which may address these needs.

SUMMARY OF THE DISCLOSURE

In general, described herein are methods and assays for colorimetrically or fluorometrically detecting Lp-PLA2 inhibition (and particularly accurately reflecting up to 75% inhibition or more).

For example, described herein is a colorimetric or fluorometric method of determining the percentage of inhibition of Lp-PLA2 activity. The method may include: colorimetrically or fluorometrically detecting Lp-PLA2 activity from a first blood sample that is taken from the subject at a first time and diluted less than 33 times; colorimetrically or fluorometrically detecting Lp-PLA2 activity from a second blood sample that is taken from the subject at a second time one hour or more after the first time and diluted less than 33 times; and detecting greater than 30% inhibition of Lp-PLA2 activity between the first and second blood samples by comparing the activity of the Lp-PLA2 between the first and second blood samples, indicating that the subject has taken a drug that inhibits Lp-PLA2.

Any of the detection steps may colorimetrically or fluorometrically detect Lp-PLA2 activity by the use of a relatively low dilution of the sample (e.g., less than 50 fold, less than 45 fold, less than 40 folk, less than 35 fold, less than 33 fold, less than 30 fold, etc.) dilution of sample in the assay. The detection step may include the use of a substrate having a colormetric or fluorometric moiety. For example, preparing a solution may comprise preparing a solution including a substrate for Lp-PLA2 having a colorimetric or fluorometric detectable moiety.

The second blood sample may be taken (e.g., from the same subject) after the subject has been administered a drug that inhibits Lp-PLA2. Any of these detection steps may be performed after 0.5 hours, after 0.6 hours, 0.7 hours, 0.8 hours, 0.9 hours, 1 hour, 1.5 hours, etc., after the subject or sample has been exposed to the inhibitor, to detect greater than 30% inhibition.

In some variations, the step of detecting greater than 30% inhibition of Lp-PLA2 activity comprises detecting greater than 70% inhibition (after one hour), as illustrated in Table 7 and Table 9, below, or detecting greater than 75%, greater than 80%, greater than 85%, greater than 90%, etc. inhibition of Lp-PLA2, between the first and second blood samples (e.g., between inhibitor-free and inhibitor-exposed samples). The percent inhibition may also be measured with respect to a standard activity level (for a population, or a representative population, relative to the subject), rather than by comparing inhibitor-free and after-exposed to inhibitor in the same patient. Instead, the inhibitor-free values used to determine the percent inhibition may be based on one or more standards.

The step of detecting greater than 30% inhibition of Lp-PLA2 activity may comprise detecting at least or exactly 85-95% inhibition of Lp-PLA2 between the first and second blood samples.

Any appropriate tissue sample may be used, including in particular, blood samples, such as samples of blood plasma or blood serum samples. The sample may be fresh or frozen (thawed).

As mentioned, in general the methods described herein comprise colorimetrically or fluorometrically detecting Lp-PLA2 activity from the first and second blood samples by detecting Lp-PLA2 activity within a dynamic range of 100-fold or greater.

For example, a method of clinically monitoring a patient to assess the efficacy of an inhibitor of lipoprotein-associated phospholipase A2 (Lp-PLA2) may include: receiving a sample from an animal that has been administered an Lp-PLA2 inhibitor; and colorimetrically or fluorometrically detecting greater than 30 percent inhibition of Lp-PLA2 from the sample by contacting the sample with a solution comprising a substrate for Lp-PLA2. Colorimetrically or fluorometrically detecting may comprise detecting inhibition of Lp-PLA2 from a plurality of samples obtained from the animal at one or more than one time point before and after administration of Lp-PLA2 inhibitor. For example, colorimetrically or fluorometrically detecting may comprise comparing the activity of Lp-PLA2 from a plurality of samples including at least one sample obtained from the animal prior to the administration of Lp-PLA2 inhibitor.

In general, in any of these methods, the substrate concentration may be between about 53 µM to about 1125 µM. Alternatively or additionally, the substrate concentration may be less than 10 times the Km of Lp-PLA2 for the given substrate.

For example, described herein are methods of determining inhibition of lipoprotein-associated phospholipase A2 (Lp-PLA2) enzyme activity from a sample, the method comprising: preparing a solution comprising a substrate for Lp-PLA2; contacting a sample from an animal that has been administered an Lp-PLA2 inhibitor, wherein the sample is diluted less than a 33 fold by contact with the solution; and colorimetrically or fluorometrically detecting Lp-PLA2 activity. Colorimetrically or fluorometrically detecting Lp-PLA2 activity may comprise detecting greater than 30 percent inhibition (e.g., at least 85-95% inhibition).

For example, described herein are colorimetric or fluorometric methods of detecting greater than 30% inhibition of lipoprotein-associated phospholipase A2 (Lp-PLA2) enzyme, the method comprising: preparing a solution comprising a substrate for Lp-PLA2; contacting a sample from an animal that has been administered an Lp-PLA2 inhibitor, wherein the sample is diluted less than 33-fold; colorimetrically or fluorometrically detecting Lp-PLA2 activity. Colorimetrically or fluorometrically detecting Lp-PLA2 activity may comprise detecting at least 85-95% inhibition.

For example, in one aspect of the present invention, a method is provided for determining inhibition of Lp-PLA2 enzyme activity in at least one tissue sample comprising the steps of preparing a solution comprising a substrate for Lp-PLA2 comprising a colorimetric or fluorometric detectable moiety; contacting at least one said tissue sample with the solution of the preparing step; and detecting Lp-PLA2 activity, wherein the tissue sample is from an animal that has been administered with Lp-PLA2 inhibitor.

In another example of the current invention, a method is provided for determining Lp-PLA2 enzyme activity in a tissue sample obtained from an animal comprising the steps of: a) contacting 110 µL of a solution comprising: a solution comprising 90 mM 1-myristoyl-2-(4-nitrophenylsuccinyl) phosphatidylcholine contacted with a solution comprising 200 mM HEPES, 200 mM NaCl, 5 mM EDTA, 10 mM CHAPS, 10 mM sodium 1-nonanesulfonate at a pH 7.6 in a ratio of 0.66 µL to 110 µL; with at least one 25 µL tissue sample from an animal; with 25 µL each of a p-nitrophenol standard solution comprising; 4, 3, 2, 1, 0.4 or 0.2 nmol/µL p-nitrophenol in methanol; and 25 µL of phosphate buffered saline (PBS) or ddH$_2$O to make a blank; and b) determining Lp-PLA2 activity.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 2 is Table 1, showing the measurement of Lp-PLA2 activity in patients who received inhibitor in vivo using a radiometric assay and an "Auto PAF AH Assay" (prior art) at time points from 0 (before administration of the inhibitor) to 144 hrs after administering the inhibitor. The radiometric assay, while expensive and difficult to perform, accurately indicates inhibition of Lp-PLA2 activity over time, while the Auto PAF AH Assay does not detect inhibition.

FIG. 3 is Table 2, showing Lp-PLA2 activity (nmol/min/nL) in patients who received placebo and inhibitor in vivo, using a radiometric and Auto PAF AH (prior art) assay.

FIG. 5 is Table 3, showing inhibitor of Lp-PLA2 activity as measured by Auto PAF AH and low throughput radiometric assay, showing the inability of the Auto PAF AH assay to detect inhibition of LpPLA2 activity, which is detectable in the radiometric assay.

FIG. 6 is Table 4, showing the in vitro inhibition of LpPLA2 activity by Formula III, as detected with one variation of a drug-sensitive colorimetric Lp-PLA2 activity assay as described herein.

FIG. 7 is Table 5, showing the effect of detergent on substrate specificity for one variations of a drug-sensitive colorimetric Lp-PLA2 activity assay.

FIG. 8 is Table 6, showing a comparison of the standard radiometric assay and one variation of a drug-sensitive colorimetric Lp-PLA2 activity assay.

FIG. 9 is Table 7, showing a percent inhibition of Lp-PLA2 Activity in plasma samples from subjects administered an Lp-PLA2 inhibitor, comparing a radiometric assay, the Auto PAF Drug-Sensitive Assay, and one variation of a drug-sensitive colorimetric Lp-PLA2 activity assay. The drug-sensitive colorimetric Lp-PLA2 activity assay was able to detect greater than 30% inhibition of the Lp-PLA2 due to the inhibitor, in all subjects after 1 hour following administration, whereas the Auto PAF AH assay was not able to detect greater than 16% inhibition.

FIG. 10 is Table 8, showing Lp-PLA2 activity in plasma samples from subjects administered an Lp-PLA2 inhibitor, showing a comparison between a radiometric assay, the Auto PAF AH assay and an example of a drug-sensitive colorimetric Lp-PLA2 activity assay.

FIGS. 11 (part 1), 11 (part 2) and 11 (part 3) are Table 9, showing Lp-PLA2 activity and percent inhibition by subject and assay and comparing the results for the radiometric, auto PAF AH and an example of a drug-sensitive colorimetric Lp-PLA2 activity assay. The drug-sensitive colorimetric Lp-PLA2 method was sensitive to inhibition of Lp-PLA2, as was the radiometric assay method, and was able to show greater than 30% inhibition (and greater than 75-80% inhibition, particularly after 1 hour post-administering of the inhibitor; in contrast the Auto PAF AH assay appeared insensitive to the inhibition and indicated a maximum of about 28.6% inhibition.

FIG. 12 is Table 10, showing the detection of activity of recombinant human Lp-PLA2 protein using a modified colorimetric assay (e.g., a drug-sensitive colorimetric Lp-PLA2 activity assay). In Table 10, the range of activity values for the drug-sensitive colorimetric Lp-PLA2 activity assay also indicates the dynamic range of the method, which is greater than 100-fold and is up to almost 700-fold (>690-fold).

FIG. 13 is Table 11, showing the activity of purified human Lp-PLA2 enzyme determined using a drug sensitive colorimetric Lp-PLA2 activity assay. As in Table 10, the dynamic range of the method is greater than 100-fold.

FIG. 14 is Table 12, showing the effect of preincubation of plasma in buffer R1 on percent inhibition of Lp-PLA2 activity in a drug-sensitive colorimetric Lp-PLA2 activity assay.

FIG. 15 is Table 13, showing the effect of substrate concentration on percent inhibition of Lp-PLA2 activity in a drug-sensitive colorimetric Lp-PLA2 activity assay.

FIG. 16 is Table 14, showing the effect of sample volume on percent inhibition of Lp-PLA2 activity in a drug-sensitive colorimetric Lp-PLA2 activity assay.

FIG. 17 is Table 15, showing the effect of the removal of buffer R2A from the assay (e.g., in the absence of a substrate stabilizer, such as citric acid, which improved the assay in relation to other colorimetric assays such as the Auto PAF AH assay).

FIG. 18 is Table 16, showing the effect of substrate concentration on Vmax of substrate hydrolysis Vmax (milliOD/min) of substrate hydrolysis in absence of buffer R2A.

FIG. 19 is Table 17, showing the effect of reaction time on reaction rate under different plasma volume and substrate concentrations.

FIG. 20 is Table 18, showing the results of intra-assay validation for a drug-sensitive colorimetric Lp-PLA2 activity assay.

FIG. 21 is Table 19, showing the results of inter-assay validation for a drug-sensitive colorimetric Lp-PLA2 activity assay.

FIG. 22 is Table 20, showing inter-operator variability for a drug-sensitive colorimetric Lp-PLA2 activity assay.

FIG. 23 is Table 21, showing the effect of freezing/thawing in a drug-sensitive colorimetric Lp-PLA2 activity assay.

FIG. 24 is Table 22, showing detection of inhibition of Lp-PLA2 using variations of drug-sensitive colorimetric Lp-PLA2 activity assays (at three different substrate concentrations, 440 µM substrate/25 µL plasma, 112 µM substrate/25 µL plasma, and 112 µM substrate/45 µL plasma).

FIG. 25 is Table 23, showing the detection of inhibition with variations of drug-sensitive colorimetric Lp-PLA2 activity assays.

FIG. 26 is Table 24, showing the results of assays of recombinant human Lp-PLA2 using 112 µM substrate/45 µL plasma in a drug-sensitive colorimetric Lp-PLA2 activity assay.

FIG. 27 is Table 25, showing the effect of reaction time used for activity calculation on assay dynamic range for a variation of a drug-sensitive colorimetric Lp-PLA2 activity assay.

FIG. 28 is Table 26, showing the effect of Lp-PLA2 activity in ten serum samples using a drug-sensitive colorimetric Lp-PLA2 activity assay.

FIG. 29 is Table 27, showing in vitro drug inhibition of serum Lp-PLA2 activity using a drug-sensitive colorimetric Lp-PLA2 activity assay.

DETAILED DESCRIPTION

Glossary

Figure 1:
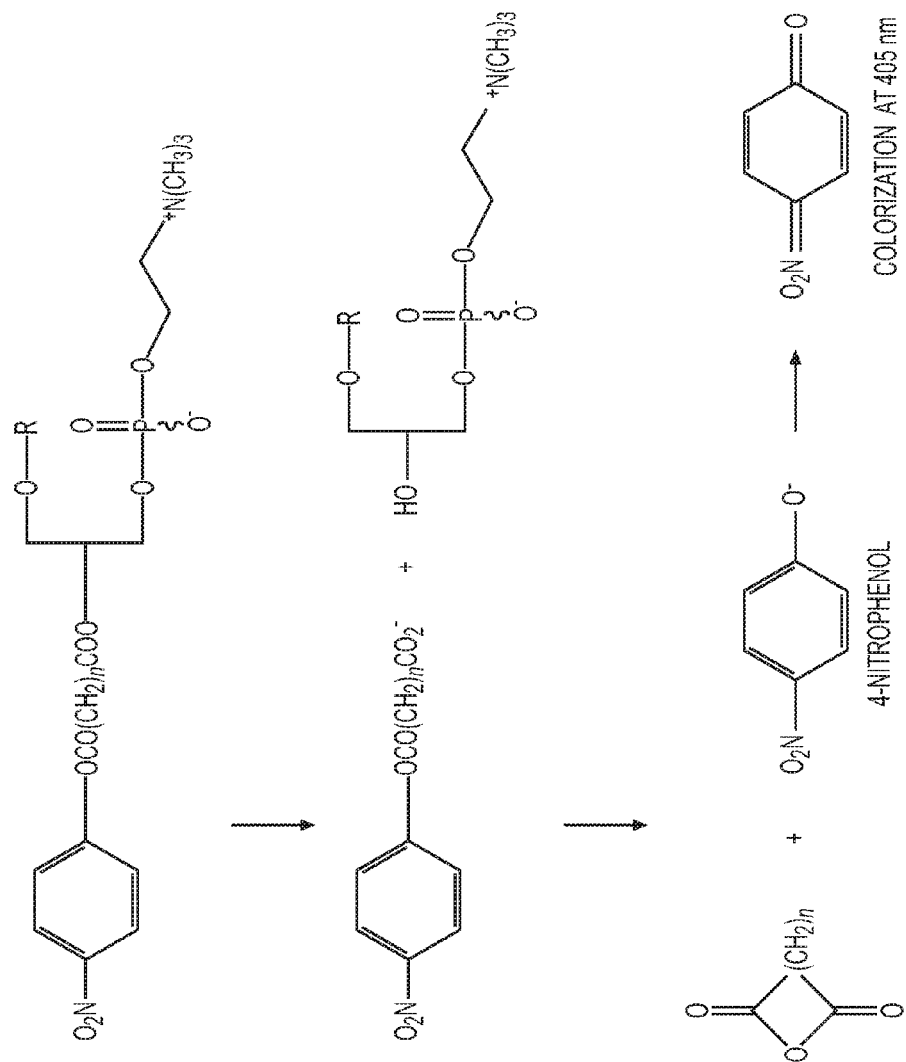
FIG. 1 illustrates one example of an Lp-PLA2 substrate that can be spectrophotometrically monitored at 405 nm to detect Lp-PLA2 activity.

"Animal" as used herein includes any human or non-human mammal, or any other vertebrate capable of naturally producing an enzyme having Lp-PLA2 activity, including Lp-PLA2, Lp-PLA2—homologs or orthologs thereof.

"Clinical trial" means human clinical trial.

"Lp-PLA2 enzyme activity" as used herein includes, but is not limited to, any enzyme activity of Lp-PLA2. This activity may include but is not limited to an Lp-PLA2 enzyme binding substrate, releasing product, and/or hydrolyzing phospholipids or other molecules.

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may comprise amino acids other than the 20 gene encoded amino acids. "Polypeptide(s)" comprise those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may comprise many types of modifications. Modifications can occur anywhere in a polypeptide, including the peptide backbone, the amino acid side-chains, and the amino or carboxyl termini. Modifications comprise, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W.H. Freeman and Company, New York (1993) and Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990) and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from post-translational natural processes and may be made by entirely synthetic methods, as well.

"Filtration" or "filtering" as used herein includes, but is not limited to, the removal of any substance from a solution and may comprise passing a solution containing the substance to be removed through filter paper, Whatman paper, cheese cloth, or a column that selectively removes said substance from solution based on its physical and/or chemical characteristics. Physical and chemical characteristics that may be used to remove a substance through filtration may include, but are not limited to, ionic charge, size, weight, polarity, and/or chemical moieties associated with the substance that make it likely to bind to the material filling the column. Filtration may comprise using gravity, vacuum, and/or centrifugation to facilitate the removal of said substance from solution.

"Scintillation cocktail" as used herein is a mixture of solutes and solvents, typically containing an organic solvent capable of solubilizing and maintaining a uniform suspension of a tissue sample for liquid scintillation. The process of liquid scintillation involves the detection of beta decay within a sample via capture of beta emissions. A scintillation cocktail mixture is designed to capture the beta emission and transform it into a photon emission which can be detected via a photomultiplier tube within a scintillation counter. Several scintillation cocktails are commercially available. It is understood that a modification of the composition of the scintillation cocktail can effect and/or optimize the detectable reading from liquid scintillation depending on the sample.

"Tissue(s)" as used herein comprises serum, cell lysate, tissue lysate, urine, blood plasma, plaque, monocytes, or macrophage cells. These tissues can be from humans, non-human mammals or other animals that naturally produces and enzyme having Lp-PLA2 activity, including Lp-PLA2, Lp-PLA2—homologs or orthologs thereof.

"Colorimetric or fluorimetrc detectable moiety" as used herein is a portion of a compound capable of producing a detectable or measurable signal. Such a signal may be measurable by, but not limited to, visible light emission or absorption, fluorescence, phosphorescence or other detectable quanta. For instance, a substrate for Lp-PLA2 may comprise a colorimetric c moiety bonded to phosphatidylcholine at the Lp-PLA2 cleavage site. When Lp-PLA2 cleaves the colorimetric moiety from phosphatidylcholine the colorimetric moiety emits a detectable signal as visible light. One non-limiting example of phosphatidylcholine bonded to a colorimetric moiety is 1-myristoyl-2-(4-nitrophenylsuccinyl) phosphatidylcholine.

Lp-PLA2 "inhibitor" or "inhibition" as used herein refers to any method, technique, condition, or compound capable of reducing or eliminating Lp-PLA2 activity, including but not limited to reducing or eliminating any of the activities of Lp-PLA2 including, but not limited to, enzyme binding substrate, releasing product, and/or hydrolyzing phospholipids or other molecules. Inhibition of Lp-PLA2 activity may be measured in a sample obtained from an animal administered an inhibitor, which is considered in vivo administration. Alternatively, an inhibitor may be added to a sample after it is obtained from an animal, which would be considered in vitro administration.

An inhibitor of Lp-PLA2 may include any appropriate inhibitor of Lp-PLA2, including Formulas I, II, III, described in greater detail below, or any other direct or indirect inhibitor of Lp-PLA2. For example, Darapladib (SB-480848), shown in Formula II, below, is a selective Lp-PLA2 inhibitor of Lp-PLA2. Diralapid, Rilapladib (shown in Formula I, below) and generally quinolone compounds (see, e.g., U.S. Pat. No. 8,575,348) and pyrimidinone compounds inhibit Lp-PLA2 (see, e.g., U.S. Pat. No. 8,637,524). Other inhibitors may include HMG-CoA reductase inhibitors (statins), including, but not limited to, atorvastatin, cerivastatin, fluvastatin, lovastatin, mevastatin, pitavastatin, pravastatin, rosuvastatin, and simvastatin. Niacin and ezetimibe ((3R,4S)-1-(4-fluorophenyl)-3-[(3S)-3-(4-fluorophenyl)-3-hydroxypropyl]-4-(4-hydroxyphenyl)azetidin-2-one), have also been identified as an inhibitors of Lp-PLA2. Other Lp-PLA2 inhibitors may include fibrates, both alone or in combination with orlistat ((S)—((S)-1-((2S,3S)-3-Hexyl-4-oxooxetan-2-yl)tridecan-2-yl) 2-formamido-4-methylpentanoate), e.g., fenofibrate (propan-2-yl 2-{4-[(4-chlorophenyl)carbonyl]phenoxy}-2-methylpropanoate), and gemfibrozil (5-(2,5-dimethylphenoxy)-2,2-dimethyl-pentanoic acid). Additionally, inhibitors may include PCSK9 inhibitors, including, but not limited to, alirocumab (REGN727), LGT209, evolocumab (AMG145), bococizumab (PF-04950615, RN316), RG-7652 (Roche/Genentech), LY3015014 (Eli Lily), ALN-PCS/02 (Alnylam Pharmaceuticals), BMS-962476 (Bristol-Myers Squibb), SPC5001 (Santaris Pharma A/S), BMS-844421/ISIS-405879 (Bristol-Myers Squibb/Isis Pharmaceuticals). Inhibitors additionally may include omega-3 fatty acids, compounds containing resolvins, and foods with high omega-3 fatty acids, including, but not limited to, omega-3 rich fish oils, salmon, and sardines Inhibitors may include foods high in anti-oxidant compounds, including, but not limited to, fresh fruits and vegetables, beans, nuts, seeds, tea, red wine, pomegranate juice, and tumeric (curcumin). Inhibitors may further include foods with high flavonoid content (e.g. dark chocolate). Inhibitors may additionally include combinations of inhibitors and molecules with the properties of multiple inhibitors, including, but not limited to, CAT 2003 (a conjugate of niacin and the omega 3 fatty acid eicosapentaenoic acid (EPA); Catabasis Pharmaceuticals).

As used herein, "reduce" or "reducing" refers to a decrease or elimination in Lp-PLA2 enzyme activity. Some non-limiting examples for the purposes of measuring reduced Lp-PLA2 activity include measuring Lp-PLA2 activity from the same animal in the presence and absence of an inhibitor of Lp-PLA2 activity. Alternatively, Lp-PLA2 activity can be measured against a standard recombinantly expressed, semi-purified or purified enzyme.

As used herein "free" or "essentially free" of Lp-PLA2 inhibitor refers to a tissue sample that contains either no Lp-PLA2 inhibitor or Lp-PLA2 inhibitor at a low enough concentration such that Lp-PLA2 activity is not inhibited by the inhibitor. For instance, if the inhibitor is present at a concentration lower than the determined dissociation constant of that inhibitor for Lp-PLA2, a tissue sample may be considered essentially free of inhibitor. A tissue sample may be considered free of Lp-PLA2 inhibitor if it is obtained from an animal prior to administration of an Lp-PLA2 inhibitor that is not produced naturally by the animal. A tissue sample may also be considered free or essentially free of an Lp-PLA2 inhibitor if it is obtained from an animal at a time after the last dose of inhibitor sufficient to ensure clearance based on pharmacokinetic profile of that inhibitor in the species of animal.

Lp-PLA2 is a known hydrolyzer of phospholipids. Lp-PLA2 can cleave phospholipids at the sn-2 position to create lyso-PC and oxidized fatty acids. PAF has a two-carbon acyl group at the sn-2 position; therefore, when PAF is hydrolyzed by Lp-PLA2, the short acyl group is cleaved as water soluble acetate from the remainder of the molecule, which is lyso-PC. A substrate possessing a colorimetric or fluorimetrc moiety can be used to measure Lp-PLA2 activity. For instance, as illustrated in FIG. 1, the substrate, 1-myristoyle-2-(p-nitrophenylsuccinyl)-phosphatidylcholine, is a PAF analogue with a 4-nitrophenyl group conjugated onto a succinyl chain at sn-2 position. Lp-PLA2 (PAF-AH) hydrolyzes the sn-2 position of the substrate, producing 4-nitrophenyl succinate. This liberation can be spectrophotometrically monitored at 405 nm and Lp-PLA2 activity determined from the change in absorption.

The methods of the present invention have been shown to demonstrate a correlation between Lp-PLA2 inhibitor concentration in a tissue sample and Lp-PLA2 activity in vitro. Furthermore, the present invention provides methods for measuring Lp-PLA2 activity over time in tissue samples from animals treated with Lp-PLA2 inhibitor. These data may be correlated with the pharmacokinetic profile of inhibitor from an animal, such as a human.

A colorimetric Lp-PLA2 activity monitoring assay has been developed using 1-myristoyl-2-(p-nitrophenylsuccinyl) phosphatidylcholine as the substrate. In vitro drug inhibition study using Lp-PLA2-specific inhibitors showed specificity of this substrate against Lp-PLA2. However, the Auto PAF AH assay provided by Azwell failed to detect drug inhibition in human subjects who received Lp-PLA2 inhibitor drugs in vivo, although the same substrate and the same buffer condition are used in the assays developed herein. Factors such as pre-incubation of plasma with assay buffer, plasma sample volume, substrate concentration, and use of buffer R2A, have been identified to contribute to in vitro drug dissociation in the assay and in turn cause the inability of the assay to detect drug inhibition in in vivo drug-bound tissue samples. These factors therefore were modified in development of new, drug-sensitive colorimetric Lp-PLA2 activity assays. Interactions between these factors have also been studied so that assay conditions could be chosen that would generate detectable in vivo drug inhibition and also offer an adequate assay dynamic range. Unlike prior art assays, the modified drug-sensitive assays described herein are able to detect inhibition and register greater than 30% inhibition at a reasonably broad dynamic range (e.g., 100-fold or greater). For example, the modified drug-sensitive assays described herein able to detect 85-95% (or more) drug inhibition in human subjects with in vivo administration of Lp-PLA2 inhibitors and therefore could be used as a monitoring assay to assess drug efficacy in the clinic. These assays also offer a dynamic range of close to 100-fold (in the examples described below, a dynamic range of greater than 100-fold, such as greater than 600-fold, are shown) and potentially is also useful as a screening assay that is capable of measurement of a broader range of Lp-PLA2 activity.

In one aspect of the present invention, a method is provided for determining inhibition of Lp-PLA2 enzyme activity in at least one tissue sample comprising the steps of preparing a solution comprising a substrate for Lp-PLA2 comprising a colorimetric or fluorometric detectable moiety; contacting at least one said tissue sample with the solution of the preparing step; and detecting Lp-PLA2 activity, wherein the tissue sample is from an animal that has been administered with Lp-PLA2 inhibitor. These methods may further comprise comparing Lp-PLA2 activity from a tissue sample obtained from an animal prior to Lp-PLA2 inhibitor administration or that is free of Lp-PLA2 inhibitor. Inhibition of Lp-PLA2 activity may be measured in a plurality of tissue samples obtained from an animal at more than one time point after administration of said Lp-PLA2 inhibitor. The substrate may be 1-myristoyl-2-(4-nitrophenylsuccinyl) phosphatidylcholine and may be used at a concentration of about 53 µM to about 1125 µM. The concentration of -myristoyl-2-(4-nitrophenylsuccinyl) phosphatidylcholine may be 440 µM or it may be 112 µM.

In one aspect of the invention, the tissue sample may be blood plasma, or it may be serum. In another aspect, the blood plasma is diluted about 3 to 9 fold with the solution of the preparing. Lp-PLA2 activity may be measured by measuring optical density of the tissue sample.

In another aspect of the present invention, the solution comprising a substrate for Lp-PLA2 further comprises a buffer and wherein the buffer is incubated with the substrate prior to contacting the substrate with said tissue sample. In another aspect, the buffer does not comprise citric acid monohydrate. In another aspect, the substrate concentration is maintained at approximately the Km of said substrate. Km of said substrate may be decreased by removing citric acid monohydrate from the buffer. When the substrate is 1-myristoyl-2-(4-nitrophenylsuccinyl) phosphatidylcholine, the substrate concentration may be about 440 µM or may be about 112 µM.

In another aspect of the present invention, the volume of plasma sample is about 15 µL to about 50 µL in a volume of about 125 µL to about 170 µL of the solution of the preparing step. In another aspect, the pH of the reaction is maintained at least about 7.5 prior to contacting the plasma sample with the solution of the preparing step.

In another embodiment of the present invention, a method is provided for determining Lp-PLA2 enzyme activity in a tissue sample obtained from an animal comprising the steps of: a) contacting 110 µL of a solution comprising: a solution comprising 90 mM 1-myristoyl-2-(4-nitrophenylsuccinyl) phosphatidylcholine contacted with a solution comprising 200 mM HEPES, 200 mM NaCl, 5 mM EDTA, 10 mM CHAPS, 10 mM sodium 1-nonanesulfonate at a pH 7.6 in a ratio of 0.66 µl to 110 µL; with at least one 25 µL tissue sample from an animal; with 25 µL each of a p-nitrophenol standard solution comprising; 4, 3, 2, 1, 0.4 or 0.2 nmol/µL p-nitrophenol in methanol; and 25 µL of phosphate buffered saline (PBS) or ddH$_2$O to make a blank; and b) determining Lp-PLA2 activity.

In one aspect, the tissue sample from animal is blood plasma. In another aspect, the animal is human. In yet another aspect, the animal has been administered an inhibitor of Lp-PLA2 prior to obtaining the tissue sample. Inhibition of Lp-PLA2 enzyme activity by said Lp-PLA2 inhibitor administered prior to obtaining said tissue sample is measured by comparing Lp-PLA2 activity of a tissue sample free of said Lp-PLA2 inhibitor.

In another embodiment of the present invention, a method is provided for determining Lp-PLA2 enzyme activity in a tissue sample obtained from an animal wherein enzyme activity is determined by: a) generating a standard curve by plotting optical density (OD) values at 405 nm for the p-nitrophenol standard solutions vs. p-nitrophenol (nmol/well); b) calculating the slope (OD/nmol) of the standard curve; c) calculating aborbance change between 3 and 1 minute ($\Delta OD_{3min-1min}$) for both solutions comprising tissue samples and blank; and d) calculating Lp-PLA2 activity using the following formula:

Lp-PLA2 activity (nmol/min/ml)=($\Delta OD_{sample}$−$\Delta OD_{blank}$)/slope($OD$/nmol)/0.025 ml=2 minutes.

In another embodiment of the present invention, a method is provided for determining Lp-PLA2 enzyme activity in a tissue sample obtained from an animal comprising the steps of: a) preparing a solution comprising 200 mM HEPES, 200 mM NaCl, 5 mM EDTA, 10 mM CHAPS, 10 mM sodium 1-nonanesulfonate at a pH 7.6; b) preparing a solution comprising 90 mM 1-myristoyl-2-(4-nitrophenylsuccinyl) phosphatidylcholine; c) preparing 100, 75, 50, 25, 10 and 5 nmol/µL stock solutions of p-nitrophenol in methanol; d) preparing working solutions for p-nitrophenol standards by diluting 40 µL of stock solutions of step c into 960 µL of methanol; e) contacting the solution of step b and the solution of step a in a ratio of 0.66 µL to 110 µL to make an assay buffer; f) adding 120 µL of assay buffer to each well in a 96-well V-bottom plate; g) adding 25 µL of each p-nitrophenol standard working solution of step d into a separate well of two columns of a 96-well flat-bottom plate; h) adding 25 µL of tissue sample from an animal per well that do not contain p-nitrophenol standards of the flat-bottom plate of step g; i) adding 25 µL of PBS or dd H$_2$O into an empty well in the flat-bottom plate for use as a blank; j) contacting 110 µL of assay buffer from the V-bottom plate to each well of the flat-bottom assay plate; k) placing the flat bottom assay plate onto a plate reader and reading at 405 nm; l) generating a standard curve by plotting optical density (OD) values for the standard solutions vs. p-nitrophenol (nmol/well); m) calculating the slope (OD/nmol) of the standard curve; n) calculating absorbance change between 3 and 1 minutes ($\Delta OD_{3min-1min}$) for both test samples and the blank; and o) calculating Lp-PLA2 activity using the following formula:

$$Lp\text{-}PLA2 \text{ activity (nmol/min/ml)}=(\Delta OD_{sample}-\Delta OD_{blank})/\text{slope}(OD/nmol)/0.025 \text{ ml}/2 \text{ minutes}.$$

Calculating the absorbance change can be performed at various intervals including, but not limited to, 2 and 0 minutes, 1 and 0 minutes and about 15-second intervals measured over about a 10 minute reaction time.

The following examples illustrate various aspects of this invention. These examples do not limit the scope of this invention which is defined by the appended claims.

EXAMPLES

Unless otherwise indicated all plasma samples were collected from human and are human plasma. Unless otherwise indicated, plasma samples for the following examples were collected as follows. Blood was collected into EDTA-containing tubes. The tubes were centrifuged at 1730*g for 10 minutes. Plasma was drawn off with transfer pipettes into tubes and stored at −80° C.

In experiments in which Lp-PLA2 inhibitor was added to tissue samples in vitro the following procedure was used, unless otherwise indicated. A 9 mg/mL stock solution was prepared in PBS. A series of working dilutions were prepared in PBS to give concentrations of 90000, 9000, 6000, 3000, 1000, 500, 200, 100, and 0 ng/mL. One microliter of each working dilution was added to every 100 ul of plasma or serum followed by incubation at 37° C. for 1 hour. The final concentrations of Lp-PLA2 inhibitor in plasma or serum were: 900, 90, 60, 30, 10, 5, 2, 1, and 0 ng/mL.

Example 1

The Auto PAF AH Assay Kit

The Auto PAF AH assay kit, manufactured by Azwell (Osaka, Japan), is commercially available in the United States through Karlan Research Products Corporation (Santa Rosa, Calif.). This assay was evaluated on an Olympus Au640 clinical chemistry analyzer and is described in this Example 1.
Materials
  Azwell Auto PAF-AH Assay Kit:
    R1: 200 mM HEPES, 200 mM NaCl, 5 mM EDTA, 10 mM CHAPS, 10 mM sodium 1-nonanesulfonate, pH 7.6
    R2A: 20 mM citric acid monohydrate, 10 mM sodium 1-nonanesulfonate, pH 4.5 R2B: 90 mM 1-myristoyl-2-(4-nitrophenylsuccinyl) phosphatidylcholine
Assay Procedure
  1. Enter assay parameters from the following table into the Olympus Au640 analyzer, and create a PAF AH assay program:
    Sample volume: 2 µL
    Reagent 1: 240 µL
    Reagent 2: 80 µL
    Wavelength (main): 410 nm
    Wavelength (sub): 480 nm
    Method: Rate
    Point 1 (FST): 14
    Point 1 (LST): 21
    Calibration Type: MB Formula: Y=AX+B
    Counts: 2
    MB Type Factor: 11595
  2. Prepare the following reagents:
    R1: Use this buffer solution as supplied in Azwell Auto PAF AH assay kit. Store at 4° C. Protect from light.
    R2: Prepare the R2 working solution by mixing R2A and R2B (supplied in Azwell Auto PAF AH assay kit) in the proportion of 19:1. Store at 4° C. Protect from light.
  3. Aliquot 30 µL or more of each plasma sample into a 2 mL Sarstedt micro-tubes (Sarstedt Incorporation, part No. 72.694.007). Briefly centrifuge to spin down fibrin clots/particles in the plasma.
  4. Place Sarstedt tubes containing plasma samples onto sample tubes that fit the instrument. Run plasma samples through the Au640 analyzer. After choosing the PAF AH assay program, the analytical procedure described below is performed automatically:
    Test sample (2 µL)+R1 (240 µL), 37° C., 5 minutes [0-5 minutes]
    Add R2 (80 µL), 37° C., 5 minutes [5-10 minutes]
    Measure the absorbance at 410 nm and 480 nm [6-8 minutes]
    Calculate PAF AH activity (IU/L)
  5. Include Bio-Rad Lyphochek Assayed Chemistry Control Level 1 and Level 2 (C-310-5 and C-315-5, Bio-Rad, Hercules, Calif.) as quality controls in each run. The Lp-PLA2 activity values for these two controls are within the range of normal human plasma Lp-PLA2.

Example 2

High Throughput Radiometric Assay for Measurement of Lp-PLA2 Activity

A high throughput radiometric assay was developed for measuring Lp-PLA2 activity in a sample. This assay is fully described in WO2005/001416. A summary of a high throughput radiometric activity assay is provided in this Example 2.
Equipment
  Scintillation Counter TopCount Microplate Scintillation and Luminescence Counter, Perkin-Elmer (formerly Packard), CA Centrifuge Allegra 25R benchtop centrifuge, Beckman Coulter, Calif. Plate shaker Lab-Line Titer Plate Shaker (VWR cat #57019-600) Oven Barnstead/Thermolyne, series 9000, temperature range 10-250° C. (VWR cat#52205-065) 12-channel Pipettors BRAND Transferpette®-12, BrandTech Scientific, Inc., Essex, Conn.
Material
  Polypropylene Plates Costar* Brand 96-Well Plates, Polypropylene, Nonsterile, Without Lids, Costar 3365, Corning, Inc., Corning, N.Y. (VWR cat #29444-104) PicoPlate Plates 96-Well white solvent-resistant microplates, Perkin Elmer Life Sciences, Inc, Boston, Mass. (cat #6005162)
Reagents
  HEPES (4-(2-hydroxyethyl)-1-piperazineethane sulfonic acid) Sigma Chemical Co., St. Louis Mo. (Cat #119897100)
  Sodium Chloride, Sigma Chemical Co., St. Louis Mo. (Cat # S5150; 5.0 M)
  EDTA, Sigma Chemical Co., St. Louis Mo. (Cat # E7889; 0.5 M)
  $^3$H-Platelet Activating Factor, 1-O-Hexadecyl-[acetyl-3H (N)], (3H-PAF)—NEN Life Science Products, Roxbury, Mass. (Cat # NET-910, supplied as an ethanol solution, typically 0.1 mCi/mL; 250 uCi)

C16-PAF, (1-hexadecyl-2-acetyl-sn-glycero-3-phosphocholine): Avanti Polar Lipids, Alabaster, Ala. (Cat #878110; 5.0 mg/ml)

MicroScint-20: Perkin Elmer Biosciences, Boston, Mass. (cat #6013621)

Fatty acid-free bovine serum albumin (BSA): Sigma Chemical Co., St. Louis Mo. (Cat # A0281; 1.0 gm)

Trichloroacetic acid (TCA): Sigma Chemical Co., St. Louis Mo. (Cat #T9159)

Assay Buffer
  100 mM Hepes, pH 7.4
  150 mM NaCl
  5 mM EDTA
  Store it at room temperature Procedures
  1. Prepare a $^3$H-PAF working solution (for 100 reactions):
    a) Aliquot 480 µl $^3$H-PAF (10 µM=0.1 mCi/ml at 10.0 Ci/mmol) and 125.3 µl of [C16]PAF (5.0 mg/ml; MW: 524) to a tube;
    b) Mix and air dry in the hood;
    c) Resuspend the dried pellets in 12.0 ml of assay buffer giving working solutions of 100 µM PAF (i.e. $^3$H-PAF at 0.4 µM and cold [C16]PAF at 99.6 µM);
  2. Aliquot 5 µL of assay buffer (for Total counts and Blanks; n=8) or plasma samples in duplicates into a 96-well plate;
  3. Equilibrate the plate to 21° C.;
  4. Add 100 µL of the $^3$H-PAF solution to each well, mix and incubate the plate at 21° C. for 5 minutes;
  5. Add 50 µL of ice-cold BSA solution (50 mg/ml) to all wells, mix and incubate the plate in a refrigerator for 5 minutes;
  6. Add 25 µL of ice-cold TCA solution (56%) to each well, mix and incubate the plate in a refrigerator for 15 minutes;
  7. Centrifuge the plate at 6,000 g for 15 minutes at 4° C.;
  8. Aliquot 45 µL of the supernatants to a 96-well polystyrene plate;
  9. Add 10 µL of $^3$H-PAF working solution to 6 Total Counts wells;
  10. Add 200 µL of MicroScint-20 scintillation cocktail to each well;
  11. Cover the plate with a plate tape and vortex mix at max speed for 10 minutes;
  12. Get static off the plate by wiping with a wet tissue and drying with another clean one;
  13. Count with a TopCount scintillation counter for 2 minutes each; and
  14. Calculate Lp-PLA2 activity:

Lp-PLA2 activity (nmoles/min/ml)=160*(CPM$_{45\ \mu l\text{-}supe}$-CPM$_{Blanks}$)/(CPM$_{10\ \mu l\text{-}spiking}$-CPM$_{Blanks}$)

Where CPM$_{45\ \mu l\text{-}supe}$ is the average count from each sample
CPM$_{Blanks}$ is the average count of the Blanks
CPM$_{10\ \mu l\text{-}spiking}$ is the average count of the Total Counts Example 3

Correlation of Auto PAF AH Assay and High Throughput Radiometric Assay

A panel of 120 plasma samples from healthy human volunteers was assayed for Lp-PLA2 activity at three clinics using the high-throughput radiometric assay described in Example 2. The same sample panel was assayed using Azwell's Auto PAF AH assay described in Example 1 on the Olympus Au640 analyzer. Correlation was obtained against data generated on the same panel of samples by the high throughput radiometric assay. Correlation coefficients (r) were 0.96, 0.94, and 0.95 for Auto PAF AH vs. the radiometric activity assay at the three clinics, respectively. The average CV between duplicates was 2.14% for the Auto PAF AH assay.

Example 4

Low Throughput Radiometric Assay

A low throughput radiometric assay capable of measuring Lp-PLA2 activity is provided below.

Materials
  Scintillation Vials (Wheaton Omni Vials, Millville, N.J. (Cat #225402)); Scintillation Fluid (EcoLite™, ICN, Costa Mesa, Calif. (Cat #882475))

Equipment
  Beta Counter (Beckman Liquid Scintillation Counter, LS 5000TA, Beckman Instruments, Fullerton, Calif.); Water Bath (Fisher Scientific, Edison, N.J. Microcentrifuge Jouan Inc., Winchester, Va., Model No. A-14)

Reagents
  HEPES (4-(2-hydroxyethyl)-1-piperazineethane sulfonic acid)—Sigma Chemical Co., St. Louis Mo. (Cat # H 9136)
  Sodium Chloride—Sigma Chemical Co., St. Louis Mo. (Cat # S 7653)
  Chloroform—Aldrich Chemical Co., Milwaukee, Wis. (Cat #36, 692-7)
  Methanol—Aldrich Chemical Co., Milwaukee, Wis. (Cat #27, 047-4)
  $^3$H-Platelet Activating Factor, 1-O-Hexadecyl-[acetyl-$^3$H (N)], ($^3$H-PAF)—NEN Life Science Products, Roxbury, Mass. (Cat # NET-910, supplied as an ethanol solution, typically 0.1 mCi/mL)
  C16-PAF, (1-hexadecyl-2-acetyl-sn-glycero-3-phosphocholine)—Avanti Polar Lipids, Alabaster, Ala. (Cat #878110, supplied as 5 mg/mL CHCl$_3$ solution)

Assay Buffer
  HEPES/NaCl Buffer: 50 mM HEPES, 150 mM NaCl, pH 7.4 at 37° C.

Assay Solutions
  $^3$H-PAF working solution: Pipette 5 µCi (typically 50 µL of the solution supplied by the vendor) of H-PAF stock solution into a 1.4 mL glass vial. Add 340 ug (68 µL of a 5 mg/mL solution) of C16-PAF. Evaporate to dryness under a gentle stream of nitrogen gas in a fume hood. Reconstitute with 1.3 mL of HEPES/NaCl buffer. This will prepare sufficient working solution for approximately 62 assay tubes.

Assay Master Mix: In a 15 mL polypropylene tube, combine 7.3 mL of HEPES/NaCl buffer and 1.1 mL of $^3$H PAF working solution. In the final reaction mixture, after addition of the plasma sample, the final concentration of PAF (unlabelled C16-PAF+$^3$H-PAF) is 50 uM (the 200 µL reaction volume contains 10 nmols PAF).

For testing the inhibition of LpPLA2 activity in plasma, the assay was performed as follows:

(1) 110 µL HEPES/NaCl buffer+20 µL of appropriate working dilution of Lp-PLA2 inhibitor+50 µL of plasma sample were added to a 1.5 mL microcentrifuge tube and incubated at 37° C. for 15 minutes.

(2) 20 µL of 3H-PAF working solution was added and the samples were incubated at 37° C. for 30 seconds.

(3) Reactions terminated by the addition of 600 µL of CHCl$_3$/CH$_3$OH and processed by the assay procedures described herein.

Assay Procedures

1. Thaw plasma samples and place in 37° C. water bath to temperature equilibrate.
2. Add 150 μL of assay master mix to 1.5 mL polypropylene tubes and place in 37° C. water bath. Allow 5 minutes for temperature equilibration.
3. Add 50 μL of plasma sample or 50 μL of HEPES/NaCl buffer for buffer blanks (all samples are assayed in duplicate) to appropriate tubes containing assay master mix, vortex briefly, and incubate for 30 seconds in the 37° C. water bath.
4. Stop reaction by addition of 600 μL of $CHCl_3/CH_3OH$ solution and vortex well.
5. Just prior to centrifuging, briefly re-vortex the samples. Separate organic and aqueous phases by centrifugation in a microcentrifuge at maximum speed for 2 minutes.
6. Collect 250 μL of the upper, aqueous phase and transfer to a new 1.5 mL polypropylene tube.
7. Add 250 μL of $CHCl_3$ and vortex well.
8. Separate organic and aqueous phases by centrifugation in a microcentrifuge at maximum speed for 1 minute.
9. Collect 150 μL of the upper, aqueous phase and transfer to a 7 mL scintillation vial.
10. Add 2 mL of EcoLite™ or equivalent liquid scintillation fluid.
11. Count samples in liquid scintillation counter using a counting program that has been set up to determine cpm, counting efficiency, and dpm.
12. For determination of total radioactivity in the reaction, duplicate 150 μL aliquots of the assay master mix are counted.

Data Reduction and Analysis

Either cpm or dpm values may be used for calculation of Lp-PLA2 activity. If the counting efficiency is the same for the samples, buffer blanks, and total radioactivity vials, cpm values may be used. If different counting efficiencies are observed, dpm values should be used. For all of the results in this report, dpm values were used for activity calculations. The following equation is used to calculate LpPLA2 activity (reported as nmols/min/mL) from the raw data:

$$((x-y)/z)*40$$

where, x=cpm (or dpm) of plasma sample x 1.65 (This corrects for the total volume of the aqueous phase in each extraction. This correction is necessary since only a portion of the aqueous phase is collected after each of the extractions.) y=cpm (or dpm) of buffer blanks x 1.65 (average of duplicate determinations) z=cpm (or dpm) of total radioactivity samples divided by 10 (there are 10 nmols of PAF in each reaction tube (average of duplicate determinations) 40=factor to adjust results to nmol/min/mL (each reaction is for 30 seconds and the volume of plasma used in each reaction is 50 uL).

Example 5

Comparison of Inhibition of Lp-PLA2 Activity Measured by the Auto PAF AH Assay and Low Throughput Radiometric Assay Plasma was collected from six human subjects at different timepoints after in vivo drug administration of an Lp-PLA2 inhibitor during a clinical trial. Subjects #17 and #18 were dosed with 120 mg of Formula I, described below and shown in FIG. 4A, subjects #24 and #25 with 180 mg, and subjects #21 and #22 with 240 mg. Subjects #21 and #25 also received placebo on a different day. Lp-PLA2 activity was measured by the low throughput radiometric assay, described in Example 4, and >90% inhibition was observed with all six drug-treated subjects. However, Lp-PLA2 inhibition was not apparent when measured by the Auto PAF AH assay, as described in Example 1. The Auto PAF AH assay is insensitive to in vivo drug inhibition of Lp-PLA2. See FIG. 2 (Table 1) below.

Inter-run and within-run variability for the Auto PAF AH assay on the Olympus Au640 has been consistently low with CV less than 5% between replicates. In this experiment, the average CV between duplicates was 2% for placebo samples and 3% for all drug samples. However, Lp-PLA2 activity measured by the Auto PAF AH assay fluctuated over time for both drug and placebo subjects. Similarly, radiometric activity values for the placebo subjects fluctuated over time with a higher % CV compared with the Auto PAF AH assay. See FIG. 3 (Table 2). Observed variability in Lp-PLA2 activity for the placebo subjects appears to be biological variability.

Figure 4A:
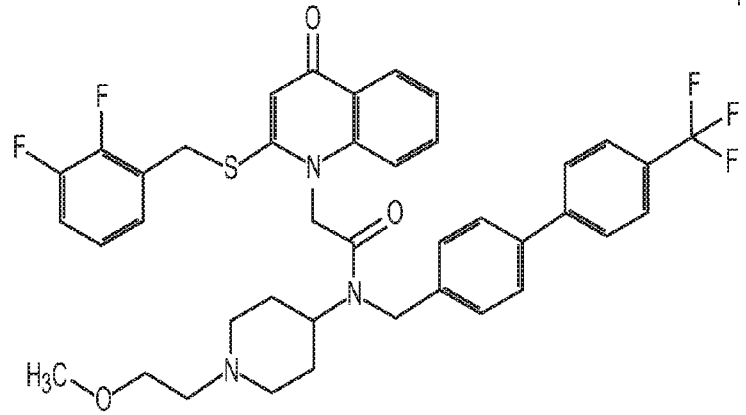
FIGS. 4A, 4B and 4C illustrate chemical formulas I, II and III, respectively. Formulas I, II and II are examples of Lp-PLA2 inhibitors. Formula 1 is 2-(2-(3,4-Difluorophenyl) ethyl)-1H-quinoline-4-1-yl N-(4'-trifluoromethylbiphenyl-4-ylmethyl)-acetamide bitartrate; is presented below and is described in WO 02/30904. Formula II is 1-(N-(2-(Diethylamino)ethyl)-N-(4-(4-trifluoromethylphenyl)benzyl)-aminoc-arbonylmethyl)-2-(4-fluorobenzyl)thio-5,6-trimethylenepyrimidin-4-one bitartrate, and is described in WO 01/60805. Formula III is 1-(N-(2-(Diethylamino)ethyl)-N-(4-(4-trifluoromethylphenyl)benzyl)aminocarbonylmethyl)-2-(4-fluorobenzyl)thio-5-(1-methylpyrazol-4-ylmethyl)pyrimid-in-4-one is described in WO 00/66567.

Formula I, shown in FIG. 4A, is 2-(2-(3,4-Difluorophenyl)ethyl)-1H-quinoline-4-1-yl N-(4'-trifluoromethylbiphenyl-4-ylmethyl)-acetamide bitartrate and is described in WO 02/30904.

Example 6

Figure 4B:
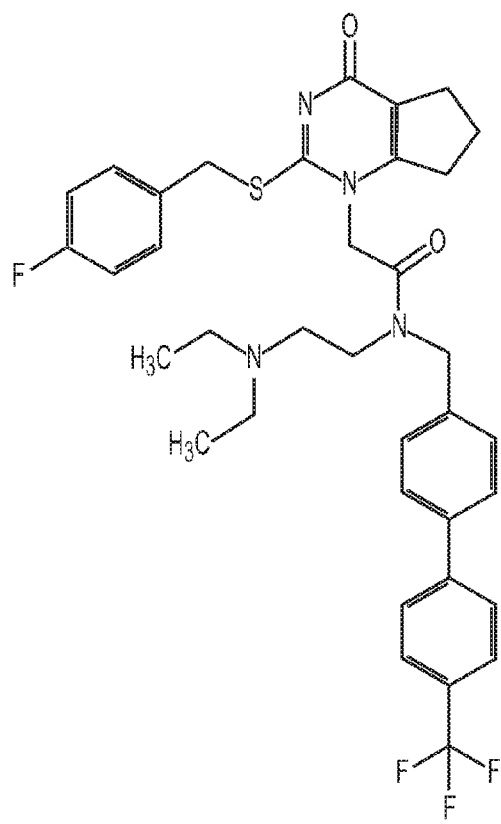

Comparison of Inhibition of Lp-PLA2 Activity Measured by the Auto PAF AH Assay and Low Throughput Radiometric Assay Plasma samples were evaluated from eight subjects who received 100 mg of a second Lp-PLA2 inhibitor during a clinical trial. The Lp-PLA2 inhibitor used in the study, 1-(N-(2-(Diethylamino)ethyl)-N-(4-(4-trifluoromethylphenyl)benzyl)-aminoc-arbonylmethyl)-2-(4-fluorobenzyl) thio-5,6-trimethylenepyrimidin-4-one bitartrate, is shown in FIG. 4B and referred to as Formula II and is described in WO 01/60805.

Four of the eight subjects also received placebo on a different day.

Greater than 90% inhibition of Lp-PLA2 activity was observed using the low throughput radiometric assay for in vivo administration of the Lp-PLA2 inhibitor. However, no inhibition was measured with the Auto PAF AH assay (see FIG. 5, showing Table 3). Lp-PLA2 activity values fluctuated for both the drug and placebo subjects as measured by Auto PAF AH assay apparently due to biological fluctuation.

Example 7

Substrate Specificity Testing

A manual colorimetric Lp-PLA2 activity assay was developed using the substrate 1-myristoyl-2-(p-nitrophenylsuccinyl) phosphatidylcholine manufactured by Azwell (Osaka, Japan). This assay is a corresponding microtiter-plate version of the Auto PAF AH Assay compatible with a spectrophotometric plate reader. This manual assay was used to evaluate the physical properties of the substrate. Presented here are data on substrate specificity.

Materials

R1: 200 mM HEPES, 200 mM NaCl, 5 mM EDTA, 10 mM CHAPS, 10 mM Sodium 1-nonanesulfonate, pH 7.6, Store at 4° C.

R2A: 20 mM citric acid monohydrate, 10 mM sodium 1-nonanesulfonate, pH 4.5,

R2B: 1-myristoyl-2-(4-nitrophenylsuccinyl) phosphatidylcholine, 90 mM p-nitrophenol: Sigma-Aldrich Chemical Co., St. Louis, Mo. (Cat #1048-25G)

Ethanol: Sigma-Aldrich Chemical Co., St. Louis, Mo. (Cat #7023)

Methanol: VWR International, West Chester, Pa. (Cat # EM-MX0482-6)

Reagent Preparation

R2: Mix R2A and R2B in ratio of 10:1. Store at 4° C. for no longer than two weeks before use.

p-Nitrophenol standards: Make 1M of 4-nitrophenol solution in Methanol. Dilute 100 µL, 75 µL, 50 µL, 25 µL, 10 µL, 5 µL of the 1M solution in 1 mL of Methanol to make 100, 75, 50, 25, 10, and 5 nmol/µL stock solution respectively. Make working solution for each standard by diluting 100 µL of stock solution into 900 µL of methanol (1:10 dilution). Store both stock and working solution at 4° C.

Assay Procedure

1. Set temperature of the plate reader (SPECTRAmax® PLUS$^{384}$UV/VIS Microplate Spectrophotometer, Molecular Devices, Sunnyvale, Calif.) at 21° C.
2. Add 120 µL of R1 into each well in a 96-well flat-bottom assay plate (Costar 3595, Corning, Inc., Corning, N.Y.) using a multi-channel pipettor.
3. Add 10 µL of p-nitrophenol standard working solution into each of the duplicate wells in Column 1 and 2. Use 7 standard points for generating a standard curve: 0, 5, 10, 25, 50, 75, 100 nmol/well. Leave well 1H and 2H for blank controls.
4. Add 5 µL of plasma individually into each well. Use duplicate for each sample. Set up blank controls by adding 5 µL of ddH$_2$O instead of plasma into well 1H and 2H. Mix the plate well by hand.
5. Incubate the plate at 37° C. for 5 minutes.
6. Cool the plate at 21° C. in the plate reader for 5 minutes.
7. Take the plate out from the plate reader. Add 40 µL of R2 into each well using a multi-channel pipettor, changing tips after each addition. Time the start of R2 addition.
8. Add 2 µL of ethanol into each well using a multi-channel pipettor, changing tips after each addition. The purpose of this step is to rid of all the air bubbles generated in wells. The duration between first R2 addition and plate reading in Step #9 is 4 minutes.
9. Read the plate at 405 nm for 20 minutes with a 2-minute interval. Include a 2-minute auto-mixing before reading the plate.

Activity Calculation

1. Generate a standard curve by plotting average OD values at 0 and 20 minutes ($OD_{0min}$ and $OD_{20min}$) for the 7 standards vs. p-nitrophenol (nmol/well). Calculate the slope of the standard curve.
2. Calculate ΔOD values for each blank well between 2 and 4 minutes ($OD_{4min}-OD_{2min}$) and average the two ΔOD values for the blanks
3. For each sample well, calculate ΔOD values between 2 and 4 minutes and then Lp-PLA2 activity (nmol/min/ml)= (ΔOD$_{sample}$–ΔOD$_{blank}$)/slope (OD/nmol)/0.005 ml/2 minutes.
4. Calculate an average activity value for duplicate sample wells.

Results

Figure 4C:
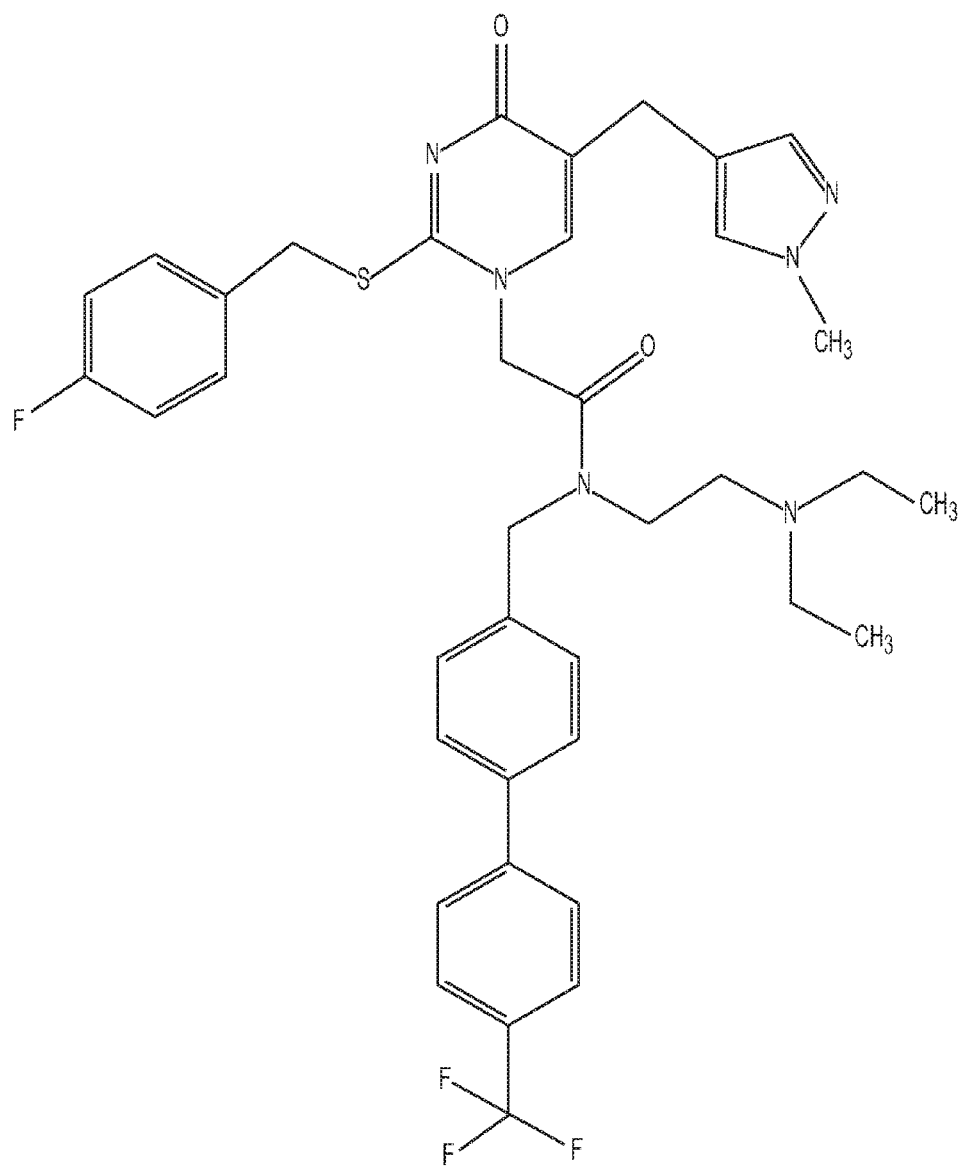

Substrate specificity against Lp-PLA2 was assayed by using two Lp-PLA2 inhibitor compounds; Formula II, which is described in Example 6, and Formula III, which is shown in FIG. 4C. Formula III is 1-(N-(2-(Diethylamino)ethyl)-N-(4-(4-trifluoromethylphenyl)benzyl)aminoca-rbonylm- ethyl)-2-(4-fluorobenzyl)thio-5-(1-methylpyrazol-4-ylm-ethyl)pyrimid-in-4-one is described in WO 00/66567.

Plasma samples from four healthy patients were incubated in vitro with increasing amount of Formula III. For addition of the inhibitor solution to the reaction mixtures, a 100 mM stock solution was prepared in DMSO. A series of 1:10 working dilutions were prepared in DMSO to give concentrations which ranged between 10 mM and 0.01 nM. One microliter aliquots of each working dilution were added in each reaction. The final concentrations of Lp-PLA2 inhibitor were (in nM) 60,000, 6,000, 600, 60, 6, 0.6, 0.06, 0.006, 0.0006, 0.00006 and 0.

All four plasma demonstrated decreasing Lp-PLA2 activity as shown in Table 4 (FIG. 6). Inhibition achieved by Formula III in all four samples reached over 90%, comparable to the natural Lp-PLA2 substrate PAF used in the radiometric activity assay. Formula II also showed over 90% inhibition of the substrate hydrolysis when incubated in vitro in the same four plasma samples.

The assay buffer used in above experiments has high content of detergent (7.5 mM CHAPS and 10 mM Sodium 1-nonanesulfonate). When detergent was eliminated from the assay, Formula III only inhibited about 65% of hydrolysis activity in plasma sample #10. When detergent was added in the parallel experiment inhibition of more than 95% was reached. Therefore, it appears that this substrate is specific to Lp-PLA2 only when it is assayed in the presence of buffer comprising detergent, as shown in Table 5 (FIG. 7).

Example 8

Modified Drug Sensitive Colorimetric Assay for Measurement of Lp-PLA2 Activity

For the Auto PAF AH assay, plasma samples are diluted about 160-fold and the substrate is used at a concentration higher than its Km. It appears that when the concentration of substrate is higher than its Km the substrate competes with drug bound to Lp-PLA2 and promotes drug dissociation from the enzyme. For instance, the substrate concentration used in the Auto PAF AH assay is 1100 µM, which is more than 5 times higher than its Km (Km is about 200 µM when plasma is used as the enzyme source and assayed by Auto PAF AH protocol, see Example 1). Pre-incubation of plasma with buffer R1 in Auto PAF AH assay also appears to promote drug dissociation before the start of assay reaction. Therefore, the assay of the present invention was modified by using higher plasma sample volumes and lower substrate concentrations compared with the Auto PAF AH assay. Additionally, the pre-incubation step of plasma with R1 prior to substrate addition was eliminated. Moreover, elimination of buffer R2A increased reaction rates, which in turn enabled the use of lower substrate concentrations and a shorter assay incubation time during which drug dissociates compared with the Auto PAF AH assay Materials R1: 200 mM HEPES, 200 mM NaCl, 5 mM EDTA, 10 mM CHAPS, 10 mM sodium 1-nonanesulfonate, pH 7.6

R2B: 90 mM 1-myristoyl-2-(4-nitrophenylsuccinyl) phosphatidylcholine p-nitrophenol: Sigma-Aldrich Chemical Co., St. Louis, Mo. (Cat #1048-25G)

Reagent Preparation

Assay buffer: Mix R2B and R1 in a ratio of 0.66 µL to 110 µL. Store on ice or at 4° C. Prepare immediately before use.

p-Nitrophenol standards: Prepare 1M p-nitrophenol in methanol. Dilute 100, 75, 50, 25, 10 and 5 µL of 1M p-nitrophenol to 1 mL in methanol to prepare 100, 75, 50, 25, 10 and 5 nmol/μL stock solutions, respectively. Prepare working solutions for each standard by diluting 40 μL of stock solution into 960 μL of methanol (1:25 dilution). Store stock and working solutions at 4° C.

Assay Procedure

1. Add 120 μL of assay buffer to each well in a 96-well V-bottom plate (Costar 3897, Corning, Inc., Corning, N.Y.) using a multi-channel pipettor or robot.

2. Add 25 μL of p-nitrophenol standard working solution into duplicate wells in columns 1 and 2 on another 96-well flat-bottom plate (Costar 9017, Corning, Inc., Corning, N.Y.). Use 7 standard points for generating a standard curve: 0, 5, 10, 25, 50, 75, 100 nmol/well. Add 25 μL of PBS into well 1H and 2H for blank controls.

3. Briefly centrifuge plasma to spin down fibrin clot/particles. Add 25 μL of plasma per well in columns 3-12 on the same flat-bottom plate containing p-nitrophenol standards. Use duplicates for each sample 4. Use a multi-channel pipettor or a robot to transfer 110 μL of assay buffer from the V-bottom plate to the flat-bottom assay plate containing plasma samples and p-nitrophenol standards. A Zymark RapidPlate (Caliper Life Sciences, Hopkinton, Mass.) can perform this step without generating bubbles in the wells. Other transfer methods may generate bubbles due to the high detergent content of R1. A small volume of ethanol can be used to eliminate air bubbles.

5. Immediately place the assay plate onto the plate reader (SPECTRAmax® PLUS$^{384}$UV/VIS Microplate Spectrophotometer, Molecular Devices, Sunnyvale Calif.) and auto-mix for 15 seconds.

6. Read the plate at 405 nm for 10 minutes at 15-second intervals at room temperature. The duration between the start of enzymatic reaction (addition of assay buffer to the assay plate) and completion of the first absorbance reading is 1 minute.

The assay may be performed at room temperature. More stringent temperature control may be required if room temperature fluctuates within or between labs.

Activity Calculation

1. Generate a standard curve by plotting average OD values at 0 and 10 minutes ($OD_{0min}$ and $OD_{10min}$) for the seven standards vs. p-nitrophenol (nmol/well). Calculate the slope of the standard curve.

2. Calculate Change in (ΔOD) values for each blank well between 1 and 3 minutes ($OD_{3min}$-$OD_{imm}$) and average the two ΔOD values for the blanks 3. For each sample well, calculate ΔOD values between 1 and 3 minutes and then Lp-PLA2 activity (nmol/min/ml)= ($ΔOD_{sample}$-$ΔOD_{blank}$)/slope (OD/nmol)/0.025 ml/2 minutes.

4. Calculate an average activity value for duplicate sample wells.

Example 9

Comparison of Radiometric Measurement Versus Modified Drug Sensitive Colorimetric Measurement of Lp-PLA2 activity in the Presence of Lp-PLA2 Inhibitor Lp-PLA2 activity from blood plasma samples obtained from a healthy human subject administered an Lp-PLA2 inhibitor was measured using the high throughput radiometric assay described in Example 2 and the methods of Example 8 with the following minor changes. The volume of plasma used per well was 25 μL. Substrate concentration was 1125 μM and, 2 μL of substrate solution R2B was mixed in 40 μL of R2A before further mixing with 95 μL of R1 to make the assay buffer. Blood plasma samples were collected at five timepoints after dosing (0.5, 1.0, 6.0, 48 and 96 hours post dosing). Both radiometric and colorimetric assays were used to determine Lp-PLA2 activity as well as percent inhibition in each sample as shown in Table 6. As shown in Table 6 (FIG. 8), percent inhibition of Lp-PLA2 activity as measured by a radiometric assay showed peak inhibition as about 94% one hour after dosing while a modified drug sensitive colorimetric assay showed peak inhibition at the 6-hour timepoint with about 64% inhibition in activity. These data demonstrate that both methods can be used to measure the inhibition of Lp-PLA2 activity in samples obtained from an animal that has been administered an Lp-PLA2 inhibitor. Blood samples from humans are considered to be essentially free of Lp-PLA2 inhibitor 96 hours post dosing.

Example 10

Testing of Plasma Samples from a Clinical Study for Lp-PLA2 Inhibition

Four human subjects recruited in a clinical trial of a novel Lp-PLA2 inhibitor, Formula I (see Example 5) received different doses of the drug. Drug dose for Subject #13, #36, #24, and #41 was 80 mg, 120 mg, 180 mg, and 240 mg, respectively. Plasma was collected at 0, 0.5, 1, and 3 hours after drug administration. Lp-PLA2 activity of these plasma samples was assayed by the low throughput radiometric assay described in Example 4, the Auto PAF AH assay, described in Example 1, and modified drug-sensitive colorimetric assay, which is described in this Example 8. While the radiometric activity assay indicated >90% inhibition of Lp-PLA2 activity 3 hours after dosing in all four subjects, the Auto PAF AH assay failed to indicate drug inhibition. However, a modified drug-sensitive colorimetric assay of Example 8 indicated 85-90% drug inhibition as shown in Table 7 (FIG. 9).

Similarly, both the radiometric assay and modified drug-sensitive colorimetric assay showed a measured time-dependent effect on Lp-PLA2 activity after dosing with Lp-PLA2 inhibitor as shown in Table 8 (FIG. 10). Little effect on Lp-PLA2 activity was observed using the Auto PAF AH assay as shown in Table 8 (FIG. 10).

Although the activity values generated from radiometric and modified drug-sensitive colorimetric assay are different, correlation between the two assays is r=0.975 for these 16 clinical plasma samples. Therefore, modified drug-sensitive colorimetric assays, described herein, although using the same substrate as the Auto PAF AH assay, demonstrated ability to detect in vivo drug inhibition of Lp-PLA2 in drug-treated human subjects, while the Auto PAF AH assay did not.

Example 11

Testing of Additional Plasma Samples from a Clinical Study for Lp-PLA2 Inhibition Plasma samples were collected from ten subjects in a clinical trial for the Lp-PLA2 inhibitor of Formula I. Subjects #109, #114, #115, #142 and #145 received 50 mg of Formula I while subjects #118, #119, #121, #123 and #124 received 120 mg of the compound. Lp-PLA2 activity of these plasma samples were assayed by the high throughput radiometric assay as described in Example 4, the Auto PAF AH assay as described in Example 1, and modified drug-sensitive colorimetric assay as described in Example 8. Consistently, the Auto PAF AH assay failed to measure drug inhibition of Lp-PLA2 activity in these samples with maximal inhibition of 29% detected in subject #123. However, a modified drug-sensitive colorimetric assay of Example 8 indicated comparable drug inhibition with radiometric assay in all subjects. Inhibition values for the radiometric assay and a modified, drug-sensitive colorimetric assay agreed within 15% for all but four time (#114/12 hr, #115/12 hr, #142/0.5 hr and #142/12 hr) as shown in Table 9 (FIGS. 11 part 1, 11 part 2 and 11 part 3).

Correlation of r=0.95 was obtained between a modified, drug-sensitive colorimetric assay and the radiometric assay for the 100 samples analyzed in this study. The Auto PAF AH assay showed poor correlation with radiometric assay in these drug dosed samples (r=0.31).

Example 12

Assay Dynamic Range

Instrument Low Limit of Quantitation

Twenty-five microliters of PBS were added into 110 µL of R1 containing 0.67 µL of R2B. Sixteen replicates were prepared and randomly placed in wells across a microtiter plate. Absorbance at 405 nm was obtained and standard deviation calculated between replicates. Six times standard deviation (6*SD) was defined as the lower limit of quantitation for the microtiter plate reader (SPECTRAmax® PLUS[384]UV/VIS Microplate Spectrophotometer, Molecular Devices, Sunnyvale, Calif.). The average OD reading from 16 replicates was 0.0437 with a standard deviation of 0.0009. The lower limit of quantitation for the microtiter plate reader was defined as 6*0.0009 or a change of 0.0054 OD units during assay incubation.

Linear Detection Range of p-Nitrophenol

Serial dilutions of p-nitrophenol were prepared in methanol. Twenty-five microliters of p-nitrophenol at each concentration were added to 110 µl R1 (without R2B) in a microtiter plate. Absorbance values at 405 nm were linear between 0.05 to 125 nmol of p-nitrophenol (r=0.996). However, the blank corrected absorbance of the 0.05 nmol p-nitrophenol sample was only 0.00415, which is below the microtiter plate reader's lower limit of quantitation of 0.0054 OD as defined above. Therefore, the linear detection range of p-nitrophenol is set between 0.1 and 125 nmol of p-nitrophenol per well.

Assay Dynamic Range

Assay dynamic range was defined by using both recombinant human Lp-PLA2 protein (hrLp-PLA2) generated in-house and Lp-PLA2 protein purified from human plasma in-house.

hrLp-PLA2 was serially diluted and 25 µL of each diluted hrLp-PLA2 were assayed by a modified drug-sensitive colorimetric assay (data shown in FIG. 12, Table 10). The second least amount of hrLp-PLA2 assayed 206 ng/mL showed an activity of 1.5 nmol/min/mL. Such level of activity would only generate 0.075 nmol of p-nitrophenol in two minutes of substrate hydrolysis reaction in the current assay configuration. Therefore, it is lower than the linear detection range of the end product p-nitrophenol. hrLp-PLA2 greater than 13200 ng/mL showed plateau activity. The activity of hrLp-PLA2 between 412 to 13200 ng/mL demonstrated linearity with an R value of 0.997. Therefore, the dynamic range of this assay appears to be between 4.4 and 397 nmol/min/mL, although lower and upper limits could be further defined. (see FIG. 12, Table 10).

hLp-PLA2 purified from plasma was also serially diluted and 25 µL of each dilution were assayed by a modified drug-sensitive colorimetric assay (data shown in Table 11). The activity of purified hLp-PLA2 protein ranged between 6.25 to 1200 ng/mL demonstrated linearity with an R value of 0.97. Therefore, the dynamic range assessed using purified hLp-PLA2 appears to be between 2.47 and 363.60 nmol/min/mL, comparable to the one defined by hrLp-PLA2 (see FIG. 13, Table 11). The relatively lower upper limit of the dynamic range determined by purified hLp-PLA2 may be resulted from interference factors possibly present in the purified product and/or introduced during purification process. Limited availability of such purified protein prevents further investigation.

Example 13

Substrate Stability

Stability of the substrate in modified assay buffer (110 µL R1+0.67 µL R2B+25 µL PBS) was examined by monitoring absorbance changes every 15 minutes over 120 minutes at room temperature. Although absorbance increased slowly but consistently over 2 hours reflecting gradual substrate degradation, the change in absorbance was only 0.002 OD units per 15 minutes. Therefore, substrate degradation appears to be moderate over 2 hours under a modified assay conditions. Since the assay takes only 10 minutes to complete and activity is calculated based on a 2-minute reaction period, absorbance changes from substrate degradation are insignificant and can be blank-corrected.

Example 14

Effect of Pre-Incubation of Human Plasma with Buffer R1 on Drug-Sensitivity

In the Auto PAF AH assay, plasma is pre-incubated in buffer R1 at 37° C. for 5 minutes. This pre-incubation step may accelerate the dissociation of drug bound to Lp-PLA2 before the start of the reaction. To test whether accelerated dissociation occurs, a plasma sample from a human subject (#10) was incubated with increasing amount of Lp-PLA2 inhibitor at 37° C. for an hour. Twenty-five microliters of the in vitro Formular II drug-treated plasma was then pre-incubated with 100 µL R1 at room temperature for different times before running the assay for 10 minutes at room temperature after addition of 40 µL of R2 (final substrate concentration of 1100 µM). Pre-incubation of plasma with R1 decreased drug-inhibition especially at lower drug concentrations. The highest level of drug inhibition was obtained when R1 and R2 were premixed and added directly to plasma without pre-incubation, as shown in Table 12 (FIG. 14). Pre-incubation of plasma in R1 at 37° C. instead of room temperature further deteriorates drug inhibition.

Example 15

Effect of Substrate Concentration on Drug-Sensitivity

The substrate concentration is 1100 µM in the Auto PAF AH assay, which is more than 5 times higher than its Km (Km=200 µM when plasma is used as the enzyme source and assayed by Auto PAF AH protocol). High substrate concentrations may compete with drug binding to Lp-PLA2. To test this possibility, 25 μl, of in vitro Lp-PLA2 inhibitor Formular II treated human plasma samples were added to premixed R1 (100 μL) and R2 (40 μL) containing different amounts of the substrate. Substrate hydrolysis was immediately monitored at room temperature for 10 minutes. Lower substrate concentrations indicate greater drug inhibition. Activity values approached the lower limit of quantitation at the higher drug levels when the substrate was used at 154 μM or less due to slower hydrolysis rates. Consequently, the substrate concentration should be maintained slightly above its Km in order to drive rapid substrate hydrolysis while maintaining drug inhibition levels, as shown in Table 13 (FIG. 15).

Example 16

Effect of Human Plasma Sample Volume on Drug-Sensitivity

Two μL of plasma were assayed in a 320 μL reaction for the Auto PAF AH assay, which corresponds to a plasma dilution factor of 160-fold. High plasma dilution may promote drug dissociation from Lp-PLA2. Consequently, 5 to 50 μL of an in vitro Lp-PLA2 inhibitor Formula II treated plasma sample were diluted with varying volumes of R1 and 40 μL of R2 to a final volume of 165 μL containing 1100 μM substrate. Hydrolysis was immediately monitored at room temperature for 10 minutes. Greater drug inhibition was observed with higher plasma sample volumes, as shown in Table 14 (FIG. 16).

Example 17

Effect of Deletion of Buffer 2A on Drug-Sensitivity

In the Auto PAF AH assay, the substrate stock solution R2B is premixed in buffer R2A (20 mM citric acid monohydrate, 10 mM sodium 1-nonanesulfonate, pH 4.5), which acts as a substrate stabilizer. The substrate, after diluted in R2A, remains stable at 4° C. for 14 days. Faster hydrolysis rate was observed when R2A was omitted from the assay. For example, a colorimetric assay was performed with nmol of substrate (2 μL of R2B) and either 25 μL or 50 μL of plasma. Additionally, samples contained either 0 μL or 40 μL of R2A. All reactions were diluted to either 125 μl or 165 μL with R1. Buffer components were pre-mixed and the reaction was initiated upon human plasma addition. Substrate hydrolysis was immediately monitored at room temperature for 10 minutes. Vmax (milliOD/min) was calculated and compared among different conditions. Higher hydrolysis rates were observed upon omission of R2A, independent of plasma volume as shown in Table 15 (FIG. 17).

Since R2A has low pH of 4.5 compared with the other assay buffer components, whether addition of R2A affected the pH of the assay reaction was determined. The pH of assay reactions containing 110 μL of R1, 0.66 μL of R2B and 25 μL of either plasma or ddH$_2$O were 7.52 and 7.53, respectively. The pH dropped to 7.43 and 7.42, respectively, when 40 μL of R2A were added to these assay samples. The effect of R2A on Lp-PLA2 hydrolysis rates of the substrate is probably more than pH-related.

Elimination of R2A from the assay increased hydrolysis rates, thereby allowing the use of lower substrate concentrations and shorter assay incubation times, both of which lower drug dissociation. Lp-PLA2 activity values approached the lower limit of quantitation when 25 μL of plasma were measured using 154 μM of substrate and R2A as described in Example 14. A substrate titration experiment was repeated using 50 μL of in vitro Formula II-treated plasma (subject #10) and 75 μL of assay buffer containing only R1 and R2B (no R2A). Assays were monitored at room temperature for 10 minutes at 405 nm and Vmax and drug inhibition were calculated. Hydrolysis activity exceeded the lower limit of quantitation at 900 and 9000 ng/mL of drug even at substrate concentrations as low as 65 μM (see FIG. 18, Table 16). Consequently, R2A was eliminated and lower substrate concentrations were incorporated in a modified colorimetric activity assay.

Earlier studies indicated higher drug inhibition as the substrate concentration was lowered over 2200 μM to 273 μM in combination with 25 uL of human plasma. However, no significant effect on drug inhibition was observed when substrate concentration was lowered over 273 μM to 65 μM using 50 μL of plasma, which suggests drug dissociation is not promoted by lower substrate levels with higher plasma volumes over this range.

Example 18

Design of Experiment Software

After identifying individual factors that contribute to the drug insensitivity of the original Auto PAF AH assay, JMP software (Design of Experiment, herein "DOE") was used to design experiments investigating interactions between individual factors and to identify optimal combinations for detecting drug inhibition over an adequate dynamic range.

DOE Experiment #1

The first DOE experiment focused on four factors including buffer R1 volume (2 levels), plasma volume (4 levels), substrate concentration (8 levels) and drug treatment (2 levels). The indicated levels of substrate concentration refer to the substrate concentration in the aliquot of premixed R2B/R1 added to each reaction unless otherwise noted. Although a full factorial combination of variables would require 128 assay reactions, D-optimal design suggested 48 different combinations. These 48 reactions were performed in duplicate, using a single plasma sample with or without prior in vitro incubation with Formula II at 37° C. for an hour. Substrate was directly diluted into R1 and plasma was then added to start hydrolysis at room temperature. Vmax and drug inhibition were calculated based on absorbance readings at 405 nm over 5 minutes at room temperature.

JMP predicted that a combination of 15 μL or 25 μL of plasma and 110 μL of R1 containing 273 μM to 1100 μM substrate would indicate 90% or greater drug inhibition. This set of conditions would also yield reasonably high Vmax so that heavily drug-treated plasma would not fall below the lower limit of quantitation. The lowest substrate concentration included in this experiment, 65 μM in 110 μL of R1, was predicted to detect 93.41% drug inhibition when used with 25 μL of plasma (final substrate concentration of 53 uM). However, Vmax prediction was as low as 16.79 for the non-drug-treated sample. Such condition, although did not proceed for further optimization, could be used to assay specific sample sets that have low and narrow range of Lp-PLA2 activity.

DOE Experiment #2

The second DOE experiment focused on the conditions identified by the prior DOE experiment. It designed a full factorial combination of all variables including R1 volume (1 level), plasma volume (2 levels), substrate concentration (4 levels) and drug treatment (4 levels). Thirty-two conditions were assayed in duplicate. The assay protocol was identical to the first DOE experiment. The indicated levels of substrate concentration again refer to the substrate concentration in the aliquot of premixed R2B/R1 added to each reaction unless otherwise noted. Prediction Profiler predicted that 25 µL plasma and 110 µL of R1 containing 545 µM substrate would generate a Vmax of 76 milliOD/min for non-drug treated plasma and indicate close to 95% drug inhibition for plasma treated with 900 ng/mL of drug in vitro. Therefore, a modified, drug-sensitive assay uses 25 µL of plasma with 110 µL of R1 containing 545 µM substrate for a final substrate concentration of 440 µM in the assay.

An alternative set of conditions was also identified (15 µL of plasma and 110 µL of R1 containing 545 µM for a final substrate concentration of 475 µM in the assay) that indicated 94% drug inhibition and Vmax=53 milliOD/min for non-drug-treated plasma.

Example 19

Reaction Time

Four human plasma timepoint samples from a single subject, who was treated in vivo with Lp-PLA2 inhibitor drug, were assayed for Lp-PLA2 activity by a modified, drug-sensitive colorimetric assay containing 440 µM substrate and 25 µL of plasma (described in Example 8). The same four plasma samples were also assayed by the same assay protocol but with 50 µL of plasma and 154 µM of substrate (see FIG. 19, Table 17). The first 5 minutes of hydrolysis were monitored for each reaction and five Vmax values were calculated based on time intervals of 1, 2, 3, 4 or 5 minutes from the start of the reaction. Samples corresponding to high Lp-PLA2 inhibition (1 and 3 hour post-dose) exhibited higher Vmax values for longer assay reaction times when 25 µL plasma and 440 µM substrate were used. This suggests drug dissociation may occur under such condition where competition between drug and substrate is relatively strong. In contrast, Vmax values for 1 and 3 hour post-dose time points were independent of assay reaction time when more plasma and lower substrate was used (e.g., 50 µL plasma/154 M substrate). However, Vmax values tend to decrease with longer assay reaction times for samples with lower drug inhibition (0 and 0.5 hours) especially at higher plasma volume and lower substrate concentration as appreciable total substrate is consumed with high Lp-PLA2 activity. Therefore, assay performance is affected by at least three factors affecting three attributes: (1) High plasma volume, short incubation time and low substrate concentration promote measurement of high levels of drug inhibition; (2) Low plasma volume, short incubation time and high substrate concentration promote a high upper limit of quantitation; (3) High plasma volume, long incubation time and high substrate concentration promote sensitive lower limits of quantitation.

The implementation of robotics is recommended to shorten the time between addition of substrate into plasma and the first absorbance reading on the plate reader. Current protocol assembles and mixes an entire microtiter plate of reactions and start plate reading 1 minute after starting the first reaction on the plate. Activity calculations are based on data collected at 1 and 3 minutes in the microtiter plate reader. However, since absorbance readings are collected for 10 minutes at 15-second intervals, depending on the objective of the assay and range of activity seen with a specific sample set, shorter and/or earlier, or longer reaction time could be chosen to calculate Lp-PLA2 activity.

Example 20

Further Assay Testing

Inter-Assay Validation

Intra-assay variability was assessed using plasma samples from 10 healthy (non-fasted) human subjects. Six replicates of plasma from each subject were assayed on the same assay plate. The CV for individual subjects ranged from 2.57 to 9.14% with an average intra-assay CV of 5.36% as shown in Table 18 (FIG. 20).

Inter-Assay Variability

Inter-assay variability was assessed using plasma samples from 10 healthy human subjects (non-fasted), assayed in three separate assays on different days. The inter-assay CV for individual plasma samples ranged from 1.90 to 23.78% with an average inter-assay CV of 7.59%. Plasma from Subject #5181480 (inter-assay CV=23.78%) had a white/turbid appearance after brief centrifugation, suggesting high lipid content in the sample as shown in Table 19 (FIG. 21).

Inter-Operator Variability

Inter-operator variability was assessed using plasma samples from 10 healthy subjects assayed by three different operators on different days. The inter-operator CV for individual plasma samples ranged from 5.11 to 14.91% with an average inter-operator CV of 8.32% as shown in Table 20 (FIG. 22).

Freeze/Thaw Effect

Plasma samples are normally received and stored frozen. In the case of repeat analysis, samples are commonly subject to freeze/thaw cycles. Ten plasma samples were analyzed after each of four freeze/thaw cycles. No definitive trend in Lp-PLA2 values was observed, indicating samples may be frozen and thawed four times, as shown in Table 20 (FIG. 22).

Example 21

Higher Drug Inhibition and Assay Dynamic Range

Four hundred forty microMolar (440 µM) substrate and 25 µL of plasma sample volume were selected for use in the current modified assay protocol since they offered high detectable in vivo drug inhibition while maintaining adequate assay dynamic range. However, further lowering substrate concentration and/or increasing plasma sample volume in the assay could detect higher measurable drug inhibition in vivo at expense of assay dynamic range. Plasma samples from 5 human subjects receiving Formula II for 9 days in a clinical study were collected on day 10 at different time points. Pre-dose plasma samples for each subject on day 0 of the study were also available. When 440 µM substrate and 25 µL of plasma were used in the assay, maximal 68% drug inhibition was observed in Subject N030 at 4 hour-timepoint as shown in Table 22 (FIG. 24). Lowering substrate concentration to 112 µM while maintaining 25 µL of plasma volume increased drug inhibition to 76% at this time point. Further increase in drug inhibition to 79% at 4 hour-timepoint, was achieved with both lower substrate concentration of 112 µM and higher plasma volume of 45 µL.

Plasma samples from the other four subjects were analyzed using both 440 µM substrate/25 µL plasma and 112 µM substrate/45 µL plasma assay condition. The maximal drug inhibition detected with 440 μM substrate and 25 μL plasma was between 68% and 80% in these subjects as shown in Table 23 (FIG. 25). However, the use of 112 μM substrate and 45 μL of plasma further improved measurable drug inhibition in the same subjects with maximal inhibition between 87% and 98%. With 112 μM substrate/45 μL plasma, the absolute Lp-PLA2 activity value decreased significantly with those at highest drug inhibition points approaching lower limit of p-nitrophenol linear detection range described in Example 12. For example, the 4 hour-timepoint plasma for Subject N028 showed Lp-PLA activity of 1.31 nmol/min/mL (see Table 23). Such level of activity would only generate 0.12 nmol of p-nitrophenol in two minutes of assay time based on a modified drug sensitive colorimetric assay described in Example 8, slightly above the low end of p-nitrophenol linear detection range 0.1 nmol.

To define the assay dynamic range for using 112 μM of substrate and 45 μL of plasma, serially diluted recombinant human Lp-PLA2 protein was assayed for Lp-PLA2 activity. The activity of hrLp-PLA2 between 4.88 to 312.50 ng/mL demonstrated linearity with an R value of 0.96 (see FIG. 26, Table 24). Therefore, the dynamic range appears to be between 2.71 and 84.14 nmol/min/mL. Compared to the dynamic range between 4.4 and 397 nmol/min/mL for 440 μM of substrate and 25 μL of plasma determined in Example 12 using hrLp-PLA, 112 μM substrate/45 μL plasma, although lowering low limit of quantitation, could only offer limited assay range. Therefore, such conditions with lower substrate concentration and higher sample volume could be used when higher measurable in vivo inhibition is desired while the range of Lp-PLA2 activity for test samples is limited or could be compromised. One example such conditions could be applied to is in clinical studies for Lp-PLA2 inhibitor drugs in which most post-drug test samples demonstrate low Lp-PLA2 activity resulted from drug inhibition. Earlier and shorter reaction time could be considered to use in activity calculation to improve assay dynamic range when such conditions are used.

The assay dynamic range of 2.71-84.14 nmol/min/mL determined by hrLp-PLA2 was calculated based on absorbance change between 3 minutes and 1 minute after the start of reaction. When absorbance differences between 1 minute and 0 minutes of the reaction were used to calculate Lp-PLA2 activity from the same data, dynamic range was significantly improved to 3.2-196.5 nmol/min/mL (see FIG. 27, Table 25). Shortening reaction time to 30 seconds in activity calculation showed little further improvement.

Example 22

Detection of Lp-PLA2 Activity and its In Vitro Drug Inhibition in Serum

To assess the utility of a modified colorimetric assay for measuring Lp-PLA2 activity and particularly its drug inhibition in serum, 10 serum samples collected from normal donors were assayed. The measured Lp-PLA2 activity shown in FIG. 28 (Table 26) ranged between 130 and 190 nmol/min/mL for these serum samples. The % CV between duplicates of each sample was mostly less than 5%. No matched plasma samples were available for analysis. However, pre-dose plasma samples from 14 subjects described in Example 10 and 11 showed a comparable range of Lp-PLA2 activity between 80 and 200 nmol/min/mL.

Since no serum samples were available from human subjects administered Lp-PLA2 inhibitors, 2 serum samples, BRH28861 and BRH28867, were pre-treated in vitro with different doses of Lp-PLA2 inhibitor Formula II. The dose range used in vitro contained the range of in vivo plasma concentrations of such inhibitor in human subjects receiving drug during clinical studies of Formula II. Based on pharmacokinetics data, 90 ng/mL represented the peak plasma level of Formula II when administered in vivo. These in vitro drug-treated serum samples were then assayed for Lp-PLA2 activity by a modified colorimetric assay. FIG. 29 (Table 27) shows that BRH28861 and BRH28867 reached 88.25% and 90.77% inhibition of Lp-PLA2 activity, respectively, when treated with 90 ng/mL of Formula II in vitro. Higher drug dose at 900 ng/mL level further increased drug inhibition to 97.71% and 92.28% respectively in these two serum samples.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A colorimetric method of determining the percentage of inhibition of Lp-PLA2 activity, the method comprising:
   preparing a solution comprising a substrate for Lp-PLA2 having a colorimetric detectable moiety, which substrate is 1-myristoyl-2-(4-nitrophenylsuccinyl)phosphatidylcholine;
   contacting a first blood sample that is taken from a human subject at a first time with the solution;
   colorimetrically detecting Lp-PLA2 activity from the first blood sample wherein the first blood sample is diluted less than 33 times;
   contacting a second blood sample that is taken from the subject at a second time one hour or more after the first time with the solution, wherein the second blood sample is taken after the subject has been administered a drug that inhibits Lp-PLA2;
   colorimetrically detecting Lp-PLA2 activity from the second blood sample wherein the second blood sample is diluted less than 33 times; and
   detecting greater than 30% inhibition of Lp-PLA2 activity between the first and second blood samples by comparing the activity of the Lp-PLA2 between the first and second blood samples, indicating that the subject has taken a drug that inhibits Lp-PLA2.

2. The method of claim 1, wherein detecting greater than 30% inhibition of Lp-PLA2 activity comprises detecting greater than 90% inhibition of Lp-PLA2 between the first and second blood samples.

3. The method of claim 1, wherein detecting greater than 30% inhibition of Lp-PLA2 activity comprises detecting 85-95% inhibition of Lp-PLA2 between the first and second blood samples.

4. The method of claim 1, wherein the first and second blood samples comprise blood plasma or blood serum samples.

5. The method of claim 1, wherein colorimetrically detecting Lp-PLA2 activity from the first and second blood samples comprises detecting Lp-PLA2 activity within a dynamic range of 100-fold or greater.

6. A method of clinically monitoring a patient to assess the efficacy of an inhibitor of lipoprotein-associated phospholipase A2 (Lp-PLA2), the method comprising:
   receiving a sample from a human patient that has been administered an Lp-PLA2 inhibitor; and
   colorimetrically detecting greater than 30 percent inhibition of Lp-PLA2 from the sample by contacting the sample with a solution comprising a substrate for Lp-PLA2 including a colorimetric detectable moiety, which substrate is 1-myristoyl-2-(4-nitrophenylsuccinyl)phosphatidylcholine and wherein the sample is diluted less than 33 fold.

7. The method of claim 6, wherein colorimetrically detecting greater than 30 percent inhibition comprises detecting greater than 70% inhibition.

8. The method of claim 6, wherein colorimetrically detecting greater than 30 percent inhibition comprises detecting at least 85-95% inhibition.

9. The method of claim 6, wherein colorimetrically detecting greater than 30 percent inhibition comprises detecting 85-95% inhibition.

10. The method of claim 6, wherein receiving a sample comprises receiving a blood plasma or blood serum sample.

11. The method of claim 6, wherein colorimetrically detecting comprises detecting inhibition of Lp-PLA2 from a plurality of samples obtained from the human at more than one time point before and after administration of the Lp-PLA2 inhibitor.

12. The method of claim 6, wherein colorimetrically detecting comprises comparing the activity of Lp-PLA2 from a plurality of samples including at least one sample obtained from the human prior to the administration of the Lp-PLA2 inhibitor.

13. The method of claim 6, wherein the substrate concentration is between about 53 µM to about 1125 µM.

14. The method of claim 6, wherein the substrate concentration is less than 10 times the Km of Lp-PLA2 for the substrate.

15. A method of determining inhibition of lipoprotein-associated phospholipase A2 (Lp-PLA2) enzyme activity from a sample, the method comprising:
   preparing a solution comprising a substrate for Lp-PLA2 having a colorimetric detectable moiety, which substrate is 1-myristoyl-2-(4-nitrophenylsuccinyl)phosphatidylcholine;
   contacting a sample from a human that has been administered an Lp-PLA2 inhibitor, wherein the sample is diluted less than 33 fold by contact with the solution; and
   colorimetrically detecting Lp-PLA2 activity.

16. The method of claim 15, wherein colorimetrically detecting Lp-PLA2 activity comprises detecting greater than 30 percent inhibition.

17. The method of claim 15, wherein colorimetrically detecting Lp-PLA2 activity comprises detecting at least 85-95% inhibition.

18. The method of claim 15, wherein contacting the sample from the human comprises contacting a blood plasma or blood serum sample.

19. The method of claim 15, wherein colorimetrically detecting comprises detecting activity of Lp-PLA2 from a plurality of samples obtained from the human at more than one time point after administration of the Lp-PLA2 inhibitor.

20. The method of claim 15, wherein colorimetrically detecting comprises comparing the activity of Lp-PLA2 from a plurality of samples including at least one sample obtained from the human prior to the administration of the Lp-PLA2 inhibitor.

21. The method of claim 15, wherein the substrate concentration is between about 53 μM to about 1125 μM.

22. The method of claim 15, wherein the substrate concentration is less than 10 times the Km of Lp-PLA2 for the substrate.

23. The method of claim 15, wherein colorimetrically detecting Lp-PLA2 activity comprises detecting Lp-PLA2 activity within a dynamic range of close to 100-fold.

* * * * *